USOO5631351A

United States Patent [19]

Nakamura et al.

[11] Patent Number: 5,631,351
[45] Date of Patent: May 20, 1997

[54] ANTIBODIES TO MDC PROTEINS

[75] Inventors: Yusuke Nakamura, Kanagawa; Mitsuru Emi, Tokyo, both of Japan

[73] Assignees: Cancer Institute; Eisai Co., Ltd., both of Tokyo, Japan

[21] Appl. No.: 477,407

[22] Filed: Jun. 7, 1995

Related U.S. Application Data

[62] Division of Ser. No. 243,542, May 13, 1994.

[30] Foreign Application Priority Data

| May 14, 1993 | [JP] | Japan | 5-136602 |
| Sep. 22, 1993 | [JP] | Japan | 5-257455 |
| Feb. 23, 1994 | [JP] | Japan | 6-49904 |
| Apr. 12, 1994 | [JP] | Japan | 6-73328 |

[51] Int. Cl.$^6$ .......................... A61K 39/395; C07K 16/30; C12P 21/08
[52] U.S. Cl. .......................... 530/387.9; 435/70.21; 435/172.2; 424/139.1
[58] Field of Search .................. 424/138.1, 139.1, 424/143.1, 152.1, 172.1; 435/70.21, 172.2, 240.3, 240.27; 530/350, 387.7, 387.9, 388.22, 389.1

[56] References Cited

PUBLICATIONS

Seaver 1994 Genetic Engineering News vol. 14 No. 4 pp. 10 & 21.
Sevier et al 1981 Clin Chem vol. 27 No. 11: 1797–1806.

*Primary Examiner*—Christine M. Nucker
*Assistant Examiner*—Julie E. Reeves
*Attorney, Agent, or Firm*—Flynn, Thiel, Boutell & Tanis, P.C.

[57] ABSTRACT

The present invention provides an antibody encoded by a gene which is present in a commonly deleted region of a chromosome in breast and ovarian cancers. A monoclonal antibody was prepared by using the protein as antigen and can be utilized in clinical fields for diagnosing cancer.

5 Claims, 8 Drawing Sheets

FIG. 1

| Band | Markers |
|---|---|
| 13.3 | 471 |
| 13.2 | 732 |
| 13.1 | 488, 810 | 484, 491 | 525, 588 | 453 483 571 586 587 606 624 627 636 645 646 654 657 669 680 685 703 708 713 716 717 723 727 745 821 |
| 12 | 500 662 709 728 841 |
| 11.2 | 681 | 11 498 502 505 532 536 596 603 608 631 638 688 693 694 695 705 712 724 729 802 814 818 825 827 828 832 |
| 11.1 | |
| 11.1 | 321 |
| 11.1 | 570 822 |
| 11.2 | 526 543 578 602 690 801 834 | 32 317 412 425 457 460 468 473 475 482 490 492 497 513 520 562 581 630 640 671 683 698 826 1029 1031 1073 1103 1106 1719 1724 |
| 12 | 574 | 90 316 535 583 598 610 | 25 485 552 569 590 599 622 633 637 639 650 687 706 820 823 1024 1063 1079 1101 1709 1711 1715 |
| 21.1 | 1 57 615 1094 1725 | 642 673 677 | 24 415 451 458 463 499 506 524 576 601 605 1059 1702 1706 |
| 21.2 | |
| 21.31 | 403 1018 1705 1707 | 28 35 63 96 97 477 479 501 507 517 527 533 539 541 542 547 567 582 584 592 609 612 614 617 619 634 643 658 670 674 675 701 715 730 736 835 1005 1008 1049 1055 1710 1717 1723 |
| 21.32 | |
| 21.33 | |
| 22 | 7 422 494 515 523 528 611 632 652 653 668 1030 1082 |
| 23.1 | 456 1032 | 44 50 95 428 618 666 679 711 721 1014 1019 | 454 462 489 510 530 548 550 553 565 600 604 625 626 628 644 655 665 676 678 692 699 700 704 744 809 813 816 817 833 1722 CMM86 |
| 23.2 | |
| 23.3 | 696 743 |
| 24.1 | |
| 24.2 | 504 509 591 667 815 |
| 24.3 | 464 546 559 1720 |
| 25.1 | | 452 467 495 540 561 568 607 697 719 726 742 | 315 465 466 480 493 508 511 521 529 551 557 560 593 595 621 623 647 664 672 684 707 808 831 | 486 487 514 516 544 554 563 564 572 577 613 616 641 651 656 660 663 691 733 739 |
| 25.2 | 469 519 594 702 722 737 |
| 25.3 | 518 549 573 597 710 714 735 741 |

17

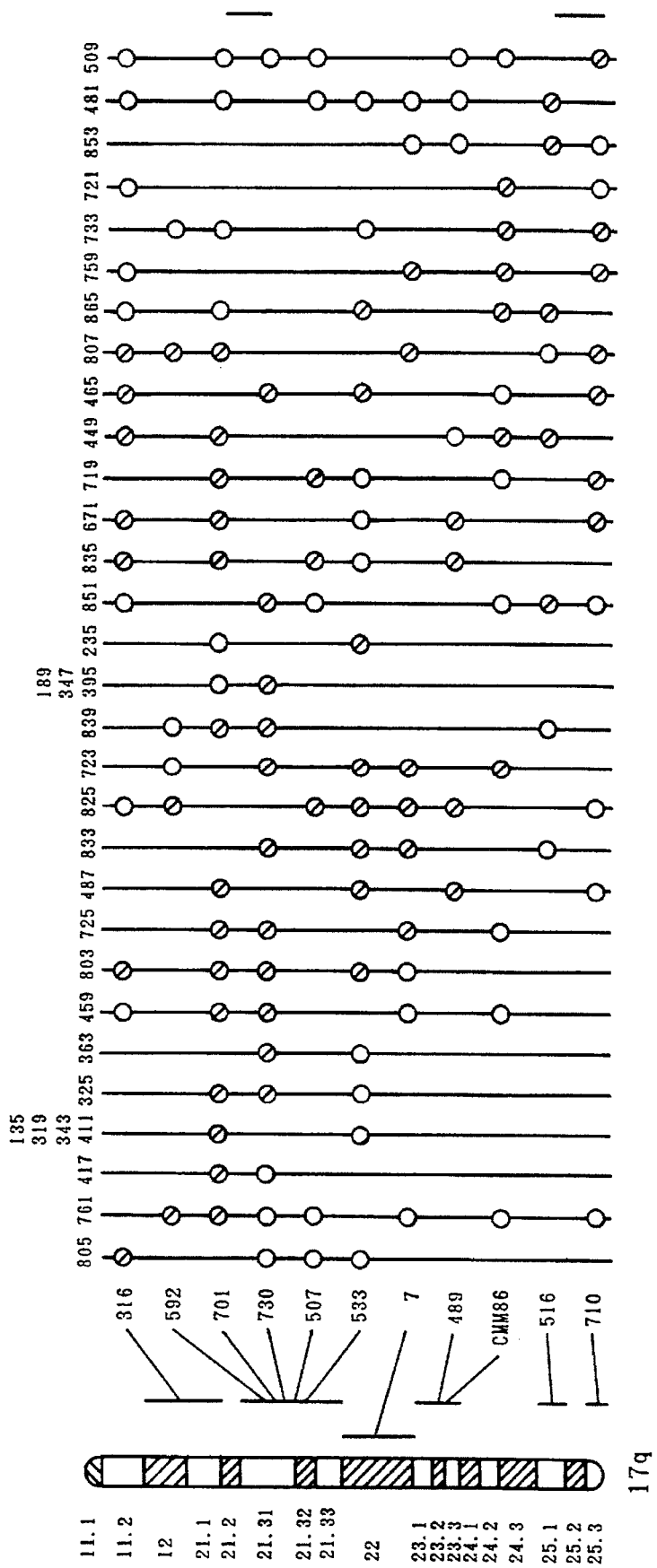

SEQUENCE LISTING ( 1 ) GENERAL INFORMATION:

( i i i ) NUMBER OF SEQUENCES: 20

( 2 ) INFORMATION FOR SEQ ID NO: 1:

( i ) SEQUENCE CHARACTERISTICS:
( A ) LENGTH: 488 amino acids
( B ) TYPE: amino acid
( D ) TOPOLOGY: linear ( i i ) MOLECULE TYPE: protein ( v i ) ORIGINAL SOURCE:
( A ) ORGANISM: Homo sapiens ( v i i ) IMMEDIATE SOURCE:
( A ) LIBRARY: human fetal brain cDNA library ( x i ) SEQUENCE DESCRIPTION: SEQ ID NO: 1:

```
Leu Leu Ser Ser Gln Tyr Val Glu Arg His Phe Ser Arg Glu Gly Thr
  1               5                  10                  15

Thr Gln His Ser Thr Gly Ala Gly Asp His Cys Tyr Tyr Gln Gly Lys
                 20                  25                  30

Leu Arg Gly Asn Pro His Ser Phe Ala Ala Leu Ser Thr Cys Gln Gly
             35                  40                  45

Leu His Gly Val Phe Ser Asp Gly Asn Leu Thr Tyr Ile Val Glu Pro
         50                  55                  60

Gln Glu Val Ala Gly Pro Trp Gly Ala Pro Gln Gly Pro Leu Pro His
 65                  70                  75                  80

Leu Ile Tyr Arg Thr Pro Leu Leu Pro Asp Pro Leu Gly Cys Arg Glu
                 85                  90                  95

Pro Gly Cys Leu Phe Ala Val Pro Ala Gln Ser Ala Pro Pro Asn Arg
                100                 105                 110

Pro Arg Leu Arg Arg Lys Arg Gln Val Arg Arg Gly His Pro Thr Val
            115                 120                 125

His Ser Glu Thr Lys Tyr Val Glu Leu Ile Val Ile Asn Asp His Gln
        130                 135                 140

Leu Phe Glu Gln Met Arg Gln Ser Val Val Leu Thr Ser Asn Phe Ala
145                 150                 155                 160

Lys Ser Val Val Asn Leu Ala Asp Val Ile Tyr Lys Glu Gln Leu Asn
                165                 170                 175

Thr Arg Ile Val Leu Val Ala Met Glu Thr Trp Ala Asp Gly Asp Lys
                180                 185                 190

Ile Gln Val Gln Asp Asp Leu Leu Glu Thr Leu Ala Arg Leu Met Val
            195                 200                 205

Tyr Arg Arg Glu Gly Leu Pro Glu Pro Ser Asn Ala Thr His Leu Phe
    210                 215                 220

Ser Gly Arg Thr Phe Gln Ser Thr Ser Ser Gly Ala Ala Tyr Val Gly
225                 230                 235                 240

Gly Ile Cys Ser Leu Ser His Gly Gly Gly Val Asn Glu Tyr Gly Asn
                245                 250                 255

Met Gly Ala Met Ala Val Thr Leu Ala Gln Thr Leu Gly Gln Asn Leu
            260                 265                 270

Gly Met Met Trp Asn Lys His Arg Ser Ser Ala Gly Asp Cys Lys Cys
        275                 280                 285
```

| Pro | Asp | Ile | Trp | Leu | Gly | Cys | Ile | Met | Glu | Asp | Thr | Gly | Phe | Tyr | Leu |
|-----|-----|-----|-----|-----|-----|-----|-----|-----|-----|-----|-----|-----|-----|-----|-----|
|     | 290 |     |     |     |     |     | 295 |     |     |     | 300 |     |     |     |     |
| Pro | Arg | Lys | Phe | Ser | Arg | Cys | Ser | Ile | Asp | Glu | Tyr | Asn | Gln | Phe | Leu |
| 305 |     |     |     |     | 310 |     |     |     | 315 |     |     |     |     |     | 320 |
| Gln | Glu | Gly | Gly | Gly | Ser | Cys | Leu | Phe | Asn | Lys | Pro | Leu | Lys | Leu | Leu |
|     |     |     |     | 325 |     |     |     | 330 |     |     |     |     |     | 335 |     |
| Asp | Pro | Pro | Glu | Cys | Gly | Asn | Gly | Phe | Val | Glu | Ala | Gly | Glu | Glu | Cys |
|     |     |     | 340 |     |     |     |     | 345 |     |     |     |     | 350 |     |     |
| Asp | Cys | Gly | Ser | Val | Gln | Glu | Cys | Ser | Arg | Ala | Gly | Gly | Asn | Cys | Cys |
|     |     | 355 |     |     |     | 360 |     |     |     |     |     | 365 |     |     |     |
| Lys | Lys | Cys | Thr | Leu | Thr | His | Asp | Ala | Met | Cys | Ser | Asp | Gly | Leu | Cys |
|     | 370 |     |     |     |     | 375 |     |     |     |     | 380 |     |     |     |     |
| Cys | Arg | Arg | Cys | Lys | Tyr | Glu | Pro | Arg | Gly | Val | Ser | Cys | Arg | Glu | Ala |
| 385 |     |     |     |     | 390 |     |     |     |     | 395 |     |     |     |     | 400 |
| Val | Asn | Glu | Cys | Asp | Ile | Ala | Glu | Thr | Cys | Thr | Gly | Asp | Ser | Ser | Gln |
|     |     |     |     | 405 |     |     |     |     | 410 |     |     |     |     | 415 |     |
| Cys | Pro | Pro | Asn | Leu | His | Lys | Leu | Asp | Gly | Tyr | Tyr | Cys | Asp | His | Glu |
|     |     |     | 420 |     |     |     |     | 425 |     |     |     |     | 430 |     |     |
| Gln | Gly | Arg | Cys | Tyr | Gly | Gly | Arg | Cys | Lys | Thr | Arg | Asp | Arg | Gln | Cys |
|     |     | 435 |     |     |     |     | 440 |     |     |     |     | 445 |     |     |     |
| Gln | Val | Leu | Trp | Gly | His | Ala | Ala | Ala | Asp | Arg | Phe | Cys | Tyr | Glu | Lys |
|     | 450 |     |     |     |     | 455 |     |     |     |     | 460 |     |     |     |     |
| Leu | Asn | Val | Glu | Gly | Thr | Glu | Arg | Gly | Ser | Cys | Gly | Arg | Lys | Gly | Ser |
| 465 |     |     |     |     | 470 |     |     |     |     | 475 |     |     |     |     | 480 |
| Gly | Trp | Val | Gln | Cys | Ser | Lys | Gln |     |     |     |     |     |     |     |     |
|     |     |     |     | 485 |     |     | 488 |     |     |     |     |     |     |     |     |

(2) INFORMATION FOR SEQ ID NO: 2:

(i) SEQUENCE CHARACTERISTICS:
        (A) LENGTH: 524 amino acids
        (B) TYPE: amino acid
        (D) TOPOLOGY: linear (ii) MOLECULE TYPE: protein (vi) ORIGINAL SOURCE:
        (A) ORGANISM: Homo sapiens (vii) IMMEDIATE SOURCE:
        (A) LIBRARY: human fetal brain cDNA library (xi) SEQUENCE DESCRIPTION: SEQ ID NO: 2:

| Met | Cys | Trp | Leu | Ser | His | Gln | Leu | Leu | Ser | Ser | Gln | Tyr | Val | Glu | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| His | Phe | Ser | Arg | Glu | Gly | Thr | Thr | Gln | His | Ser | Thr | Gly | Ala | Gly | Asp |
|     |     |     | 20  |     |     |     |     | 25  |     |     |     |     | 30  |     |     |
| His | Cys | Tyr | Tyr | Gln | Gly | Lys | Leu | Arg | Gly | Asn | Pro | His | Ser | Phe | Ala |
|     |     | 35  |     |     |     |     | 40  |     |     |     |     | 45  |     |     |     |
| Ala | Leu | Ser | Thr | Cys | Gln | Gly | Leu | His | Gly | Val | Phe | Ser | Asp | Gly | Asn |
|     | 50  |     |     |     |     | 55  |     |     |     |     | 60  |     |     |     |     |
| Leu | Thr | Tyr | Ile | Val | Glu | Pro | Gln | Glu | Val | Ala | Gly | Pro | Trp | Gly | Ala |
| 65  |     |     |     |     | 70  |     |     |     |     | 75  |     |     |     |     | 80  |
| Pro | Gln | Gly | Pro | Leu | Pro | His | Leu | Ile | Tyr | Arg | Thr | Pro | Leu | Leu | Pro |
|     |     |     |     | 85  |     |     |     |     | 90  |     |     |     |     | 95  |     |
| Asp | Pro | Leu | Gly | Cys | Arg | Glu | Pro | Gly | Cys | Leu | Phe | Ala | Val | Pro | Ala |
|     |     |     | 100 |     |     |     |     | 105 |     |     |     |     | 110 |     |     |
| Gln | Ser | Ala | Pro | Pro | Asn | Arg | Pro | Arg | Leu | Arg | Arg | Lys | Arg | Gln | Val |
|     |     | 115 |     |     |     |     | 120 |     |     |     |     | 125 |     |     |     |

```
Arg Arg Gly His Pro Thr Val His Ser Glu Thr Lys Tyr Val Glu Leu
    130             135             140

Ile Val Ile Asn Asp His Gln Leu Phe Glu Gln Met Arg Gln Ser Val
145             150             155                         160

Val Leu Thr Ser Asn Phe Ala Lys Ser Val Val Asn Leu Ala Asp Val
                165             170                     175

Ile Tyr Lys Glu Gln Leu Asn Thr Arg Ile Val Leu Val Ala Met Glu
            180             185                 190

Thr Trp Ala Asp Gly Asp Lys Ile Gln Val Gln Asp Asp Leu Leu Glu
        195             200             205

Thr Leu Ala Arg Leu Met Val Tyr Arg Arg Glu Gly Leu Pro Glu Pro
    210             215             220

Ser Asn Ala Thr His Leu Phe Ser Gly Arg Thr Phe Gln Ser Thr Ser
225             230             235                         240

Ser Gly Ala Ala Tyr Val Gly Gly Ile Cys Ser Leu Ser His Gly Gly
                245             250                     255

Gly Val Asn Glu Tyr Gly Asn Met Gly Ala Met Ala Val Thr Leu Ala
            260             265                 270

Gln Thr Leu Gly Gln Asn Leu Gly Met Met Trp Asn Lys His Arg Ser
        275             280             285

Ser Ala Gly Asp Cys Lys Cys Pro Asp Ile Trp Leu Gly Cys Ile Met
290             295             300

Glu Asp Thr Gly Phe Tyr Leu Pro Arg Lys Phe Ser Arg Cys Ser Ile
305             310             315                         320

Asp Glu Tyr Asn Gln Phe Leu Gln Glu Gly Gly Ser Cys Leu Phe
                325             330                     335

Asn Lys Pro Leu Lys Leu Leu Asp Pro Pro Glu Cys Gly Asn Gly Phe
            340             345                 350

Val Glu Ala Gly Glu Glu Cys Asp Cys Gly Ser Val Gln Glu Cys Ser
        355             360             365

Arg Ala Gly Gly Asn Cys Cys Lys Lys Cys Thr Leu Thr His Asp Ala
    370             375             380

Met Cys Ser Asp Gly Leu Cys Cys Arg Arg Cys Lys Tyr Glu Pro Arg
385             390             395                         400

Gly Val Ser Cys Arg Glu Ala Val Asn Glu Cys Asp Ile Ala Glu Thr
                405             410                     415

Cys Thr Gly Asp Ser Ser Gln Cys Pro Pro Asn Leu His Lys Leu Asp
            420             425                 430

Gly Tyr Tyr Cys Asp His Glu Gln Gly Arg Cys Tyr Gly Gly Arg Cys
        435             440             445

Lys Thr Arg Asp Arg Gln Cys Gln Val Leu Trp Gly His Ala Ala Ala
    450             455             460

Asp Arg Phe Cys Tyr Glu Lys Leu Asn Val Glu Gly Thr Glu Arg Gly
465             470             475                         480

Ser Cys Gly Arg Lys Gly Ser Gly Trp Val Gln Cys Ser Lys Gln Pro
                485             490                     495

Gln Gln Gly Arg Ala Val Trp Leu Pro Pro Leu Cys Gln His Leu Trp
            500             505                 510

Ser Ser Ser Ala Arg Gly Pro Gly Gly Arg His Gln
        515             520             524
```

( 2 ) INFORMATION FOR SEQ ID NO: 3:

( i ) SEQUENCE CHARACTERISTICS:

( A ) LENGTH: 670 amino acids
( B ) TYPE: amino acid
( D ) TOPOLOGY: linear ( i i ) MOLECULE TYPE: protein ( v i ) ORIGINAL SOURCE:
    ( A ) ORGANISM: Homo sapiens ( v i i ) IMMEDIATE SOURCE:
    ( A ) LIBRARY: human fetal brain cDNA library ( x i ) SEQUENCE DESCRIPTION: SEQ ID NO: 3:

```
Met Cys Trp Leu Ser His Gln Leu Leu Ser Ser Gln Tyr Val Glu Arg
 1               5                  10                  15

His Phe Ser Arg Glu Gly Thr Thr Gln His Ser Thr Gly Ala Gly Asp
            20                  25                  30

His Cys Tyr Tyr Gln Gly Lys Leu Arg Gly Asn Pro His Ser Phe Ala
        35                  40                  45

Ala Leu Ser Thr Cys Gln Gly Leu His Gly Val Phe Ser Asp Gly Asn
 50                  55                  60

Leu Thr Tyr Ile Val Glu Pro Gln Glu Val Ala Gly Pro Trp Gly Ala
 65                  70                  75                  80

Pro Gln Gly Pro Leu Pro His Leu Ile Tyr Arg Thr Pro Leu Leu Pro
                85                  90                  95

Asp Pro Leu Gly Cys Arg Glu Pro Gly Cys Leu Phe Ala Val Pro Ala
            100                 105                 110

Gln Ser Ala Pro Pro Asn Arg Pro Arg Leu Arg Arg Lys Arg Gln Val
        115                 120                 125

Arg Arg Gly His Pro Thr Val His Ser Glu Thr Lys Tyr Val Glu Leu
130                 135                 140

Ile Val Ile Asn Asp His Gln Leu Phe Glu Gln Met Arg Gln Ser Val
145                 150                 155                 160

Val Leu Thr Ser Asn Phe Ala Lys Ser Val Val Asn Leu Ala Asp Val
                165                 170                 175

Ile Tyr Lys Glu Gln Leu Asn Thr Arg Ile Val Leu Val Ala Met Glu
            180                 185                 190

Thr Trp Ala Asp Gly Asp Lys Ile Gln Val Gln Asp Asp Leu Leu Glu
        195                 200                 205

Thr Leu Ala Arg Leu Met Val Tyr Arg Arg Glu Gly Leu Pro Glu Pro
210                 215                 220

Ser Asn Ala Thr His Leu Phe Ser Gly Arg Thr Phe Gln Ser Thr Ser
225                 230                 235                 240

Ser Gly Ala Ala Tyr Val Gly Gly Ile Cys Ser Leu Ser His Gly Gly
                245                 250                 255

Gly Val Asn Glu Tyr Gly Asn Met Gly Ala Met Ala Val Thr Leu Ala
            260                 265                 270

Gln Thr Leu Gly Gln Asn Leu Gly Met Met Trp Asn Lys His Arg Ser
        275                 280                 285

Ser Ala Gly Asp Cys Lys Cys Pro Asp Ile Trp Leu Gly Cys Ile Met
290                 295                 300

Glu Asp Thr Gly Phe Tyr Leu Pro Arg Lys Phe Ser Arg Cys Ser Ile
305                 310                 315                 320

Asp Glu Tyr Asn Gln Phe Leu Gln Glu Gly Gly Gly Ser Cys Leu Phe
                325                 330                 335

Asn Lys Pro Leu Lys Leu Leu Asp Pro Pro Glu Cys Gly Asn Gly Phe
            340                 345                 350
```

```
Val  Glu  Ala  Gly  Glu  Glu  Cys  Asp  Cys  Gly  Ser  Val  Gln  Glu  Cys  Ser
          355                      360                 365

Arg  Ala  Gly  Gly  Asn  Cys  Cys  Lys  Lys  Cys  Thr  Leu  Thr  His  Asp  Ala
          370                      375                 380

Met  Cys  Ser  Asp  Gly  Leu  Cys  Cys  Arg  Arg  Cys  Lys  Tyr  Glu  Pro  Arg
385                      390                      395                           400

Gly  Val  Ser  Cys  Arg  Glu  Ala  Val  Asn  Glu  Cys  Asp  Ile  Ala  Glu  Thr
                    405                      410                      415

Cys  Thr  Gly  Asp  Ser  Ser  Gln  Cys  Pro  Pro  Asn  Leu  His  Lys  Leu  Asp
                    420                      425                 430

Gly  Tyr  Tyr  Cys  Asp  His  Glu  Gln  Gly  Arg  Cys  Tyr  Gly  Gly  Arg  Cys
          435                      440                      445

Lys  Thr  Arg  Asp  Arg  Gln  Cys  Gln  Val  Leu  Trp  Gly  His  Ala  Ala  Ala
          450                      455                      460

Asp  Arg  Phe  Cys  Tyr  Glu  Lys  Leu  Asn  Val  Glu  Gly  Thr  Glu  Arg  Gly
465                      470                      475                           480

Ser  Cys  Gly  Arg  Lys  Gly  Ser  Gly  Trp  Val  Gln  Cys  Ser  Lys  Gln  Asp
                    485                      490                      495

Val  Leu  Cys  Gly  Phe  Leu  Leu  Cys  Val  Asn  Ile  Ser  Gly  Ala  Pro  Arg
                    500                      505                      510

Leu  Gly  Asp  Leu  Val  Gly  Asp  Ile  Ser  Ser  Val  Thr  Phe  Tyr  His  Gln
          515                      520                      525

Gly  Lys  Glu  Leu  Asp  Cys  Arg  Gly  Gly  His  Val  Gln  Leu  Ala  Asp  Gly
          530                      535                      540

Ser  Asp  Leu  Ser  Tyr  Val  Glu  Asp  Gly  Thr  Ala  Cys  Gly  Pro  Asn  Met
545                      550                      555                           560

Leu  Cys  Leu  Asp  His  Arg  Cys  Leu  Pro  Ala  Ser  Ala  Phe  Asn  Phe  Ser
                    565                      570                      575

Thr  Cys  Pro  Gly  Ser  Gly  Glu  Arg  Arg  Ile  Cys  Ser  His  His  Gly  Val
                    580                      585                      590

Cys  Ser  Asn  Glu  Gly  Lys  Cys  Ile  Cys  Gln  Pro  Asp  Trp  Thr  Gly  Lys
          595                      600                      605

Asp  Cys  Ser  Ile  His  Asn  Pro  Leu  Pro  Thr  Ser  Pro  Pro  Thr  Gly  Glu
          610                      615                      620

Thr  Glu  Arg  Tyr  Lys  Gly  Pro  Ser  Gly  Thr  Asn  Ile  Ile  Ile  Gly  Ser
625                      630                      635                           640

Ile  Ala  Gly  Ala  Val  Leu  Val  Ala  Ala  Ile  Val  Leu  Gly  Gly  Thr  Gly
                    645                      650                      655

Trp  Gly  Phe  Lys  Asn  Ile  Arg  Arg  Gly  Arg  Ser  Gly  Gly  Ala
          660                      665                 670
```

( 2 ) INFORMATION FOR SEQ ID NO: 4:

( i ) SEQUENCE CHARACTERISTICS:
        ( A ) LENGTH: 769 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Homo sapiens ( v i i ) IMMEDIATE SOURCE:
        ( A ) LIBRARY: human fetal brain cDNA library ( x i ) SEQUENCE DESCRIPTION: SEQ ID NO: 4:

| | | | | | | | | | | | | | | |
|---|---|---|---|---|---|---|---|---|---|---|---|---|---|---|
| Met | Arg | Leu | Leu | Arg | Arg | Trp | Ala | Phe | Ala | Ala | Leu | Leu | Leu | Ser | Leu |
| 1 | | | | 5 | | | | | 10 | | | | | 15 | |
| Leu | Pro | Thr | Pro | Gly | Leu | Gly | Thr | Gln | Gly | Pro | Ala | Gly | Ala | Leu | Arg |
| | | | 20 | | | | | 25 | | | | | 30 | | |
| Trp | Gly | Gly | Leu | Pro | Gln | Leu | Gly | Gly | Pro | Gly | Ala | Pro | Glu | Val | Thr |
| | | 35 | | | | | 40 | | | | | 45 | | | |
| Glu | Pro | Ser | Arg | Leu | Val | Arg | Glu | Ser | Ser | Gly | Glu | Val | Arg | Lys | |
| | 50 | | | | | 55 | | | | 60 | | | | | |
| Gln | Gln | Leu | Asp | Thr | Arg | Val | Arg | Gln | Glu | Pro | Pro | Gly | Gly | Pro | Pro |
| 65 | | | | | 70 | | | | 75 | | | | | | 80 |
| Val | His | Leu | Ala | Gln | Val | Ser | Phe | Val | Ile | Pro | Ala | Phe | Asn | Ser | Asn |
| | | | | 85 | | | | | 90 | | | | | 95 | |
| Phe | Thr | Leu | Asp | Leu | Glu | Leu | Asn | His | His | Leu | Leu | Ser | Ser | Gln | Tyr |
| | | | 100 | | | | | 105 | | | | | 110 | | |
| Val | Glu | Arg | His | Phe | Ser | Arg | Glu | Gly | Thr | Thr | Gln | His | Ser | Thr | Gly |
| | | 115 | | | | | 120 | | | | | 125 | | | |
| Ala | Gly | Asp | His | Cys | Tyr | Tyr | Gln | Gly | Lys | Leu | Arg | Gly | Asn | Pro | His |
| | 130 | | | | 135 | | | | | 140 | | | | | |
| Ser | Phe | Ala | Ala | Leu | Ser | Thr | Cys | Gln | Gly | Leu | His | Gly | Val | Phe | Ser |
| 145 | | | | | 150 | | | | | 155 | | | | | 160 |
| Asp | Gly | Asn | Leu | Thr | Tyr | Ile | Val | Glu | Pro | Gln | Glu | Val | Ala | Gly | Pro |
| | | | | 165 | | | | | 170 | | | | | 175 | |
| Trp | Gly | Ala | Pro | Gln | Gly | Pro | Leu | Pro | His | Leu | Ile | Tyr | Arg | Thr | Pro |
| | | | 180 | | | | | 185 | | | | | 190 | | |
| Leu | Leu | Pro | Asp | Pro | Leu | Gly | Cys | Arg | Glu | Pro | Gly | Cys | Leu | Phe | Ala |
| | | 195 | | | | | 200 | | | | | 205 | | | |
| Val | Pro | Ala | Gln | Ser | Ala | Pro | Pro | Asn | Arg | Pro | Arg | Leu | Arg | Arg | Lys |
| | 210 | | | | | 215 | | | | | 220 | | | | |
| Arg | Gln | Val | Arg | Arg | Gly | His | Pro | Thr | Val | His | Ser | Glu | Thr | Lys | Tyr |
| 225 | | | | | 230 | | | | | 235 | | | | | 240 |
| Val | Glu | Leu | Ile | Val | Ile | Asn | Asp | His | Gln | Leu | Phe | Glu | Gln | Met | Arg |
| | | | | 245 | | | | | 250 | | | | | 255 | |
| Gln | Ser | Val | Val | Leu | Thr | Ser | Asn | Phe | Ala | Lys | Ser | Val | Val | Asn | Leu |
| | | | 260 | | | | | 265 | | | | | 270 | | |
| Ala | Asp | Val | Ile | Tyr | Lys | Glu | Gln | Leu | Asn | Thr | Arg | Ile | Val | Leu | Val |
| | | 275 | | | | | 280 | | | | | 285 | | | |
| Ala | Met | Glu | Thr | Trp | Ala | Asp | Gly | Asp | Lys | Ile | Gln | Val | Gln | Asp | Asp |
| | 290 | | | | | 295 | | | | | 300 | | | | |
| Leu | Leu | Glu | Thr | Leu | Ala | Arg | Leu | Met | Val | Tyr | Arg | Arg | Glu | Gly | Leu |
| 305 | | | | 310 | | | | | 315 | | | | | | 320 |
| Pro | Glu | Pro | Ser | Asn | Ala | Thr | His | Leu | Phe | Ser | Gly | Arg | Thr | Phe | Gln |
| | | | | 325 | | | | | 330 | | | | | 335 | |
| Ser | Thr | Ser | Ser | Gly | Ala | Ala | Tyr | Val | Gly | Gly | Ile | Cys | Ser | Leu | Ser |
| | | | 340 | | | | | 345 | | | | | 350 | | |
| His | Gly | Gly | Gly | Val | Asn | Glu | Tyr | Gly | Asn | Met | Gly | Ala | Met | Ala | Val |
| | | | 355 | | | | | 360 | | | | | 365 | | |
| Thr | Leu | Ala | Gln | Thr | Leu | Gly | Gln | Asn | Leu | Gly | Met | Met | Trp | Asn | Lys |
| | 370 | | | | | 375 | | | | | 380 | | | | |
| His | Arg | Ser | Ser | Ala | Gly | Asp | Cys | Lys | Cys | Pro | Asp | Ile | Trp | Leu | Gly |
| 385 | | | | | 390 | | | | | 395 | | | | | 400 |
| Cys | Ile | Met | Glu | Asp | Thr | Gly | Phe | Tyr | Leu | Pro | Arg | Lys | Phe | Ser | Arg |
| | | | | 405 | | | | | 410 | | | | | 415 | |
| Cys | Ser | Ile | Asp | Glu | Tyr | Asn | Gln | Phe | Leu | Gln | Glu | Gly | Gly | Gly | Ser |
| | | | 420 | | | | | 425 | | | | | 430 | | |

| | | | | | | | | | | | | | |
|---|---|---|---|---|---|---|---|---|---|---|---|---|---|
| Cys | Leu | Phe 435 | Asn | Lys | Pro | Leu 440 | Leu | Leu | Asp | Pro 445 | Pro | Glu | Cys | Gly |
| Asn | Gly 450 | Phe | Val | Glu | Ala | Gly 455 | Glu | Glu | Cys | Asp 460 | Cys | Gly | Ser | Val | Gln |
| Glu 465 | Cys | Ser | Arg | Ala | Gly 470 | Gly | Asn | Cys | Cys | Lys 475 | Lys | Cys | Thr | Leu | Thr 480 |
| His | Asp | Ala | Met | Cys 485 | Ser | Asp | Gly | Leu | Cys 490 | Arg | Arg | Cys | Lys 495 | Tyr |
| Glu | Pro | Arg | Gly 500 | Val | Ser | Cys | Arg | Glu 505 | Ala | Val | Asn | Glu | Cys 510 | Asp | Ile |
| Ala | Glu | Thr 515 | Cys | Thr | Gly | Asp | Ser 520 | Ser | Gln | Cys | Pro | Pro 525 | Asn | Leu | His |
| Lys | Leu 530 | Asp | Gly | Tyr | Tyr | Cys 535 | Asp | His | Glu | Gln | Gly 540 | Arg | Cys | Tyr | Gly |
| Gly 545 | Arg | Cys | Lys | Thr | Arg 550 | Asp | Arg | Gln | Cys | Gln 555 | Val | Leu | Trp | Gly | His 560 |
| Ala | Ala | Ala | Asp | Arg 565 | Phe | Cys | Tyr | Glu | Lys 570 | Leu | Asn | Val | Glu | Gly 575 | Thr |
| Glu | Arg | Gly | Ser 580 | Cys | Gly | Arg | Lys | Gly 585 | Ser | Gly | Trp | Val | Gln 590 | Cys | Ser |
| Lys | Gln | Asp 595 | Val | Leu | Cys | Gly | Phe 600 | Leu | Leu | Cys | Val | Asn 605 | Ile | Ser | Gly |
| Ala | Pro | Arg 610 | Leu | Gly | Asp | Leu | Val 615 | Gly | Asp | Ile | Ser 620 | Ser | Val | Thr | Phe |
| Tyr 625 | His | Gln | Gly | Lys | Glu 630 | Leu | Asp | Cys | Arg | Gly 635 | Gly | His | Val | Gln | Leu 640 |
| Ala | Asp | Gly | Ser | Asp 645 | Leu | Ser | Tyr | Val | Glu 650 | Asp | Gly | Thr | Ala | Cys 655 | Gly |
| Pro | Asn | Met | Leu 660 | Cys | Leu | Asp | His | Arg 665 | Cys | Leu | Pro | Ala | Ser 670 | Ala | Phe |
| Asn | Phe | Ser 675 | Thr | Cys | Pro | Gly | Ser 680 | Gly | Glu | Arg | Arg | Ile 685 | Cys | Ser | His |
| His | Gly 690 | Val | Cys | Ser | Asn | Glu 695 | Gly | Lys | Cys | Ile | Cys 700 | Gln | Pro | Asp | Trp |
| Thr 705 | Gly | Lys | Asp | Cys | Ser 710 | Ile | His | Asn | Pro | Leu 715 | Pro | Thr | Ser | Pro 720 |
| Thr | Gly | Glu | Thr | Glu 725 | Arg | Tyr | Lys | Gly | Pro 730 | Ser | Gly | Thr | Asn | Ile 735 | Ile |
| Ile | Gly | Ser | Ile 740 | Ala | Gly | Ala | Val | Leu 745 | Val | Ala | Ala | Ile | Val 750 | Leu | Gly |
| Gly | Thr | Gly 755 | Trp | Gly | Phe | Lys | Asn 760 | Ile | Arg | Arg | Gly | Arg 765 | Ser | Gly | Gly |
| Ala 769 |

( 2 ) INFORMATION FOR SEQ ID NO: 5:

( i ) SEQUENCE CHARACTERISTICS:
        ( A ) LENGTH: 1464 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: Homo sapiens ( v i i ) IMMEDIATE SOURCE:
    ( A ) LIBRARY: human fetal brain cDNA library ( i x ) FEATURE:
    ( A ) NAME/KEY: CDS
    ( B ) LOCATION: 1..1464

( x i ) SEQUENCE DESCRIPTION: SEQ ID NO: 5:

```
CTC CTC TCC TCG CAA TAC GTG GAG CGC CAC TTC AGC CGG GAG GGA ACA      48
Leu Leu Ser Ser Gln Tyr Val Glu Arg His Phe Ser Arg Glu Gly Thr
 1               5                  10                  15

ACC CAG CAC AGC ACC GGG GCT GGA GAC CAC TGC TAC TAC CAG GGG AAG      96
Thr Gln His Ser Thr Gly Ala Gly Asp His Cys Tyr Tyr Gln Gly Lys
             20                  25                  30

CTC CGG GGG AAC CCG CAC TCC TTC GCC GCC CTC TCC ACC TGC CAG GGG     144
Leu Arg Gly Asn Pro His Ser Phe Ala Ala Leu Ser Thr Cys Gln Gly
         35                  40                  45

CTG CAT GGG GTC TTC TCT GAT GGG AAC TTG ACT TAC ATC GTG GAG CCC     192
Leu His Gly Val Phe Ser Asp Gly Asn Leu Thr Tyr Ile Val Glu Pro
     50                  55                  60

CAA GAG GTG GCT GGA CCT TGG GGA GCC CCT CAG GGA CCC CTT CCC CAC     240
Gln Glu Val Ala Gly Pro Trp Gly Ala Pro Gln Gly Pro Leu Pro His
 65                  70                  75                  80

CTC ATT TAC CGG ACC CCT CTC CTC CCA GAT CCC CTC GGA TGC AGG GAA     288
Leu Ile Tyr Arg Thr Pro Leu Leu Pro Asp Pro Leu Gly Cys Arg Glu
                 85                  90                  95

CCA GGC TGC CTG TTT GCT GTG CCT GCC CAG TCG GCT CCT CCA AAC CGG     336
Pro Gly Cys Leu Phe Ala Val Pro Ala Gln Ser Ala Pro Pro Asn Arg
            100                 105                 110

CCG AGG CTG AGA AGG AAA AGG CAG GTC CGC CGG GGC CAC CCT ACA GTG     384
Pro Arg Leu Arg Arg Lys Arg Gln Val Arg Arg Gly His Pro Thr Val
        115                 120                 125

CAC AGT GAA ACC AAG TAT GTG GAG CTA ATT GTG ATC AAC GAC CAC CAG     432
His Ser Glu Thr Lys Tyr Val Glu Leu Ile Val Ile Asn Asp His Gln
    130                 135                 140

CTG TTC GAG CAG ATG CGA CAG TCG GTG GTC CTC ACC AGC AAC TTT GCC     480
Leu Phe Glu Gln Met Arg Gln Ser Val Val Leu Thr Ser Asn Phe Ala
145                 150                 155                 160

AAG TCC GTG GTG AAC CTG GCC GAT GTG ATA TAC AAG GAG CAG CTC AAC     528
Lys Ser Val Val Asn Leu Ala Asp Val Ile Tyr Lys Glu Gln Leu Asn
                165                 170                 175

ACT CGC ATC GTC CTG GTT GCC ATG GAA ACA TGG GCA GAT GGG GAC AAG     576
Thr Arg Ile Val Leu Val Ala Met Glu Thr Trp Ala Asp Gly Asp Lys
            180                 185                 190

ATC CAG GTG CAG GAT GAC CTC CTG GAG ACC CTG GCC CGG CTC ATG GTC     624
Ile Gln Val Gln Asp Asp Leu Leu Glu Thr Leu Ala Arg Leu Met Val
        195                 200                 205

TAC CGA CGG GAG GGT CTG CCT GAG CCC AGT AAT GCC ACC CAC CTC TTC     672
Tyr Arg Arg Glu Gly Leu Pro Glu Pro Ser Asn Ala Thr His Leu Phe
    210                 215                 220

TCG GGC AGG ACC TTC CAG AGC ACG AGC AGC GGG GCA GCC TAC GTG GGG     720
Ser Gly Arg Thr Phe Gln Ser Thr Ser Ser Gly Ala Ala Tyr Val Gly
225                 230                 235                 240

GGC ATA TGC TCC CTG TCC CAT GGC GGG GTG AAC GAG TAC GGC AAC          768
Gly Ile Cys Ser Leu Ser His Gly Gly Val Asn Glu Tyr Gly Asn
                245                 250                 255

ATG GGG GCG ATG GCC GTG ACC CTT GCC CAG ACG CTG GGA CAG AAC CTG     816
Met Gly Ala Met Ala Val Thr Leu Ala Gln Thr Leu Gly Gln Asn Leu
            260                 265                 270
```

| | | | | | | | | | | | | | | | | |
|---|---|---|---|---|---|---|---|---|---|---|---|---|---|---|---|---|
| GGC | ATG | ATG | TGG | AAC | AAA | CAC | CGG | AGC | TCG | GCA | GGG | GAC | TGC | AAG | TGT | 864 |
| Gly | Met | Met<br>275 | Trp | Asn | Lys | His<br>280 | Arg | Ser | Ser | Ala | Gly<br>285 | Asp | Cys | Lys | Cys | |
| CCA | GAC | ATC | TGG | CTG | GGC | TGC | ATC | ATG | GAG | GAC | ACT | GGG | TTC | TAC | CTG | 912 |
| Pro | Asp<br>290 | Ile | Trp | Leu | Gly | Cys<br>295 | Ile | Met | Glu | Asp | Thr<br>300 | Gly | Phe | Tyr | Leu | |
| CCC | CGC | AAG | TTC | TCT | CGC | TGC | AGC | ATC | GAC | GAG | TAC | AAC | CAG | TTT | CTG | 960 |
| Pro<br>305 | Arg | Lys | Phe | Ser | Arg<br>310 | Cys | Ser | Ile | Asp | Glu<br>315 | Tyr | Asn | Gln | Phe | Leu<br>320 | |
| CAG | GAG | GGT | GGT | GGC | AGC | TGC | CTC | TTC | AAC | AAG | CCC | CTC | AAG | CTC | CTG | 1008 |
| Gln | Glu | Gly | Gly | Gly<br>325 | Ser | Cys | Leu | Phe | Asn<br>330 | Lys | Pro | Leu | Lys<br>335 | Leu | Leu | |
| GAC | CCC | CCA | GAG | TGC | GGG | AAC | GGC | TTC | GTG | GAG | GCA | GGG | GAG | GAG | TGC | 1056 |
| Asp | Pro | Pro | Glu<br>340 | Cys | Gly | Asn | Gly | Phe<br>345 | Val | Glu | Ala | Gly | Glu<br>350 | Glu | Cys | |
| GAC | TGC | GGC | TCG | GTG | CAG | GAG | TGC | AGC | CGC | GCA | GGT | GGC | AAC | TGC | TGC | 1104 |
| Asp | Cys | Gly<br>355 | Ser | Val | Gln | Glu | Cys<br>360 | Ser | Arg | Ala | Gly | Gly<br>365 | Asn | Cys | Cys | |
| AAG | AAA | TGC | ACC | CTG | ACT | CAC | GAC | GCC | ATG | TGC | AGC | GAC | GGG | CTC | TGC | 1152 |
| Lys | Lys<br>370 | Cys | Thr | Leu | Thr | His<br>375 | Asp | Ala | Met | Cys | Ser<br>380 | Asp | Gly | Leu | Cys | |
| TGT | CGC | CGC | TGC | AAG | TAC | GAA | CCA | CGG | GGT | GTG | TCC | TGC | CGA | GAG | GCC | 1200 |
| Cys<br>385 | Arg | Arg | Cys | Lys | Tyr<br>390 | Glu | Pro | Arg | Gly | Val<br>395 | Ser | Cys | Arg | Glu | Ala<br>400 | |
| GTG | AAC | GAG | TGC | GAC | ATC | GCG | GAG | ACC | TGC | ACC | GGG | GAC | TCT | AGC | CAG | 1248 |
| Val | Asn | Glu | Cys | Asp | Ile<br>405 | Ala | Glu | Thr | Cys | Thr<br>410 | Gly | Asp | Ser | Ser<br>415 | Gln | |
| TGC | CCG | CCT | AAC | CTG | CAC | AAG | CTG | GAC | GGT | TAC | TAC | TGT | GAC | CAT | GAG | 1296 |
| Cys | Pro | Pro | Asn<br>420 | Leu | His | Lys | Leu | Asp<br>425 | Gly | Tyr | Tyr | Cys | Asp<br>430 | His | Glu | |
| CAG | GGC | CGC | TGC | TAC | GGA | GGT | CGC | TGC | AAA | ACC | CGG | GAC | CGG | CAG | TGC | 1344 |
| Gln | Gly | Arg<br>435 | Cys | Tyr | Gly | Gly | Arg<br>440 | Cys | Lys | Thr | Arg | Asp<br>445 | Arg | Gln | Cys | |
| CAG | GTT | CTT | TGG | GGC | CAT | GCG | GCT | GCT | GAT | CGC | TTC | TGC | TAC | GAG | AAG | 1392 |
| Gln | Val | Leu<br>450 | Trp | Gly | His | Ala | Ala<br>455 | Ala | Asp | Arg | Phe | Cys<br>460 | Tyr | Glu | Lys | |
| CTG | AAT | GTG | GAG | GGG | ACG | GAG | CGT | GGG | AGC | TGT | GGG | CGC | AAG | GGA | TCC | 1440 |
| Leu<br>465 | Asn | Val | Glu | Gly | Thr<br>470 | Glu | Arg | Gly | Ser | Cys<br>475 | Gly | Arg | Lys | Gly | Ser<br>480 | |
| GGC | TGG | GTC | CAG | TGC | AGT | AAG | CAG | | | | | | | | | 1464 |
| Gly | Trp | Val | Gln | Cys<br>485 | Ser | Lys | Gln | | | | | | | | | |

( 2 ) INFORMATION FOR SEQ ID NO: 6:

( i ) SEQUENCE CHARACTERISTICS:
        ( A ) LENGTH: 2923 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: Homo sapiens ( v i i ) IMMEDIATE SOURCE:
        ( A ) LIBRARY: human fetal brain cDNA library ( i x ) FEATURE:
        ( A ) NAME/KEY: 5'UTR
        ( B ) LOCATION: 1..27

( i x ) FEATURE:
        ( A ) NAME/KEY: 3'UTR
        ( B ) LOCATION: 1600..2923

( i x ) FEATURE:
  ( A ) NAME/KEY: CDS
  ( B ) LOCATION: 28..1599

( x i ) SEQUENCE DESCRIPTION: SEQ ID NO: 6:

```
GCGTTTACTG GCAAACCGCA TTTGTAA ATG TGC TGG CTG AGC CAC CAA CTC           51
                              Met Cys Trp Leu Ser His Gln Leu
                                1                   5

CTC TCC TCG CAA TAC GTG GAG CGC CAC TTC AGC CGG GAG GGG ACA ACC          99
Leu Ser Ser Gln Tyr Val Glu Arg His Phe Ser Arg Glu Gly Thr Thr
        10              15                  20

CAG CAC AGC ACC GGG GCT GGA GAC CAC TGC TAC TAC CAG GGG AAG CTC         147
Gln His Ser Thr Gly Ala Gly Asp His Cys Tyr Tyr Gln Gly Lys Leu
 25              30                  35                      40

CGG GGG AAC CCG CAC TCC TTC GCC GCC CTC TCC ACC TGC CAG GGG CTG         195
Arg Gly Asn Pro His Ser Phe Ala Ala Leu Ser Thr Cys Gln Gly Leu
                 45                  50                  55

CAT GGG GTC TTC TCT GAT GGG AAC TTG ACT TAC ATC GTG GAG CCC CAA         243
His Gly Val Phe Ser Asp Gly Asn Leu Thr Tyr Ile Val Glu Pro Gln
             60                  65                  70

GAG GTG GCT GGA CCT TGG GGA GCC CCT CAG GGA CCC CTT CCC CAC CTC         291
Glu Val Ala Gly Pro Trp Gly Ala Pro Gln Gly Pro Leu Pro His Leu
         75                  80                  85

ATT TAC CGG ACC CCT CTC CTC CCA GAT CCC CTC GGA TGC AGG GAA CCA         339
Ile Tyr Arg Thr Pro Leu Leu Pro Asp Pro Leu Gly Cys Arg Glu Pro
     90                  95                  100

GGC TGC CTG TTT GCT GTG CCT GCC CAG TCG GCT CCT CCA AAC CGG CCG         387
Gly Cys Leu Phe Ala Val Pro Ala Gln Ser Ala Pro Pro Asn Arg Pro
105              110                 115                     120

AGG CTG AGA AGG AAA AGG CAG GTC CGC CGG GGC CAC CCT ACA GTG CAC         435
Arg Leu Arg Arg Lys Arg Gln Val Arg Arg Gly His Pro Thr Val His
                 125                 130                 135

AGT GAA ACC AAG TAT GTG GAG CTA ATT GTG ATC AAC GAC CAC CAG CTG         483
Ser Glu Thr Lys Tyr Val Glu Leu Ile Val Ile Asn Asp His Gln Leu
             140                 145                 150

TTC GAG CAG ATG CGA CAG TCG GTG GTC CTC ACC AGC AAC TTT GCC AAG         531
Phe Glu Gln Met Arg Gln Ser Val Val Leu Thr Ser Asn Phe Ala Lys
         155                 160                 165

TCC GTG GTG AAC CTG GCC GAT GTG ATA TAC AAG GAG CAG CTC AAC ACT         579
Ser Val Val Asn Leu Ala Asp Val Ile Tyr Lys Glu Gln Leu Asn Thr
     170                 175                 180

CGC ATC GTC CTG GTT GCC ATG GAA ACA TGG GCA GAT GGG GAC AAG ATC         627
Arg Ile Val Leu Val Ala Met Glu Thr Trp Ala Asp Gly Asp Lys Ile
185                 190                 195                 200

CAG GTG CAG GAT GAC CTC CTG GAG ACC CTG GCC CGG CTC ATG GTC TAC         675
Gln Val Gln Asp Asp Leu Leu Glu Thr Leu Ala Arg Leu Met Val Tyr
                 205                 210                 215

CGA CGG GAG GGT CTG CCT GAG CCC AGT AAT GCC ACC CAC CTC TTC TCG         723
Arg Arg Glu Gly Leu Pro Glu Pro Ser Asn Ala Thr His Leu Phe Ser
             220                 225                 230

GGC AGG ACC TTC CAG AGC ACG AGC AGC GGG GCA GCC TAC GTG GGG GGC         771
Gly Arg Thr Phe Gln Ser Thr Ser Ser Gly Ala Ala Tyr Val Gly Gly
         235                 240                 245

ATA TGC TCC CTG TCC CAT GGC GGG GGT GTG AAC GAG TAC GGC AAC ATG         819
Ile Cys Ser Leu Ser His Gly Gly Gly Val Asn Glu Tyr Gly Asn Met
     250                 255                 260

GGG GCG ATG GCC GTG ACC CTT GCC CAG ACG CTG GGA CAG AAC CTG GGC         867
Gly Ala Met Ala Val Thr Leu Ala Gln Thr Leu Gly Gln Asn Leu Gly
265                 270                 275                 280
```

-continued

| | | | | | | | | | | | | | | | | |
|---|---|---|---|---|---|---|---|---|---|---|---|---|---|---|---|---|
| ATG | ATG | TGG | AAC | AAA | CAC | CGG | AGC | TCG | GCA | GGG | GAC | TGC | AAG | TGT | CCA | 915 |
| Met | Met | Trp | Asn | Lys 285 | His | Arg | Ser | Ser | Ala 290 | Gly | Asp | Cys | Lys | Cys 295 | Pro | |
| GAC | ATC | TGG | CTG | GGC | TGC | ATC | ATG | GAG | GAC | ACT | GGG | TTC | TAC | CTG | CCC | 963 |
| Asp | Ile | Trp | Leu 300 | Gly | Cys | Ile | Met | Glu 305 | Asp | Thr | Gly | Phe | Tyr 310 | Leu | Pro | |
| CGC | AAG | TTC | TCT | CGC | TGC | AGC | ATC | GAC | GAG | TAC | AAC | CAG | TTT | CTG | CAG | 1011 |
| Arg | Lys | Phe 315 | Ser | Arg | Cys | Ser | Ile 320 | Asp | Glu | Tyr | Asn | Gln 325 | Phe | Leu | Gln | |
| GAG | GGT | GGT | GGC | AGC | TGC | CTC | TTC | AAC | AAG | CCC | CTC | AAG | CTC | CTG | GAC | 1059 |
| Glu | Gly 330 | Gly | Gly | Ser | Cys | Leu 335 | Phe | Asn | Lys | Pro | Leu 340 | Lys | Leu | Leu | Asp | |
| CCC | CCA | GAG | TGC | GGG | AAC | GGC | TTC | GTG | GAG | GCA | GGG | GAG | GAG | TGC | GAC | 1107 |
| Pro 345 | Pro | Glu | Cys | Gly | Asn 350 | Gly | Phe | Val | Glu | Ala 355 | Gly | Glu | Glu | Cys | Asp 360 | |
| TGC | GGC | TCG | GTG | CAG | GAG | TGC | AGC | CGC | GCA | GGT | GGC | AAC | TGC | TGC | AAG | 1155 |
| Cys | Gly | Ser | Val | Gln 365 | Glu | Cys | Ser | Arg | Ala 370 | Gly | Gly | Asn | Cys | Cys 375 | Lys | |
| AAA | TGC | ACC | CTG | ACT | CAC | GAC | GCC | ATG | TGC | AGC | GAC | GGG | CTC | TGC | TGT | 1203 |
| Lys | Cys | Thr | Leu 380 | Thr | His | Asp | Ala | Met 385 | Cys | Ser | Asp | Gly | Leu 390 | Cys | Cys | |
| CGC | CGC | TGC | AAG | TAC | GAA | CCA | CGG | GGT | GTG | TCC | TGC | CGA | GAG | GCC | GTG | 1251 |
| Arg | Arg | Cys 395 | Lys | Tyr | Glu | Pro | Arg 400 | Gly | Val | Ser | Cys | Arg 405 | Glu | Ala | Val | |
| AAC | GAG | TGC | GAC | ATC | GCG | GAG | ACC | TGC | ACC | GGG | GAC | TCT | AGC | CAG | TGC | 1299 |
| Asn | Glu | Cys | Asp 410 | Ile | Ala | Glu | Thr | Cys 415 | Thr | Gly | Asp | Ser | Ser 420 | Gln | Cys | |
| CCG | CCT | AAC | CTG | CAC | AAG | CTG | GAC | GGT | TAC | TAC | TGT | GAC | CAT | GAG | CAG | 1347 |
| Pro 425 | Pro | Asn | Leu | His | Lys 430 | Leu | Asp | Gly | Tyr | Tyr 435 | Cys | Asp | His | Glu | Gln 440 | |
| GGC | CGC | TGC | TAC | GGA | GGT | CGC | TGC | AAA | ACC | CGG | GAC | CGG | CAG | TGC | CAG | 1395 |
| Gly | Arg | Cys | Tyr | Gly 445 | Gly | Arg | Cys | Lys | Thr 450 | Arg | Asp | Arg | Gln | Cys 455 | Gln | |
| GTT | CTT | TGG | GGC | CAT | GCG | GCT | GCT | GAT | CGC | TTC | TGC | TAC | GAG | AAG | CTG | 1443 |
| Val | Leu | Trp | Gly 460 | His | Ala | Ala | Ala | Asp 465 | Arg | Phe | Cys | Tyr | Glu 470 | Lys | Leu | |
| AAT | GTG | GAG | GGG | ACG | GAG | CGT | GGG | AGC | TGT | GGG | CGC | AAG | GGA | TCC | GGC | 1491 |
| Asn | Val | Glu 475 | Gly | Thr | Glu | Arg | Gly 480 | Ser | Cys | Gly | Arg | Lys 485 | Gly | Ser | Gly | |
| TGG | GTC | CAG | TGC | AGT | AAG | CAG | CCC | CAA | CAG | GGA | CGT | GCT | GTG | TGG | CTT | 1539 |
| Trp | Val | Gln 490 | Cys | Ser | Lys | Gln | Pro 495 | Gln | Gln | Gly | Arg | Ala 500 | Val | Trp | Leu | |
| CCT | CCT | CTG | TGT | CAA | CAT | CTC | TGG | AGC | TCC | TCG | GCT | AGG | GGA | CCT | GGT | 1587 |
| Pro 505 | Pro | Leu | Cys | Gln | His 510 | Leu | Trp | Ser | Ser | Ser 515 | Ala | Arg | Gly | Pro | Gly 520 | |
| GGG | AGA | CAT | CAG | TAGTGTCACC | TTCTACCACC | AGGGCAAGGA | GCTGGACTGC | | | | | | | | | 1639 |
| Gly | Arg | His | Gln 524 | | | | | | | | | | | | | |

| | | | | | |
|---|---|---|---|---|---|
| AGGGGAGGCC | ACGTGCAGCT | GGCGGACGGC | TCTGACCTGA | GCTATGTGGA | GGATGGCACA | 1699 |
| GCCTGCGGGC | CTAACATGTT | GTGCCTGGAC | CATCGCTGCC | TGCCAGCTTC | TGCCTTCAAC | 1759 |
| TTCAGCACCT | GCCCCGGCAG | TGGGGAGCGC | CGGATTTGCT | CCCACCACGG | GGTCTGCAGC | 1819 |
| AATGAAGGGA | AGTGCATCTG | TCAGCCAGAC | TGGACAGGCA | AGACTGCAG | TATCCATAAC | 1879 |
| CCCCTGCCCA | CGTCCCCACC | CACGGGGGAG | ACGGAGAGAT | ATAAAGGTCC | CAGCGGCACC | 1939 |
| AACATCATCA | TTGGCTCCAT | CGCTGGGGCT | GTCCTGGTTG | CAGCCATCGT | CCTGGGCGGC | 1999 |
| ACGGGCTGGG | GATTTAAAAA | CATTCGCCGA | GGAAGGTCCG | GAGGGGCCTA | AGTGCCACCC | 2059 |
| TCCTCCCTCC | AAGCCTGGCA | CCCACCGTCT | CGGCCCTGAA | CCACGAGGCT | GCCCCCATCC | 2119 |

```
AGCCACGGAG  GGAGGCACCA  TGCAAATGTC  TTCCAGGTCC  AAACCCTTCA  ACTCCTGGCT    2179

CCGCAGGGGT  TTGGGTGGGG  GCTGTGGCCC  TGCCCTTGGC  ACCACCAGGG  TGGACCAGGC    2239

CTGGAGGGCA  CTTCCTCCAC  AGTCCCCCAC  CCACCTCCTG  CGGCTCAGCC  TTGCACACCC    2299

ACTGCCCCGT  GTGAATGTAG  CTTCCACCTC  ATGGATTGCC  ACAGCTCAAC  TCGGGGGCAC    2359

CTGGAGGGAT  GCCCCCAGGC  AGCCACCAGT  GGACCTAGCC  TGGATGGCCC  CTCCTTGCAA    2419

CCAGGCAGCT  GAGACCAGGG  TCTTATCTCT  CTGGGACCTA  GGGGACGGG   GCTGACATCT    2479

ACATTTTTA   AAACTGAATC  TTAATCGATG  AATGTAAACT  CGGGGGTGCT  GGGGCCAGGG    2539

CAGATGTGGG  GATGTTTTGA  CATTTACAGG  AGGCCCCGGA  GAAACTGAGG  TATGGCCATG    2599

CCCTAGACCC  TCCCCAAGGA  TGACCACACC  CGAAGTCCTG  TCACTGAGCA  CAGTCAGGGG    2659

CTGGGCATCC  CAGCTTGCCC  CCGCTTAGCC  CCGCTGAGCT  TGGAGGAAGT  ATGAGTGCTG    2719

ATTCAAACCA  AAGCTGCCTG  TGCCATGCCC  AAGGCCTAGG  TTATGGGTAC  GGCAACCACA    2779

TGTCCCAGAT  CGTCTCCAAT  TCGAAAACAA  CCGTCCTGCT  GTCCCTGTCA  GGACACATGG    2839

ATTTTGGCAG  GGCGGGGGGG  GGTTCTAGAA  AATATAGGTT  CCTATAATAA  AATGGCACCT    2899

TCCCCCTTTA  AAAAAAAAA   AAAA                                             2923
```

( 2 ) INFORMATION FOR SEQ ID NO: 7:

( i ) SEQUENCE CHARACTERISTICS:
        ( A ) LENGTH: 2913 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: Homo sapiens ( v i i ) IMMEDIATE SOURCE:
        ( A ) LIBRARY: human fetal brain cDNA library ( i x ) FEATURE:
        ( A ) NAME/KEY: 5'UTR
        ( B ) LOCATION: 1..27

( i x ) FEATURE:
        ( A ) NAME/KEY: 3'UTR
        ( B ) LOCATION: 2038..2913

( i x ) FEATURE:
        ( A ) NAME/KEY: CDS
        ( B ) LOCATION: 28..2037

( x i ) SEQUENCE DESCRIPTION: SEQ ID NO: 7:

```
GCGTTTACTG  GCAAACCGCA  TTTGTAA  ATG  TGC  TGG  CTG  AGC  CAC  CAA  CTC           51
                                Met  Cys  Trp  Leu  Ser  His  Gln  Leu
                                 1                   5

CTC  TCC  TCG  CAA  TAC  GTG  GAG  CGC  CAC  TTC  AGC  CGG  GAG  GGG  ACA  ACC    99
Leu  Ser  Ser  Gln  Tyr  Val  Glu  Arg  His  Phe  Ser  Arg  Glu  Gly  Thr  Thr
      10                  15                       20

CAG  CAC  AGC  ACC  GGG  GCT  GGA  GAC  CAC  TGC  TAC  TAC  CAG  GGG  AAG  CTC   147
Gln  His  Ser  Thr  Gly  Ala  Gly  Asp  His  Cys  Tyr  Tyr  Gln  Gly  Lys  Leu
 25                   30                       35                        40

CGG  GGG  AAC  CCG  CAC  TCC  TTC  GCC  GCC  CTC  TCC  ACC  TGC  CAG  GGG  CTG   195
Arg  Gly  Asn  Pro  His  Ser  Phe  Ala  Ala  Leu  Ser  Thr  Cys  Gln  Gly  Leu
                    45                        50                    55

CAT  GGG  GTC  TTC  TCT  GAT  GGG  AAC  TTG  ACT  TAC  ATC  GTG  GAG  CCC  CAA   243
His  Gly  Val  Phe  Ser  Asp  Gly  Asn  Leu  Thr  Tyr  Ile  Val  Glu  Pro  Gln
               60                       65                    70
```

| | | | | | | | | | | | | | | | | |
|---|---|---|---|---|---|---|---|---|---|---|---|---|---|---|---|---|
| GAG | GTG | GCT | GGA | CCT | TGG | GGA | GCC | CCT | CAG | GGA | CCC | CTT | CCC | CAC | CTC | 291 |
| Glu | Val | Ala | Gly | Pro | Trp | Gly | Ala | Pro | Gln | Gly | Pro | Leu | Pro | His | Leu | |
| | | 75 | | | | | 80 | | | | | 85 | | | | |
| ATT | TAC | CGG | ACC | CCT | CTC | CTC | CCA | GAT | CCC | CTC | GGA | TGC | AGG | GAA | CCA | 339 |
| Ile | Tyr | Arg | Thr | Pro | Leu | Leu | Pro | Asp | Pro | Leu | Gly | Cys | Arg | Glu | Pro | |
| | | 90 | | | | | 95 | | | | | 100 | | | | |
| GGC | TGC | CTG | TTT | GCT | GTG | CCT | GCC | CAG | TCG | GCT | CCT | CCA | AAC | CGG | CCG | 387 |
| Gly | Cys | Leu | Phe | Ala | Val | Pro | Ala | Gln | Ser | Ala | Pro | Pro | Asn | Arg | Pro | |
| 105 | | | | | 110 | | | | | 115 | | | | | 120 | |
| AGG | CTG | AGA | AGG | AAA | AGG | CAG | GTC | CGC | CGG | GGC | CAC | CCT | ACA | GTG | CAC | 435 |
| Arg | Leu | Arg | Arg | Lys | Arg | Gln | Val | Arg | Arg | Gly | His | Pro | Thr | Val | His | |
| | | | | 125 | | | | | 130 | | | | | 135 | | |
| AGT | GAA | ACC | AAG | TAT | GTG | GAG | CTA | ATT | GTG | ATC | AAC | GAC | CAC | CAG | CTG | 483 |
| Ser | Glu | Thr | Lys | Tyr | Val | Glu | Leu | Ile | Val | Ile | Asn | Asp | His | Gln | Leu | |
| | | | 140 | | | | | 145 | | | | | 150 | | | |
| TTC | GAG | CAG | ATG | CGA | CAG | TCG | GTG | GTC | CTC | ACC | AGC | AAC | TTT | GCC | AAG | 531 |
| Phe | Glu | Gln | Met | Arg | Gln | Ser | Val | Val | Leu | Thr | Ser | Asn | Phe | Ala | Lys | |
| | | | 155 | | | | | 160 | | | | | 165 | | | |
| TCC | GTG | GTG | AAC | CTG | GCC | GAT | GTG | ATA | TAC | AAG | GAG | CAG | CTC | AAC | ACT | 579 |
| Ser | Val | Val | Asn | Leu | Ala | Asp | Val | Ile | Tyr | Lys | Glu | Gln | Leu | Asn | Thr | |
| | 170 | | | | | 175 | | | | | 180 | | | | | |
| CGC | ATC | GTC | CTG | GTT | GCC | ATG | GAA | ACA | TGG | GCA | GAT | GGG | GAC | AAG | ATC | 627 |
| Arg | Ile | Val | Leu | Val | Ala | Met | Glu | Thr | Trp | Ala | Asp | Gly | Asp | Lys | Ile | |
| 185 | | | | | 190 | | | | | 195 | | | | | 200 | |
| CAG | GTG | CAG | GAT | GAC | CTC | CTG | GAG | ACC | CTG | GCC | CGG | CTC | ATG | GTC | TAC | 675 |
| Gln | Val | Gln | Asp | Asp | Leu | Leu | Glu | Thr | Leu | Ala | Arg | Leu | Met | Val | Tyr | |
| | | | | 205 | | | | | 210 | | | | | 215 | | |
| CGA | CGG | GAG | GGT | CTG | CCT | GAG | CCC | AGT | AAT | GCC | ACC | CAC | CTC | TTC | TCG | 723 |
| Arg | Arg | Glu | Gly | Leu | Pro | Glu | Pro | Ser | Asn | Ala | Thr | His | Leu | Phe | Ser | |
| | | | 220 | | | | | 225 | | | | | 230 | | | |
| GGC | AGG | ACC | TTC | CAG | AGC | ACG | AGC | AGC | GGG | GCA | GCC | TAC | GTG | GGG | GGC | 771 |
| Gly | Arg | Thr | Phe | Gln | Ser | Thr | Ser | Ser | Gly | Ala | Ala | Tyr | Val | Gly | Gly | |
| | | 235 | | | | | 240 | | | | | 245 | | | | |
| ATA | TGC | TCC | CTG | TCC | CAT | GGC | GGG | GGT | GTG | AAC | GAG | TAC | GGC | AAC | ATG | 819 |
| Ile | Cys | Ser | Leu | Ser | His | Gly | Gly | Gly | Val | Asn | Glu | Tyr | Gly | Asn | Met | |
| | 250 | | | | | 255 | | | | | 260 | | | | | |
| GGG | GCG | ATG | GCC | GTG | ACC | CTT | GCC | CAG | ACG | CTG | GGA | CAG | AAC | CTG | GGC | 867 |
| Gly | Ala | Met | Ala | Val | Thr | Leu | Ala | Gln | Thr | Leu | Gly | Gln | Asn | Leu | Gly | |
| 265 | | | | | 270 | | | | | 275 | | | | | 280 | |
| ATG | ATG | TGG | AAC | AAA | CAC | CGG | AGC | TCG | GCA | GGG | GAC | TGC | AAG | TGT | CCA | 915 |
| Met | Met | Trp | Asn | Lys | His | Arg | Ser | Ser | Ala | Gly | Asp | Cys | Lys | Cys | Pro | |
| | | | | 285 | | | | | 290 | | | | | 295 | | |
| GAC | ATC | TGG | CTG | GGC | TGC | ATC | ATG | GAG | GAC | ACT | GGG | TTC | TAC | CTG | CCC | 963 |
| Asp | Ile | Trp | Leu | Gly | Cys | Ile | Met | Glu | Asp | Thr | Gly | Phe | Tyr | Leu | Pro | |
| | | | 300 | | | | | 305 | | | | | 310 | | | |
| CGC | AAG | TTC | TCT | CGC | TGC | AGC | ATC | GAC | GAG | TAC | AAC | CAG | TTT | CTG | CAG | 1011 |
| Arg | Lys | Phe | Ser | Arg | Cys | Ser | Ile | Asp | Glu | Tyr | Asn | Gln | Phe | Leu | Gln | |
| | | 315 | | | | | 320 | | | | | 325 | | | | |
| GAG | GGT | GGT | GGC | AGC | TGC | CTC | TTC | AAC | AAG | CCC | CTC | AAG | CTC | CTG | GAC | 1059 |
| Glu | Gly | Gly | Gly | Ser | Cys | Leu | Phe | Asn | Lys | Pro | Leu | Lys | Leu | Leu | Asp | |
| | 330 | | | | | 335 | | | | | 340 | | | | | |
| CCC | CCA | GAG | TGC | GGG | AAC | GGC | TTC | GTG | GAG | GCA | GGG | GAG | GAG | TGC | GAC | 1107 |
| Pro | Pro | Glu | Cys | Gly | Asn | Gly | Phe | Val | Glu | Ala | Gly | Glu | Glu | Cys | Asp | |
| 345 | | | | | 350 | | | | | 355 | | | | | 360 | |
| TGC | GGC | TCG | GTG | CAG | GAG | TGC | AGC | CGC | GCA | GGT | GGC | AAC | TGC | TGC | AAG | 1155 |
| Cys | Gly | Ser | Val | Gln | Glu | Cys | Ser | Arg | Ala | Gly | Gly | Asn | Cys | Cys | Lys | |
| | | | | 365 | | | | | 370 | | | | | 375 | | |
| AAA | TGC | ACC | CTG | ACT | CAC | GAC | GCC | ATG | TGC | AGC | GAC | GGG | CTC | TGC | TGT | 1203 |
| Lys | Cys | Thr | Leu | Thr | His | Asp | Ala | Met | Cys | Ser | Asp | Gly | Leu | Cys | Cys | |
| | | | 380 | | | | | 385 | | | | | 390 | | | |

| | | | | | | | | | | | | | | | | |
|---|---|---|---|---|---|---|---|---|---|---|---|---|---|---|---|---|
| CGC | CGC | TGC | AAG | TAC | GAA | CCA | CGG | GGT | GTG | TCC | TGC | CGA | GAG | GCC | GTG | 1251 |
| Arg | Arg | Cys | Lys | Tyr | Glu | Pro | Arg | Gly | Val | Ser | Cys | Arg | Glu | Ala | Val | |
| | | 395 | | | | 400 | | | | | | 405 | | | | |
| AAC | GAG | TGC | GAC | ATC | GCG | GAG | ACC | TGC | ACC | GGG | GAC | TCT | AGC | CAG | TGC | 1299 |
| Asn | Glu | Cys | Asp | Ile | Ala | Glu | Thr | Cys | Thr | Gly | Asp | Ser | Ser | Gln | Cys | |
| | 410 | | | | | 415 | | | | | 420 | | | | | |
| CCG | CCT | AAC | CTG | CAC | AAG | CTG | GAC | GGT | TAC | TAC | TGT | GAC | CAT | GAG | CAG | 1347 |
| Pro | Pro | Asn | Leu | His | Lys | Leu | Asp | Gly | Tyr | Tyr | Cys | Asp | His | Glu | Gln | |
| 425 | | | | | 430 | | | | | 435 | | | | | 440 | |
| GGC | CGC | TGC | TAC | GGA | GGT | CGC | TGC | AAA | ACC | CGG | GAC | CGG | CAG | TGC | CAG | 1395 |
| Gly | Arg | Cys | Tyr | Gly | Gly | Arg | Cys | Lys | Thr | Arg | Asp | Arg | Gln | Cys | Gln | |
| | | | | 445 | | | | | 450 | | | | | 455 | | |
| GTT | CTT | TGG | GGC | CAT | GCG | GCT | GCT | GAT | CGC | TTC | TGC | TAC | GAG | AAG | CTG | 1443 |
| Val | Leu | Trp | Gly | His | Ala | Ala | Ala | Asp | Arg | Phe | Cys | Tyr | Glu | Lys | Leu | |
| | | | | 460 | | | | 465 | | | | | 470 | | | |
| AAT | GTG | GAG | GGG | ACG | GAG | CGT | GGG | AGC | TGT | GGG | CGC | AAG | GGA | TCC | GGC | 1491 |
| Asn | Val | Glu | Gly | Thr | Glu | Arg | Gly | Ser | Cys | Gly | Arg | Lys | Gly | Ser | Gly | |
| | | 475 | | | | | 480 | | | | | 485 | | | | |
| TGG | GTC | CAG | TGC | AGT | AAG | CAG | GAC | GTG | CTG | TGT | GGC | TTC | CTC | CTC | TGT | 1539 |
| Trp | Val | Gln | Cys | Ser | Lys | Gln | Asp | Val | Leu | Cys | Gly | Phe | Leu | Leu | Cys | |
| | 490 | | | | | 495 | | | | | 500 | | | | | |
| GTC | AAC | ATC | TCT | GGA | GCT | CCT | CGG | CTA | GGG | GAC | CTG | GTG | GGA | GAC | ATC | 1587 |
| Val | Asn | Ile | Ser | Gly | Ala | Pro | Arg | Leu | Gly | Asp | Leu | Val | Gly | Asp | Ile | |
| 505 | | | | | 510 | | | | | 515 | | | | | 520 | |
| AGT | AGT | GTC | ACC | TTC | TAC | CAC | CAG | GGC | AAG | GAG | CTG | GAC | TGC | AGG | GGA | 1635 |
| Ser | Ser | Val | Thr | Phe | Tyr | His | Gln | Gly | Lys | Glu | Leu | Asp | Cys | Arg | Gly | |
| | | | | 525 | | | | | 530 | | | | | 535 | | |
| GGC | CAC | GTG | CAG | CTG | GCG | GAC | GGC | TCT | GAC | CTG | AGC | TAT | GTG | GAG | GAT | 1683 |
| Gly | His | Val | Gln | Leu | Ala | Asp | Gly | Ser | Asp | Leu | Ser | Tyr | Val | Glu | Asp | |
| | | | 540 | | | | | 545 | | | | | 550 | | | |
| GGC | ACA | GCC | TGC | GGG | CCT | AAC | ATG | TTG | TGC | CTG | GAC | CAT | CGC | TGC | CTG | 1731 |
| Gly | Thr | Ala | Cys | Gly | Pro | Asn | Met | Leu | Cys | Leu | Asp | His | Arg | Cys | Leu | |
| | | 555 | | | | | 560 | | | | | 565 | | | | |
| CCA | GCT | TCT | GCC | TTC | AAC | TTC | AGC | ACC | TGC | CCC | GGC | AGT | GGG | GAG | CGC | 1779 |
| Pro | Ala | Ser | Ala | Phe | Asn | Phe | Ser | Thr | Cys | Pro | Gly | Ser | Gly | Glu | Arg | |
| | 570 | | | | | 575 | | | | | 580 | | | | | |
| CGG | ATT | TGC | TCC | CAC | CAC | GGG | GTC | TGC | AGC | AAT | GAA | GGG | AAG | TGC | ATC | 1827 |
| Arg | Ile | Cys | Ser | His | His | Gly | Val | Cys | Ser | Asn | Glu | Gly | Lys | Cys | Ile | |
| 585 | | | | | 590 | | | | | 595 | | | | | 600 | |
| TGT | CAG | CCA | GAC | TGG | ACA | GGC | AAA | GAC | TGC | AGT | ATC | CAT | AAC | CCC | CTG | 1875 |
| Cys | Gln | Pro | Asp | Trp | Thr | Gly | Lys | Asp | Cys | Ser | Ile | His | Asn | Pro | Leu | |
| | | | | 605 | | | | | 610 | | | | | 615 | | |
| CCC | ACG | TCC | CCA | CCC | ACG | GGG | GAG | ACG | GAG | AGA | TAT | AAA | GGT | CCC | AGC | 1923 |
| Pro | Thr | Ser | Pro | Pro | Thr | Gly | Glu | Thr | Glu | Arg | Tyr | Lys | Gly | Pro | Ser | |
| | | | 620 | | | | | 625 | | | | | 630 | | | |
| GGC | ACC | AAC | ATC | ATC | ATT | GGC | TCC | ATC | GCT | GGG | GCT | GTC | CTG | GTT | GCA | 1971 |
| Gly | Thr | Asn | Ile | Ile | Ile | Gly | Ser | Ile | Ala | Gly | Ala | Val | Leu | Val | Ala | |
| | | 635 | | | | | 640 | | | | | 645 | | | | |
| GCC | TAC | GTC | CTG | GGC | GGC | ACG | GGC | TGG | GGA | TTT | AAA | AAC | ATT | CGC | CGA | 2019 |
| Ala | Ile | Val | Leu | Gly | Gly | Thr | Gly | Trp | Gly | Phe | Lys | Asn | Ile | Arg | Arg | |
| | | 650 | | | | | 655 | | | | | 660 | | | | |
| GGA | AGG | TCC | GGA | GGG | GCC | TAAGTGCCAC | CCTCCTCCCT | CCAAGCCTGG | | | | | | | | 2067 |
| Gly | Arg | Ser | Gly | Gly | Ala | | | | | | | | | | | |
| 665 | | | | | 670 | | | | | | | | | | | |

```
CACCCACCGT CTCGGCCCTG AACCACGAGG CTGCCCCCAT CCAGCCACGG AGGGAGGCAC    2127

CATGCAAATG TCTTCCAGGT CCAAACCCTT CAACTCCTGG CTCCGCAGGG GTTTGGGTGG    2187

GGGCTGTGGC CCTGCCCTTG GCACCACCAG GGTGGACCAG GCCTGGAGGG CACTTCCTCC    2247

ACAGTCCCCC ACCCACCTCC TGCGGCTCAG CCTTGCACAC CCACTGCCCC GTGTGAATGT    2307
```

```
AGCTTCCACC TCATGGATTG CCACAGCTCA ACTCGGGGGC ACCTGGAGGG ATGCCCCCAG    2367

GCAGCCACCA GTGGACCTAG CCTGGATGGC CCCTCCTTGC AACCAGGCAG CTGAGACCAG    2427

GGTCTTATCT CTCTGGGACC TAGGGGGACG GGGCTGACAT CTACATTTTT TAAAACTGAA    2487

TCTTAATCGA TGAATGTAAA CTCGGGGGTG CTGGGCCAG  GGCAGATGTG GGGATGTTTT    2547

GACATTTACA GGAGGCCCCG GAGAAACTGA GGTATGGCCA TGCCCTAGAC CCTCCCCAAG    2607

GATGACCACA CCCGAAGTCC TGTCACTGAG CACAGTCAGG GCTGGGCAT  CCCAGCTTGC    2667

CCCCGCTTAG CCCCGCTGAG CTTGGAGGAA GTATGAGTGC TGATTCAAAC CAAAGCTGCC    2727

TGTGCCATGC CCAAGGCCTA GGTTATGGGT ACGGCAACCA CATGTCCCAG ATCGTCTCCA    2787

ATTCGAAAAC AACCGTCCTG CTGTCCCTGT CAGGACACAT GGATTTGGC  AGGGCGGGGG    2847

GGGGTTCTAG AAAATATAGG TTCCTATAAT AAAATGGCAC CTTCCCCCTT TAAAAAAAA    2907

AAAAAA                                                              2913
```

(2) INFORMATION FOR SEQ ID NO: 8:

(i) SEQUENCE CHARACTERISTICS:
        (A) LENGTH: 3183 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: Homo sapiens (vii) IMMEDIATE SOURCE:
        (A) LIBRARY: human fetal brain cDNA library (ix) FEATURE:
        (A) NAME/KEY: 3'UTR
        (B) LOCATION: 2308..3183

(ix) FEATURE:
        (A) NAME/KEY: CDS
        (B) LOCATION: 1..2307

(xi) SEQUENCE DESCRIPTION: SEQ ID NO: 8:

```
ATG AGG CTG CTG CGG CGC TGG GCG TTC GCG GCT CTG CTG CTG TCG CTG     48
Met Arg Leu Leu Arg Arg Trp Ala Phe Ala Ala Leu Leu Leu Ser Leu
 1               5                  10                  15

CTC CCC ACG CCC GGT CTT GGG ACC CAA GGT CCT GCT GGA GCT CTG CGA     96
Leu Pro Thr Pro Gly Leu Gly Thr Gln Gly Pro Ala Gly Ala Leu Arg
             20                  25                  30

TGG GGG GGC TTA CCC CAG CTG GGA GGC CCA GGA GCC CCT GAG GTC ACG    144
Trp Gly Gly Leu Pro Gln Leu Gly Gly Pro Gly Ala Pro Glu Val Thr
         35                  40                  45

GAA CCC AGC CGT CTG GTT AGG GAG AGC TCC GGG GGA GAG GTC CGA AAG    192
Glu Pro Ser Arg Leu Val Arg Glu Ser Ser Gly Gly Glu Val Arg Lys
     50                  55                  60

CAG CAG CTG GAC ACA AGG GTC CGC CAG GAG CCA CCA GGG GGC CCG CCT    240
Gln Gln Leu Asp Thr Arg Val Arg Gln Glu Pro Pro Gly Gly Pro Pro
 65                  70                  75                  80

GTC CAT CTG GCC CAG GTG AGT TTC GTC ATC CCA GCC TTC AAC TCA AAC    288
Val His Leu Ala Gln Val Ser Phe Val Ile Pro Ala Phe Asn Ser Asn
                 85                  90                  95

TTC ACC CTG GAC CTG GAG CTG AAC CAC CAC CTC CTC TCC TCG CAA TAC    336
Phe Thr Leu Asp Leu Glu Leu Asn His His Leu Leu Ser Ser Gln Tyr
            100                 105                 110

GTG GAG CGC CAC TTC AGC CGG GAG GGG ACA ACC CAG CAC AGC ACC GGG    384
Val Glu Arg His Phe Ser Arg Glu Gly Thr Thr Gln His Ser Thr Gly
        115                 120                 125
```

```
GCT GGA GAC CAC TGC TAC TAC CAG GGG AAG CTC CGG GGG AAC CCG CAC        432
Ala Gly Asp His Cys Tyr Tyr Gln Gly Lys Leu Arg Gly Asn Pro His
130             135                     140

TCC TTC GCC GCC CTC TCC ACC TGC CAG GGG CTG CAT GGG GTC TTC TCT        480
Ser Phe Ala Ala Leu Ser Thr Cys Gln Gly Leu His Gly Val Phe Ser
145             150                     155                     160

GAT GGG AAC TTG ACT TAC ATC GTG GAG CCC CAA GAG GTG GCT GGA CCT        528
Asp Gly Asn Leu Thr Tyr Ile Val Glu Pro Gln Glu Val Ala Gly Pro
                165                     170                     175

TGG GGA GCC CCT CAG GGA CCC CTT CCC CAC CTC ATT TAC CGG ACC CCT        576
Trp Gly Ala Pro Gln Gly Pro Leu Pro His Leu Ile Tyr Arg Thr Pro
        180                     185                     190

CTC CTC CCA GAT CCC CTC GGA TGC AGG GAA CCA GGC TGC CTG TTT GCT        624
Leu Leu Pro Asp Pro Leu Gly Cys Arg Glu Pro Gly Cys Leu Phe Ala
            195                     200                     205

GTG CCT GCC CAG TCG GCT CCT CCA AAC CGG CCG AGG CTG AGA AGG AAA        672
Val Pro Ala Gln Ser Ala Pro Pro Asn Arg Pro Arg Leu Arg Arg Lys
        210                     215                     220

AGG CAG GTC CGC CGG GGC CAC CCT ACA GTG CAC AGT GAA ACC AAG TAT        720
Arg Gln Val Arg Arg Gly His Pro Thr Val His Ser Glu Thr Lys Tyr
225                     230                     235                 240

GTG GAG CTA ATT GTG ATC AAC GAC CAC CAG CTG TTC GAG CAG ATG CGA        768
Val Glu Leu Ile Val Ile Asn Asp His Gln Leu Phe Glu Gln Met Arg
                245                     250                     255

CAG TCG GTG GTC CTC ACC AGC AAC TTT GCC AAG TCC GTG GTG AAC CTG        816
Gln Ser Val Val Leu Thr Ser Asn Phe Ala Lys Ser Val Val Asn Leu
            260                     265                     270

GCC GAT GTG ATA TAC AAG GAG CAG CTC AAC ACT CGC ATC GTC CTG GTT        864
Ala Asp Val Ile Tyr Lys Glu Gln Leu Asn Thr Arg Ile Val Leu Val
        275                     280                     285

GCC ATG GAA ACA TGG GCA GAT GGG GAC AAG ATC CAG GTG CAG GAT GAC        912
Ala Met Glu Thr Trp Ala Asp Gly Asp Lys Ile Gln Val Gln Asp Asp
    290                     295                     300

CTC CTG GAG ACC CTG GCC CGG CTC ATG GTC TAC CGA CGG GAG GGT CTG        960
Leu Leu Glu Thr Leu Ala Arg Leu Met Val Tyr Arg Arg Glu Gly Leu
305                     310                     315                 320

CCT GAG CCC AGT AAT GCC ACC CAC CTC TTC TCG GGC AGG ACC TTC CAG       1008
Pro Glu Pro Ser Asn Ala Thr His Leu Phe Ser Gly Arg Thr Phe Gln
                325                     330                     335

AGC ACG AGC AGC GGG GCA GCC TAC GTG GGG GGC ATA TGC TCC CTG TCC       1056
Ser Thr Ser Ser Gly Ala Ala Tyr Val Gly Gly Ile Cys Ser Leu Ser
            340                     345                     350

CAT GGC GGG GGT GTG AAC GAG TAC GGC AAC ATG GGG GCG ATG GCC GTG       1104
His Gly Gly Gly Val Asn Glu Tyr Gly Asn Met Gly Ala Met Ala Val
        355                     360                     365

ACC CTT GCC CAG ACG CTG GGA CAG AAC CTG GGC ATG ATG TGG AAC AAA       1152
Thr Leu Ala Gln Thr Leu Gly Gln Asn Leu Gly Met Met Trp Asn Lys
370                     375                     380

CAC CGG AGC TCG GCA GGG GAC TGC AAG TGT CCA GAC ATC TGG CTG GGC       1200
His Arg Ser Ser Ala Gly Asp Cys Lys Cys Pro Asp Ile Trp Leu Gly
385                     390                     395                 400

TGC ATC ATG GAG GAC ACT GGG TTC TAC CTG CCC CGC AAG TTC TCT CGC       1248
Cys Ile Met Glu Asp Thr Gly Phe Tyr Leu Pro Arg Lys Phe Ser Arg
                405                     410                     415

TGC AGC ATC GAC GAG TAC AAC CAG TTT CTG CAG GAG GGT GGC GGC AGC       1296
Cys Ser Ile Asp Glu Tyr Asn Gln Phe Leu Gln Glu Gly Gly Gly Ser
            420                     425                     430

TGC CTC TTC AAC AAG CCC CTC AAG CTC CTG GAC CCC CCA GAG TGC GGG       1344
Cys Leu Phe Asn Lys Pro Leu Lys Leu Leu Asp Pro Pro Glu Cys Gly
        435                     440                     445
```

-continued

| | | | | | | | | | | | | | | | | |
|---|---|---|---|---|---|---|---|---|---|---|---|---|---|---|---|---|
| AAC | GGC | TTC | GTG | GAG | GCA | GGG | GAG | GAG | TGC | GAC | TGC | GGC | TCG | GTG | CAG | 1392 |
| Asn | Gly | Phe | Val | Glu | Ala | Gly | Glu | Glu | Cys | Asp | Cys | Gly | Ser | Val | Gln | |
| | 450 | | | | 455 | | | | | 460 | | | | | | |
| GAG | TGC | AGC | CGC | GCA | GGT | GGC | AAC | TGC | TGC | AAG | AAA | TGC | ACC | CTG | ACT | 1440 |
| Glu | Cys | Ser | Arg | Ala | Gly | Gly | Asn | Cys | Cys | Lys | Lys | Cys | Thr | Leu | Thr | |
| 465 | | | | | 470 | | | | | 475 | | | | | 480 | |
| CAC | GAC | GCC | ATG | TGC | AGC | GAC | GGG | CTC | TGC | TGT | CGC | CGC | TGC | AAG | TAC | 1488 |
| His | Asp | Ala | Met | Cys | Ser | Asp | Gly | Leu | Cys | Cys | Arg | Arg | Cys | Lys | Tyr | |
| | | | | 485 | | | | | 490 | | | | | 495 | | |
| GAA | CCA | CGG | GGT | GTG | TCC | TGC | CGA | GAG | GCC | GTG | AAC | GAG | TGC | GAC | ATC | 1536 |
| Glu | Pro | Arg | Gly | Val | Ser | Cys | Arg | Glu | Ala | Val | Asn | Glu | Cys | Asp | Ile | |
| | | | 500 | | | | 505 | | | | | 510 | | | | |
| GCG | GAG | ACC | TGC | ACC | GGG | GAC | TCT | AGC | CAG | TGC | CCG | CCT | AAC | CTG | CAC | 1584 |
| Ala | Glu | Thr | Cys | Thr | Gly | Asp | Ser | Ser | Gln | Cys | Pro | Pro | Asn | Leu | His | |
| | | 515 | | | | | 520 | | | | | 525 | | | | |
| AAG | CTG | GAC | GGT | TAC | TAC | TGT | GAC | CAT | GAG | CAG | GGC | CGC | TGC | TAC | GGA | 1632 |
| Lys | Leu | Asp | Gly | Tyr | Tyr | Cys | Asp | His | Glu | Gln | Gly | Arg | Cys | Tyr | Gly | |
| | 530 | | | | | 535 | | | | | 540 | | | | | |
| GGT | CGC | TGC | AAA | ACC | CGG | GAC | CGG | CAG | TGC | CAG | GTT | CTT | TGG | GGC | CAT | 1680 |
| Gly | Arg | Cys | Lys | Thr | Arg | Asp | Arg | Gln | Cys | Gln | Val | Leu | Trp | Gly | His | |
| 545 | | | | | 550 | | | | | 555 | | | | | 560 | |
| GCG | GCT | GCT | GAT | CGC | TTC | TGC | TAC | GAG | AAG | CTG | AAT | GTG | GAG | GGG | ACG | 1728 |
| Ala | Ala | Ala | Asp | Arg | Phe | Cys | Tyr | Glu | Lys | Leu | Asn | Val | Glu | Gly | Thr | |
| | | | | 565 | | | | | 570 | | | | | 575 | | |
| GAG | CGT | GGG | AGC | TGT | GGG | CGC | AAG | GGA | TCC | GGC | TGG | GTC | CAG | TGC | AGT | 1776 |
| Glu | Arg | Gly | Ser | Cys | Gly | Arg | Lys | Gly | Ser | Gly | Trp | Val | Gln | Cys | Ser | |
| | | | 580 | | | | 585 | | | | | 590 | | | | |
| AAG | CAG | GAC | GTG | CTG | TGT | GGC | TTC | CTC | CTC | TGT | GTC | AAC | ATC | TCT | GGA | 1824 |
| Lys | Gln | Asp | Val | Leu | Cys | Gly | Phe | Leu | Leu | Cys | Val | Asn | Ile | Ser | Gly | |
| | | 595 | | | | | 600 | | | | | 605 | | | | |
| GCT | CCT | CGG | CTA | GGG | GAC | CTG | GTG | GGA | GAC | ATC | AGT | AGT | GTC | ACC | TTC | 1872 |
| Ala | Pro | Arg | Leu | Gly | Asp | Leu | Val | Gly | Asp | Ile | Ser | Ser | Val | Thr | Phe | |
| | 610 | | | | | 615 | | | | | 620 | | | | | |
| TAC | CAC | CAG | GGC | AAG | GAG | CTG | GAC | TGC | AGG | GGA | GGC | CAC | GTG | CAG | CTG | 1920 |
| Tyr | His | Gln | Gly | Lys | Glu | Leu | Asp | Cys | Arg | Gly | Gly | His | Val | Gln | Leu | |
| 625 | | | | | 630 | | | | | 635 | | | | | 640 | |
| GCG | GAC | GGC | TCT | GAC | CTG | AGC | TAT | GTG | GAG | GAT | GGC | ACA | GCC | TGC | GGG | 1968 |
| Ala | Asp | Gly | Ser | Asp | Leu | Ser | Tyr | Val | Glu | Asp | Gly | Thr | Ala | Cys | Gly | |
| | | | | 645 | | | | | 650 | | | | | 655 | | |
| CCT | AAC | ATG | TTG | TGC | CTG | GAC | CAT | CGC | TGC | CTG | CCA | GCT | TCT | GCC | TTC | 2016 |
| Pro | Asn | Met | Leu | Cys | Leu | Asp | His | Arg | Cys | Leu | Pro | Ala | Ser | Ala | Phe | |
| | | | 660 | | | | 665 | | | | | 670 | | | | |
| AAC | TTC | AGC | ACC | TGC | CCC | GGC | AGT | GGG | GAG | CGC | CGG | ATT | TGC | TCC | CAC | 2064 |
| Asn | Phe | Ser | Thr | Cys | Pro | Gly | Ser | Gly | Glu | Arg | Arg | Ile | Cys | Ser | His | |
| | | 675 | | | | | 680 | | | | | 685 | | | | |
| CAC | GGG | GTC | TGC | AGC | AAT | GAA | GGG | AAG | TGC | ATC | TGT | CAG | CCA | GAC | TGG | 2112 |
| His | Gly | Val | Cys | Ser | Asn | Glu | Gly | Lys | Cys | Ile | Cys | Gln | Pro | Asp | Trp | |
| | 690 | | | | | 695 | | | | | 700 | | | | | |
| ACA | GGC | AAA | GAC | TGC | AGT | ATC | CAT | AAC | CCC | CTG | CCC | ACG | TCC | CCA | CCC | 2160 |
| Thr | Gly | Lys | Asp | Cys | Ser | Ile | His | Asn | Pro | Leu | Pro | Thr | Ser | Pro | Pro | |
| 705 | | | | | 710 | | | | | 715 | | | | | 720 | |
| ACG | GGG | GAG | ACG | GAG | AGA | TAT | AAA | GGT | CCC | AGC | GGC | ACC | AAC | ATC | ATC | 2208 |
| Thr | Gly | Glu | Thr | Glu | Arg | Tyr | Lys | Gly | Pro | Ser | Gly | Thr | Asn | Ile | Ile | |
| | | | | 725 | | | | | 730 | | | | | 735 | | |
| ATT | GGC | TCC | ATC | GCT | GGG | GCT | GTC | CTG | GTT | GCA | GCC | ATC | GTC | CTG | GGC | 2256 |
| Ile | Gly | Ser | Ile | Ala | Gly | Ala | Val | Leu | Val | Ala | Ala | Ile | Val | Leu | Gly | |
| | | | | 740 | | | | | 745 | | | | | 750 | | |
| GGC | ACG | GGC | TGG | GGA | TTT | AAA | AAC | ATT | CGC | CGA | GGA | AGG | TCC | GGA | GGG | 2304 |
| Gly | Thr | Gly | Trp | Gly | Phe | Lys | Asn | Ile | Arg | Arg | Gly | Arg | Ser | Gly | Gly | |
| | 755 | | | | | 760 | | | | | 765 | | | | | |

```
GCC TAAGTGCCAC CCTCCTCCCT CCAAGCCTGG CACCCACCGT CTCGGCCCTG         2357
Ala
769

AACCACGAGG CTGCCCCCAT CCAGCCACGG AGGGAGGCAC CATGCAAATG TCTTCCAGGT  2417

CCAAACCCTT CAACTCCTGG CTCCGCAGGG GTTTGGGTGG GGGCTGTGGC CCTGCCCTTG  2477

GCACCACCAG GGTGGACCAG GCCTGGAGGG CACTTCCTCC ACAGTCCCCC ACCCACCTCC  2537

TGCGGCTCAG CCTTGCACAC CCACTGCCCC GTGTGAATGT AGCTTCCACC TCATGGATTG  2597

CCACAGCTCA ACTCGGGGGC ACCTGGAGGG ATGCCCCAG GCAGCCACCA GTGGACCTAG   2657

CCTGGATGGC CCCTCCTTGC AACCAGGCAG CTGAGACCAG GGTCTTATCT CTCTGGGACC  2717

TAGGGGACG GGGCTGACAT CTACATTTTT TAAAACTGAA TCTTAATCGA TGAATGTAAA   2777

CTCGGGGGTG CTGGGGCCAG GGCAGATGTG GGGATGTTTT GACATTTACA GGAGGCCCCG  2837

GAGAAACTGA GGTATGGCCA TGCCCTAGAC CCTCCCCAAG GATGACCACA CCCGAAGTCC  2897

TGTCACTGAG CACAGTCAGG GGCTGGGCAT CCCAGCTTGC CCCCGCTTAG CCCCGCTGAG  2957

CTTGGAGGAA GTATGAGTGC TGATTCAAAC CAAAGCTGCC TGTGCCATGC CCAAGGCCTA  3017

GGTTATGGGT ACGGCAACCA CATGTCCCAG ATCGTCTCCA ATTCGAAAAC AACCGTCCTG  3077

CTGTCCCTGT CAGGACACAT GGATTTTGGC AGGGCGGGGG GGGGTTCTAG AAAATATAGG  3137

TTCCTATAAT AAAATGGCAC CTTCCCCCTT TAAAAAAAAA AAAAAA                3183
```

( 2 ) INFORMATION FOR SEQ ID NO: 9:

( i ) SEQUENCE CHARACTERISTICS:
        ( A ) LENGTH: 9278 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Homo sapiens ( v i i ) IMMEDIATE SOURCE:
        ( A ) LIBRARY: human DNA cosmid library ( i x ) FEATURE:
        ( A ) NAME/KEY: exon 1
        ( B ) LOCATION: 28..44

( i x ) FEATURE:
        ( A ) NAME/KEY: exon 2
        ( B ) LOCATION: 308..374

( i x ) FEATURE:
        ( A ) NAME/KEY: exon 3
        ( B ) LOCATION: 909..994

( i x ) FEATURE:
        ( A ) NAME/KEY: exon 4
        ( B ) LOCATION: 1081..1156

( i x ) FEATURE:
        ( A ) NAME/KEY: exon 5
        ( B ) LOCATION: 1591..1657

( i x ) FEATURE:
        ( A ) NAME/KEY: exon 6
        ( B ) LOCATION: 1725..1792

( i x ) FEATURE:
        ( A ) NAME/KEY: exon 7
        ( B ) LOCATION: 2182..2256

( i x ) FEATURE:
        ( A ) NAME/KEY: exon 8

( B ) LOCATION: 2339..2410

( i x ) FEATURE:
                ( A ) NAME/KEY: exon 9
                ( B ) LOCATION: 2588..2754

( i x ) FEATURE:
                ( A ) NAME/KEY: exon 10
                ( B ) LOCATION: 3248..3332

( i x ) FEATURE:
                ( A ) NAME/KEY: exon 11
                ( B ) LOCATION: 3445..3535

( i x ) FEATURE:
                ( A ) NAME/KEY: exon 12
                ( B ) LOCATION: 3645..3696

( i x ) FEATURE:
                ( A ) NAME/KEY: exon 13
                ( B ) LOCATION: 4014..4113

( i x ) FEATURE:
                ( A ) NAME/KEY: exon 14
                ( B ) LOCATION: 4196..4267

( i x ) FEATURE:
                ( A ) NAME/KEY: exon 15
                ( B ) LOCATION: 4386..4478

( i x ) FEATURE:
                ( A ) NAME/KEY: exon 16
                ( B ) LOCATION: 4920..5000

( i x ) FEATURE:
                ( A ) NAME/KEY: exon 17
                ( B ) LOCATION: 5347..5397

( i x ) FEATURE:
                ( A ) NAME/KEY: exon 18
                ( B ) LOCATION: 5501..5564

( i x ) FEATURE:
                ( A ) NAME/KEY: exon 19
                ( B ) LOCATION: 5767..5866

( i x ) FEATURE:
                ( A ) NAME/KEY: exon 20
                ( B ) LOCATION: 6073..6202

( i x ) FEATURE:
                ( A ) NAME/KEY: exon 21
                ( B ) LOCATION: 6300..6468

( i x ) FEATURE:
                ( A ) NAME/KEY: exon 22
                ( B ) LOCATION: 6557..6671

( i x ) FEATURE:
                ( A ) NAME/KEY: exon 23
                ( B ) LOCATION: 6756..6846

( i x ) FEATURE:
                ( A ) NAME/KEY: exon 24
                ( B ) LOCATION: 7829..7846

( i x ) FEATURE:
                ( A ) NAME/KEY: exon 25
                ( B ) LOCATION: 8165..9038

( x i ) SEQUENCE DESCRIPTION: SEQ ID NO: 9:

```
GCGTTTACTG GCAAACCGCA TTTGTAA ATG TGC TGG CTG AGC CA NNNNNNNNN              54
                             Met Cys Trp Leu Ser His
                              1                   5

NNNNCCAGGT GAGTTTCGTC ATCCAGCCTT CAACTCAAAC TTCACCCTGG ACCTGGAGCT          114

GAACCAGTGA GNGTGGCCTT GAGCCCAAGA GGAAGGGCAG TGGTGGNNNG GGGGAGACAT          174
```

| | |
|---|---|
| GGCTAGGGCC TGGCTGCTGG GGGTCTGGGG GTTGGGCCTG GCGAGAGGGG ACCTGGGTCC | 234 |
| TGACCTGAGG CGAGCCTAAA GCCCGACCTC ACCTCGCCCG TGACCCCCCT TCCTGCTGCC | 294 |

CCCTCTGTCT CAG C CAA CTC CTC TCC TCG CAA TAC GTG GAG CGC CAC TTC    344
                     Gln Leu Leu Ser Ser Gln Tyr Val Glu Arg His Phe
                                10                         15

AGC CGG GAG GGG ACA ACC CAG CAC AGC ACC GTGAGTGCCA CTGCTGGGGA    394
Ser Arg Glu Gly Thr Thr Gln His Ser Thr
      20               25

| | |
|---|---|
| CCGGGGCCGG GGATGGAAGG GAGGTGCTGT TTCTGTGGTT CTGTGGTCAC AGGTGTAGGG | 454 |
| ACAGGTGGCC ACTGGAGATG GGGTCCTGGG CCTGGCCCCT CAGCACCTTC CCTCTCTCCC | 514 |
| GACCCAGGAG GCTCTGAGGG TGGACAGTGG GCAGCTTAGT GCATAGGGCC CTGAAGTCCC | 574 |
| CTCACTTGGC CCCAGAGCTC TGACCCCCAG CCAGCCCACG TGGGGCCTAC AGGGACACTC | 634 |
| GTTCCGAGCA GGCTGCCAGG ATCCNNNNNN NNNNNNATAG ATGACGTGAA GGAGGCCCAG | 694 |
| AGGTTCCTAA CCCCAGAGGG CTAGGAACTT GCCCAGGGTG GCACGGCAAA TTAGGAGCAC | 754 |
| CAGCCATCTA GAAACAGGCT CCAGAGCCCC AGGNATACCC AGGGATNGTG GCCACCTGCA | 814 |
| CACAGGGCAG CTTCAGTGTC CCCCAAAAAG CCTTGAGGCC CATTGGCTGC CCCCGGCCTC | 874 |

ATGCCAGCGT TCTGCTCACT GTTCTGCTCC TTAG GGG GCT GGA GAC CAC TGC TAC    929
                                                       Gly Ala Gly Asp His Cys Tyr
                                                              30                        35

TAC CAG GGG AAG CTC CGG GGG AAC CCG CAC TCC TTC GCC GCC CTC TCC    977
Tyr Gln Gly Lys Leu Arg Gly Asn Pro His Ser Phe Ala Ala Leu Ser
               40                     45                         50

ACC TGC CAG GGG CTG CA GTGAGTATGG GGAGGGGCCG GGCAGCTGGG    1024
Thr Cys Gln Gly Leu His
          55

AGAAGCCTCT GGCCCAGGCC TGGGGACGGA GGGGAGCTGC GCCTCTCTCT CCACAG T    1081

GGG GTC TTC TCT GAT GGG AAC TTG ACT TAC ATC GTG GAG CCC CAA GAG    1129
Gly Val Phe Ser Asp Gly Asn Leu Thr Tyr Ile Val Glu Pro Gln Glu
60                      65                         70

GTG GCT GGA CCT TGG GGA GCC CCT CAG GTAAGCCCCA CACAACCCCT    1176
Val Ala Gly Pro Trp Gly Ala Pro Gln
      75                      80

| | |
|---|---|
| TGCCATCCTC TCTGGTGGCC CTGCCAAGCT TGTCCCAACA GCTGTTGCTG CCACCTCTTC | 1236 |
| CTCCTCCGGC TCCTCCCTCA GTAACCCCAG CCTCACTGCC CTCTTCAGTG ACCCCAGCTC | 1296 |
| TGGTTCCCTC CCTCCTGTGC CCCAGCTCCC CCTGTGCCCC CAGCTCCAAT GTCCCATCTG | 1356 |
| TCCCATAAGT GACCTCCCAT TGGGCTCCAA TGTCCTTTGC CCCTGTCTCT CAGGGTGCCC | 1416 |
| CCAGGTCTTG ACCCCGGAAT CTGAGCATCT GGGAGATCAG ATCCGACATG GGAGCTGTGG | 1476 |
| CCAGTTCTGG GTCACCCCAG GGTGGGGTGG AGGCGAGGGC TGGATCTGGC CCCCGCCAAG | 1536 |
| TGGCCTGGAG CAGGCCCAGT TGGCACCCCA AGAACTAATT TCCCCTCATT GCAG GGA | 1593 |
|                                                                                                             Gly | |

CCC CTT CCC CAC CTC ATT TAC CGG ACC CCT CTC CTC CCA GAT CCC CTC    1641
Pro Leu Pro His Leu Ile Tyr Arg Thr Pro Leu Leu Pro Asp Pro Leu
               85                     90                         95

GGA TGC AGG GAA CCA G GTAAGGGAGG GGAGGGGGGG TGGGGAGGGG CCNGGCTGTG    1697
Gly Cys Arg Glu Pro Gly
           100

CCCCCCTCAC CTGCCCCTCC CCGACAG GC TGC CTG TTT GCT GTG CCT GCC CAG    1750
                                               Cys Leu Phe Ala Val Pro Ala Gln
                                               105                   110

TCG GCT CCT CCA AAC CGG CCG AGG CTG AGA AGG AAA AGG CAG    1792
Ser Ala Pro Pro Asn Arg Pro Arg Leu Arg Arg Lys Arg Gln
      115                           120                         125

| | | | | | |
|---|---|---|---|---|---|
| GTACGGGGGC | CCGCACAGAC | CTCGGGCTGC | AGAGACCTCG | GGCTGCAGAG | AGACCTCGGC | 1852
| CGTGGCCCAG | AGCAGGAGGG | CACCCTCATC | TATGGCTGGG | GCGAAGGAAG | GCTCAGATGG | 1912
| ATGTGGCTGG | GGGCCAGGGA | CCGTGTCTGG | GAGAAGCCCC | CACCCCTTCC | CTAATGCTGG | 1972
| CATCTACAGA | GGCCCCATCC | TGGGCAAACC | GAGGCTGCCT | GCCCTCATTC | CAAAGCTGAG | 2032
| GAAGGACAGG | ACCCTCTGCC | AGTGGGGAGC | TGGCACTGTC | CCTGGCTGGA | GTCCAGACCC | 2092
| CCCCATCCCC | ACCGAGTCTG | TTCCTGGCTT | GGCCATGAGA | TCAGTCAGAC | ATGGAAGGGA | 2152

```
CTGATTCCAA GTGCCCACCC ACCCCCCAG GTC CGC CGG GGC CAC CCT ACA GTG      2205
                                 Val Arg Arg Gly His Pro Thr Val
                                 130                         135

CAC AGT GAA ACC AAG TAT GTG GAG CTA ATT GTG ATC AAC GAC CAC CAG      2253
His Ser Glu Thr Lys Tyr Val Glu Leu Ile Val Ile Asn Asp His Gln
            140             145                 150

CTG GTGAGTGCCA GGGCAGGGAC AGGGCGTGAC ACTGGGAGGC CCCTGAGGAG           2306
Leu

CCTGGCCCTC CTCCCATTCT TCTCTCTCCC AG TTC GAG CAG ATG CGA CAG TCG      2359
                                    Phe Glu Gln Met Arg Gln Ser
                                                    155

GTG GTC CTC ACC AGC AAC TTT GCC AAG TCC GTG GTG AAC CTG GCC GAT      2407
Val Val Leu Thr Ser Asn Phe Ala Lys Ser Val Val Asn Leu Ala Asp
160             165                 170                 175

GTG GTAAGCAGCT CTCCCTCCCT CCCTTCCCTC CTCCTCATGC CCCCCCACCC           2460
Val
```

| | | | | | |
|---|---|---|---|---|---|
| CACCACACAC | ATTAGGGGGC | ACTGTCAGCC | CCTGGCTCCC | ACTTCCTGGA | GAGAACAGAC | 2520
| AGGCCCTCCT | CCAGCCCTGG | CCCCAACACC | CACTCCCACC | CTCCAGCCCC | CCTCATCTTC | 2580

```
TCCCCAG ATA TAC AAG GAG CAG CTC AAC ACT CGC ATC GTC CTG GTT GCC     2629
        Ile Tyr Lys Glu Gln Leu Asn Thr Arg Ile Val Leu Val Ala
            180             185                 190

ATG GAA ACA TGG GCA GAT GGG GAC AAG ATC CAG GTG CAG GAT GAC CTC     2677
Met Glu Thr Trp Ala Asp Gly Asp Lys Ile Gln Val Gln Asp Asp Leu
            195                 200                 205

CTG GAG ACC CTG GCC CGG CTC ATG GTC TAC CGA CGG GAG GGT CTG CCT     2725
Leu Glu Thr Leu Ala Arg Leu Met Val Tyr Arg Arg Glu Gly Leu Pro
            210                 215                 220

GAG CCC AGT AAT GCC ACC CAC CTC TTC TC  GTGAGTCCCC CACCCTGCAC        2774
Glu Pro Ser Asn Ala Thr His Leu Phe Ser
            225                 230
```

| | | | | | |
|---|---|---|---|---|---|
| CTCCTGCCAG | CCTCTGCTAG | TTGCTACAGT | GCTTGGGATT | ACTAACACC | TGCCCTGTGC | 2834
| TGGCTGCTCC | TCTCAGAGTC | TGGGGACTGG | GCTCACCTTG | CACCTGCCAC | CTACCCCCAG | 2894
| CCACATGCAA | CAGCTGGGCA | TCATCCCCTG | AATCTGAGGT | TGATGCCCTT | GTCTTAGCCC | 2954
| TGGTGGTCCT | CTTCTGCCTC | TCACCTCCCC | TTAGTTCTGT | CTTTCCCTTC | AACTGTCCCN | 3014
| NNNNNNNNN | NAGAGTGAAA | CTCTGTCTCA | AAAGAAAAAN | AAAANAAAAG | AAGAAAAAA | 3074
| AGAACCCAAG | GAGCGGGGGA | AGGGTCTTGC | CTGGGGTCAC | CAAGGCTGAT | GTAAAGGGCC | 3134
| AGGCTCACCT | CCTGAGGAAG | GACTCTAGTG | TGAGGGGCTC | CCCAAGGCCC | CACCACCACC | 3194

```
CGGGGAGCCA CAGGGGAGGG CAGAAGCCAT CCTGACAGCG CACTCCCTTC CAG G GGC    3251
                                                              Gly

AGG ACC TTC CAG AGC ACG AGC AGC GGG GCA GCC TAC GTG GGG GGC ATA     3299
Arg Thr Phe Gln Ser Thr Ser Ser Gly Ala Ala Tyr Val Gly Gly Ile
    235                 240                 245

TGC TCC CTG TCC CAT GGC GGG GGT GTG AAC GAG GTGAGCAGTG               3342
Cys Ser Leu Ser His Gly Gly Gly Val Asn Glu
250             255                 260
```

```
GGGGGACATG GCTGGGGTGG CGGCTGAGGG AAAGGGGCTT AGGGGCACGA CGTGCCTGNT        3402

TGGAAGATGT AGACATCTGT GCCCCATCTT CCCCACCCCC AG TAC GGC AAC ATG          3456
                                              Tyr Gly Asn Met

GGG GCG ATG GCC GTG ACC CTT GCC CAG ACG CTG GGA CAG AAC CTG GGC         3504
Gly Ala Met Ala Val Thr Leu Ala Gln Thr Leu Gly Gln Asn Leu Gly
265                 270                 275                 280

ATG ATG TGG AAC AAA CAC CGG AGC TCG GCA G GTATCCTCCC CCAGAGGCCC          3555
Met Met Trp Asn Lys His Arg Ser Ser Ala Gly
            285                 290

CCGTGTGGCC CAGCAGCTCT GGAACGGGAG GGTGACAGTG GGAGGGGTGG TCCTTGGCCT        3615

CCCTCATATC CGCCTGGCTC ACCCCTCAG GG GAC TGC AAG TGT CCA GAC ATC          3667
                                  Asp Cys Lys Cys Pro Asp Ile
                                                      295

TGG CTG GGC TGC ATC ATG GAG GAC ACT GG GTGAGTTCTT GGGGACAACC             3716
Trp Leu Gly Cys Ile Met Glu Asp Thr Gly
300                 305

GGGGGAAGGT CTTGGGCGAG GGGAGTCTTA GAGCGAGCAT TGTTTGGCAG TCTGGACCAG        3776

GGGNNNNNNN NNNNNGAACA CACCTTCCCT TCCAGGCCGG CTTGCGAGTC CCAGGTTCAA        3836

GCGAGGGATG GGAGCGACAA GGACAAGGC GGAGGATTCT GGTGCAATCC CGGGGCAGAT         3896

CCTCCGCCTC CTCGCGATGG TGACGAAGTC CCCCAGTGTA CCCCCTCCCC AGCCTTGAGA        3956

GGGGTGAGGG TGGGTTGGAG GGGAGCAGCC AGCAGCACCT CCCCTCGCCC TATCCAG G         4014

TTC TAC CTG CCC CGC AAG TTC TCT CGC TGC AGC ATC GAC GAG TAC AAC         4062
Phe Tyr Leu Pro Arg Lys Phe Ser Arg Cys Ser Ile Asp Glu Tyr Asn
        310                 315                 320

CAG TTT CTG CAG GAG GGT GGT GGC AGC TGC CTC TTC AAC AAG CCC CTC         4110
Gln Phe Leu Gln Glu Gly Gly Gly Ser Cys Leu Phe Asn Lys Pro Leu
325                 330                 335                 340

AAG GTACCAGCCC CGCGGCGGGG AGCATGGGAG CGGGCCCTGG GCGGGGTCCG              4163
Lys

GGCCAGACTC CCGACCTGTC CTCCCGGTCC AG CTC CTG GAC CCC CCA GAG TGC         4216
                                   Leu Leu Asp Pro Pro Glu Cys
                                                       345

GGG AAC GGC TTC GTG GAG GCA GGG GAG GAG TGC GAC TGC GGC TCG GTG         4264
Gly Asn Gly Phe Val Glu Ala Gly Glu Glu Cys Asp Cys Gly Ser Val
350                 355                 360

CAG GTGAGCGGTG GTGCGGGCGC CAGGTGGGGA ACCGGGATGC GGGGGTGGGC               4317
Gln
365

ACCAGGGAGC GTCTGAGTGG GAGGATTAGG GCTCGCCCGC CTCCTTCCCC TCCTCCCGCG        4377

TCCCTCAG GAG TGC AGC CGC GCA GGT GGC AAC TGC TGC AAG AAA TGC ACC        4427
         Glu Cys Ser Arg Ala Gly Gly Asn Cys Cys Lys Lys Cys Thr
                     370                 375

CTG ACT CAC GAC GCC ATG TGC AGC GAC GGG CTC TGC TGT CGC CGC TGC         4475
Leu Thr His Asp Ala Met Cys Ser Asp Gly Leu Cys Cys Arg Arg Cys
380                 385                 390                 395

AAG GTAAGCAGGA CCGGCCGGGA GGCGGGGCCA GGACGCAGGA GGAGCGATTG               4528
Lys

GAGGCCTTCA TATAAGGGGT GGGAGCTAGG GAGGGAAGCG GAGCCTTCGG GGACGAAGGC        4588

CTCTGGGGCA GGGCTTGATG CGAAGACAGC GCCAATGGGA GCAAGGGCGG GCTGAAGGAT        4648

GTTGAAGGCN NNNNNNNNN NNNCGGACGG GAAGCTCCCA GAATCAAGGA GGGCGGGAAG         4708

GTGGGCGGGC TTGGGGCGGT GCTGAGTGCG CTGGGAGCGA GGTGGGGAGC GTTCAAGAGG        4768

TGGTGGGAGC AGGGAAATAA GAACAGGCCT AAACGGGGCC CTGGGGAGCT GGAGGGCCCG        4828

GGGATGTGGG GGTCCAGAGA GCGGGGGGCC TGGGGAGGGC AGGGCCGAGG CATCCATCCT        4888
```

-continued

```
GCCTGACTCG AGGAGCGCGT CTCTTCCCTA G TAC GAA CCA CGG GGT GTG TCC          4940
                                  Tyr Glu Pro Arg Gly Val Ser
                                              400

TGC CGA GAG GCC GTG AAC GAG TGC GAC ATC GCG GAG ACC TGC ACC GGG         4988
Cys Arg Glu Ala Val Asn Glu Cys Asp Ile Ala Glu Thr Cys Thr Gly
    405                 410                 415

GAC TCT AGC CAG GTCCGCCCGG CCCCGCCGTC TTGTGGAGCC CTGGGCGAGG             5040
Asp Ser Ser Gln
420

CAACCCCTAC CCTTGTCGAT TTGGTTTTCC CGGACGAGTG CTCAGCACTC CCTCCTCTC         5100
CACAGCTGGC ATCGACCTTC ACTGATCAGA CTGTTTTCTT ATCTGAGAAA GGGGTTCTTC        5160
ATGCTCCTGG CCTTGTTCCT TCAATCATTA AACCAGAATG TATCGTCTGG CTGGTATCCC        5220
AGCGCCTGGG CCCGGTGNNN NNNNNNNNTA CCCAGATTCC TCCTGGGCAG CCCTCAGCTC        5280
CAGTCCTGGG CAGCCCTCAG CCCAGTCCTG GGACTGCTCC GCTCAACCCC ACCCCTCTCT        5340

CCACAG TGC CCG CCT AAC CTG CAC AAG CTG GAC GGT TAC TAC TGT GAC          5388
       Cys Pro Pro Asn Leu His Lys Leu Asp Gly Tyr Tyr Cys Asp
                425                 430                 435

CAT GAG CAG GTATGATGGC TGCCCCCTGA GCCTGGGATT CAGGGCAGTC                  5437
His Glu Gln
        440

TCTTATCTCC ACTCTGACCA CTCAGCATCT CCATCCCTTG CCTCTTAATT CTTGGACTCT        5497

CAG GGC CGC TGC TAC GGA GGT CGC TGC AAA ACC CGG GAC CGG CAG TGC         5545
    Gly Arg Cys Tyr Gly Gly Arg Cys Lys Thr Arg Asp Arg Gln Cys
                    445                 450                 455

CAG GTT CTT TGG GGC CAT G GTGAGTCTGC TAGGGCTGGA GTGGGACTCC              5594
Gln Val Leu Trp Gly His Ala
                460

GGAGGAGCCC AGAGCTGAGA AGCTGGGGAG AGTGGGTTCC AGCTGAACAG GCCCCAAGT        5654
GTGTAGCTCC CCAGGATCTC AGGGAGCCCA GGCAGAGTGT GGGAGATGCA GGCCTGAGGT       5714
CTTGGGGTGG GTCCTGGGGC ACGTGGGGTC ACTTGGCATC CTCTCCCCAC AG CG GCT        5771
                                                              Ala

GCT GAT CGC TTC TGC TAC GAG AAG CTG AAT GTG GAG GGG ACG GAG CGT         5819
Ala Asp Arg Phe Cys Tyr Glu Lys Leu Asn Val Glu Gly Thr Glu Arg
    465                 470                 475

GGG AGC TGT GGG CGC AAG GGA TCC GGC TGG GTC CAG TGC AGT AAG CA          5866
Gly Ser Cys Gly Arg Lys Gly Ser Gly Trp Val Gln Cys Ser Lys Gln
480                 485                 490                 495

GTGAGTACTG AGGCTCCCAG AGGGCCTCTC AGCTCCAGGG CAGGTGTGAG ACTTTTCAGA       5926
GATGGGGTAG TAGGTTCTCC CAGGAGGAGC CTGTCAGTCC CAATGGGCGG GCACGTGGCA       5986
AATGAGGTGG CAGGGTGCAG GGTGAGGGCA GATTAGAGTT CAGTAGTTGA GTCTGAGGTC       6046

AAACTTGGGG CTCACTGTCT CTATAT G CCC CAA CAG GGA CGT GCT GTG TGG          6097
                              Pro Gln Gln Gly Arg Ala Val Trp
                                              500

CTT CCT CCT CTG TGT CAA CAT CTC TGG AGC TCC TCG GCT AGG GGA CCT         6145
Leu Pro Pro Leu Cys Gln His Leu Trp Ser Ser Ser Ala Arg Gly Pro
    505                 510                 515

GGT GGG AGA CAT CAG TAGTGTCACC TTCTACCACC AGGGCAAGGA GCTGGACTGC         6200
Gly Gly Arg His Gln
520

AGGTGCTGAC CAGCACCAAA ACTCAGGGAG GGGACCTGGC AGCTGTGCTG GGGGTTAGAA       6260
GATCTGGGGG CTGGAGGCTG GGCTGTGTCA CTTCCCCAGG GGAGGCCACG TGCAGCTGGC       6320
GGACGGCTCT GACCTGAGCT ATGTGGAGGA TGGCACAGCC TGCGGGCCTA ACATGTTGTG       6380
```

```
CCTGGACCAT CGCTGCCTGC CAGCTTCTGC CTTCAACTTC AGCACCTGCC CCGGCAGTGG    6440
GGAGCGCCGG ATTTGCTCCC ACCACGGGGT GACTGCCTGG AGCCCGGGAT GGCGGGAGAA    6500
GCTTACAAGA GGGGACAGGC CCCTGCTCAC CTCTCCTGGC CCTGCCCTGC CTCTAGGTCT    6560
GCAGCAATGA AGGGAAGTGC ATCTGTCAGC CAGACTGGAC AGGCAAAGAC TGCAGTATCC    6620
ATAACCCCCT GCCCACGTCC CCACCCACGG GGAGACGGA  GAGATATAAA GGTGAGGCTG    6680
GAGCTGGCCG AGGGGGGTCT GTCTGTCCCG CTCTCTATGC CTGTCCTTGC CAGCTAAGCC    6740
CTGCCATCCT CCCAGGTCCC AGCGGCACCA ACATCATCAT TGGCTCCATC GCTGGGGCTG    6800
TCCTGGTTGC AGCCATCGTC CTGGGCGGCA CGGGCTGGGG ATTAAGTAA  GAGACACACA    6860
CACCCTGTGC CCCCTGGCAT CCTTGAGGGG GGATCAGAAT CCCTACTGGT GGAGCTGAGG    6920
GGGCCCTCCC TGAAAGCCCA ACTGAACCAG AGCTCACACG TCATAGGTCC AAGTAGCCTG    6980
CAGGGCTTAA CATTTAGAAA CTAGGAGATT TTAGGCTAGA TGAGGTGCTC ACGCCTGTAA    7040
TCCCAGCACT TGGGAGGCC  AAGGCAGGCG GATCACCTGA GGTCAGGAAT TCAAGACCAG    7100
TCTGGCCAAC ATGGTGAAAC CCGTCTCTAT TAAAAATACA AAAATTAGCC AGCCATGGTG    7160
GTGCACACCT GTAATCCCAG CTACTTGCGA GGCTGAGGCA GAGAATTGCT TGAACCCGGG    7220
AGGTGGAGGT TGCAGTGAGC TGAGATCGCA CCATTGCACT CCAGCCTTGG GTGACAGAGC    7280
AAGACTGCGT CAAAAAAAAA AAAAAAAAAA AAAAAAGGA  AGAAAGAGA  GAAAGAAAG    7340
AAAAGAGAAA AGAAATCAGG AGATTTTACA CTAGCAATTC GGATTTCCAG CTCTGGAAAC    7400
ATGAAAAGGT TGAGCCCCAG CGTGCCTCTA AGCATCCCCA AATAGCCACA GAGTGGAGCT    7460
GGGCAGGGGC CACCCAAGCC AGGCATGTGT CCTCCAGTCT CCAGTTCCCA CCAGCCTATA    7520
CTCCTTTGTG CGTGTCTAAG TTTGGGGTCC TTGTGCCTGG TCTTACCCCC CTTAATGTGC    7580
AGAGGGAGGA ACCCACGGCC CAAGGTCACA TGATTGAGTT AGTAGCAGAG TCAGAGCTGG    7640
AACCGGGACG CATTTTTGTG GGTGCCCTGG GTAATTCTCC CTGGCCCTTA CATTAGTGTC    7700
CAGGCCCCGG GGACCCCGGC CCCGCTCTGG GGCAAGGGGT CGCATGGCAG CCAAAGGCCC    7760
CTCCCTGAGA GAAGCAAAAG GTCAGATGTC TCCTTTTCCT CTCCCCTTCC ACCATCCTCC    7820
CCCTGCAGAA ACATTCGCCG AGGAAGGTAC GACCCGACCC AGCTGGGGC  AGTGTGATGC    7880
CGGCCACGTC ATCCCTCCCG CTGTCCTTGT CTCCTCCATC TCATTCGTCA CCCGCGTTCT    7940
GTTGATGGGG TGCGGGGCCG ATCCCACCCT GCGTGCCNNN NNNNNNNNNN ATCTGTTTTG    8000
TCTTCCATAT CACCACTGTC TGACCTCCCG CAGATCCCTT CCCTGGCCAG CCTGTGACTT    8060
GCCGCCTGCC TCCAGGGCCC AGAACTGAGC TCCGGGGCCC TGCTGGGGGG CTCTCCCCGA    8120
GGCCCCTGCT CACGTCCTCC CCTGATGCCC CCTCTCCGTT CCAGGTCCGG AGGGGCCTAA    8180
GTGCCACCCT CCTCCCTCCA AGCCTGGCAC CCACCGTCTC GGCCCTGAAC ACGAGGCTG    8240
CCCCCATCCA GCCACGGAGG GAGGCACCAT GCAAATGTCT TCCAGGTCCA AACCCTTCAA    8300
CTCCTGGCTC CGCAGGGGTT TGGGTGGGGG CTGTGGCCCT GCCCTTGGCA CCACCAGGGT    8360
GGACCAGGCC TGGAGGGCAC TTCCTCCACA GTCCCCACC  CACCTCCTGC GGCTCAGCCT    8420
TGCACACCCA CTGCCCCGTG TGAATGTAGC TTCCACCTCA TGGATTGCCA CAGCTCAACT    8480
CGGGGGCACC TGGAGGGATG CCCCCAGGCA GCCACCAGTG GACCTAGCCT GGATGGCCCC    8540
TCCTTGCAAC CAGGCAGCTG AGACCAGGGT CTTATCTCTC TGGGACCTAG GGGACGGGG    8600
CTGACATCTA CATTTTTTAA AACTGAATCT TAATCGATGA ATGTAAACTC GGGGTGCTG    8660
GGGCCAGGGC AGATGTGGGG ATGTTTTGAC ATTTACAGGA GGCCCCGGAG AAACTGAGGT    8720
ATGGCCATGC CCTAGACCCT CCCCAAGGAT GACCACACCC GAAGTCCTGT CACTGAGCAC    8780
```

| | | | | | | |
|---|---|---|---|---|---|---|
| AGTCAGGGGC | TGGGCATCCC | AGCTTGCCCC | CGCTTAGCCC | CGCTGAGCTT | GGAGGAAGTA | 8840 |
| TGAGTGCTGA | TTCAAACCAA | AGCTGCCTGT | GCCATGCCCA | AGGCCTAGGT | TATGGGTACG | 8900 |
| GCAACCACAT | GTCCCAGATC | GTCTCCAATT | CGAAAACAAC | CGTCCTGCTG | TCCCTGTCAG | 8960 |
| GACACATGGA | TTTTGGCAGG | GCGGGGGGGG | GTTCTAGAAA | ATATAGGTTC | CTATAATAAA | 9020 |
| ATGGCACCTT | CCCCCTTTNN | NNNNNNNNNN | NNNGGGATAC | CTCTGAATAT | GGGTATCTGG | 9080 |
| GGCTGGATAT | GGGTGGGACA | TGAGACTTCC | TGTGACCAGC | CACCCTGGCT | CCCAGCTCTC | 9140 |
| TGTATCCTCC | TGCCCCGCCC | TGGGGGGTGC | CTACCCTGGN | AGAACCCAGG | GAGGAGTGGA | 9200 |
| GGCTGCCTCT | GCCTGGGCCT | CCACACAGCA | TCCTGACATA | CGCCACCTGG | GGTGGGGGTG | 9260 |
| GGGAGGCAGG | GCCAGGAG | | | | | 9278 |

( 2 ) INFORMATION FOR SEQ ID NO: 10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO: 10:

GCACCTGCCC CGGCAGT                 17

( 2 ) INFORMATION FOR SEQ ID NO: 11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO: 11:

CCAGGACAGC CCCAGCGATG            20

( 2 ) INFORMATION FOR SEQ ID NO: 12:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO: 12:

GGCTGCTGAT CGCTTCTGCT AC        22

( 2 ) INFORMATION FOR SEQ ID NO: 13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO: 13:

GAGAAGCTGA ATGTGGAGGG           20

( 2 ) INFORMATION FOR SEQ ID NO: 14:

( i ) SEQUENCE CHARACTERISTICS:
 ( A ) LENGTH: 19 base pairs
 ( B ) TYPE: nucleic acid
 ( C ) STRANDEDNESS: single
 ( D ) TOPOLOGY: linear ( i i ) MOLECULE TYPE: Genomic DNA ( x i ) SEQUENCE DESCRIPTION: SEQ ID NO: 14:

GTCAGAGCCG TCCGCCAGC                                                                                         19

( 2 ) INFORMATION FOR SEQ ID NO: 15:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: Genomic DNA ( x i ) SEQUENCE DESCRIPTION: SEQ ID NO: 15:

GCCATCCTCC ACATAGCTCA GG                                                                                     22

( 2 ) INFORMATION FOR SEQ ID NO: 16:

( i ) SEQUENCE CHARACTERISTICS:
  ( A ) LENGTH: 26 base pairs
  ( B ) TYPE: nucleic acid
  ( C ) STRANDEDNESS: single
  ( D ) TOPOLOGY: linear ( i i ) MOLECULE TYPE: Genomic DNA ( x i ) SEQUENCE DESCRIPTION: SEQ ID NO: 16:

GATGTAAGTC AAGTTCCCAT CAGAGA                                                                                 26

( 2 ) INFORMATION FOR SEQ ID NO: 17:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: Genomic DNA ( x i ) SEQUENCE DESCRIPTION: SEQ ID NO: 17:

AACAGCTGGT GGTCGTTGAT CACAA                                                                                  25

( 2 ) INFORMATION FOR SEQ ID NO: 18:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: Genomic DNA ( x i ) SEQUENCE DESCRIPTION: SEQ ID NO: 18:

ATGAGGCTGC TGCGGCGCTG                                                                                        20

( 2 ) INFORMATION FOR SEQ ID NO: 19:

( i ) SEQUENCE CHARACTERISTICS:
  ( A ) LENGTH: 27 base pairs
  ( B ) TYPE: nucleic acid
  ( C ) STRANDEDNESS: single (D) TOPOLOGY: linear (ii) MOLECULE TYPE: Genomic DNA (xi) SEQUENCE DESCRIPTION: SEQ ID NO: 19:

CACAGATCTG GGGGCATATG CTCCCTG 27

(2) INFORMATION FOR SEQ ID NO: 20:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 20:

AACAAGCTTC TACTGATGTC TCCCACC 27

ANTIBODIES TO MDC PROTEINS

This is a division of Ser. No. 08/243,542, filed May 13, 1994.

BACKGROUND OF THE INVENTION

1. Field of the Invention

The present invention relates to anti-MDC protein antibodies DNAs encoding the same, and gene analysis methods. These antibodies can be utilized in diagnosis.

2. Description of the Related Art

The opinion that mutations in cellular proteins play an important role in the onset of cancer has been known for long. Recent advancement in genetic engineering enables analysis of gene mutations in tumor cells, and has brought about a marked progress in the field of cancer research.

Up to this time, the analysis and identification of oncogenes have made such progress that the number thereof has amounted to several score. On the other hand, attention has been focused on tumor suppressor genes for these several years. The tumor suppressor genes which have been discovered thus far include the Rb gene for retinoblastoma (Friend, S. H. et al., Proc. Natl. Acad. Sci. USA, 84, 9095, 1987), the p53 gene (Lane, D. P. et al., Nature, 278,261, 1979) and the APC gene (Kenneth, W. K. et al., Science, 253, 661, 1991) for colorectal tumor, the WT1 gene for Wilms' tumor (Call, K. M. et al., Cell, 60, 509, 1990), and the like. In the case of the p53 gene, some families are known to inherit mutations in the gene ["Li-Fraumeni syndrome" (Makin, D. et al., Science, 250, 1233, 1990; Srivastava, S. et al., Nature, 348, 747, 1990)]. Moreover, it is becoming increasingly clear that defects in multiple genes, and not in a single gene, contribute to the progression of the malignant phenotype of cancer, and it is believed that there exist many more unidentified oncogenes and tumor suppressor genes. The discovery and elucidation of them are expected by not only investigators and clinicians, but also common people all over the world.

Breast cancer is classified into hereditary (familial) breast cancer and nonhereditary (sporadic) breast cancer, and hereditary breast cancer is classified into early-onset and late-onset diseases according to the age of onset. It has been revealed by linkage analyses that, at least early-onset familial breast cancer is linked to a very small region on chromosome 17 (Hall, J. M. et al., Science, 250, 1684–1689, 1990). Moreover, it has been shown that hereditary ovarian cancer is also linked to the same region (Narod, S. A. et al., Lancet, 338, 82–83, 1991).

Accordingly, it is believed that a tumor suppressor gene is present in this region and protein deficiency or mutation induced by an allelic deletion or mutation of the gene is one of the causes of breast and ovarian cancers.

It is believed that in the onset of common (sporadic) breast cancer as well, the occurence of an acquired mutation or allelic deletion of the gene in this region results in protein mutation or deficiency and this causes the transformation of a normal cell to a breast cancer cell (Sato et al., Cancer Res., 51, 5794–5799, 1991). Consequently, isolation of the causative gene present in this region and identification of the protein encoded by the gene are urgent problems to not only physicians and investigators all over the world, but also to common people, particularly women in Europe and America where there are numerous patients with breast cancer.

The present invention provides novel proteins involved in breast and ovarian cancers, DNAs encoding them, and methods for the testing and diagnosis of cancer by using them.

The present inventors disclose a novel gene encoding a 524-amino acid protein which was isolated from chromosomal region 17q21.3 where a tumor suppressor gene(s) for breast and ovarian cancers is thought to be present (Nature genetics, 5.151–157, 1993; this paper is refered in Nature genetics, 5, No. 2, 101–102, 1993).

DISCLOSURE OF THE INVENTION

BRIEF DESCRIPTION OF THE DRAWINGS

FIG. 1 is a diagram showing the positions on chromosome 17 to which 342 cosmid clones hybridize. Clone names are designated by clone numbers alone.

FIG. 3 is a diagram showing partial deletions on chromosome 17q in breast cancers. Solid circles represent the loss of heterozygosity (LOH) and open circles represent the retention of both alleles. Two commonly deleted regions are designated by sidelines.

SUMMARY OF THE INVENTION

Figure 2:
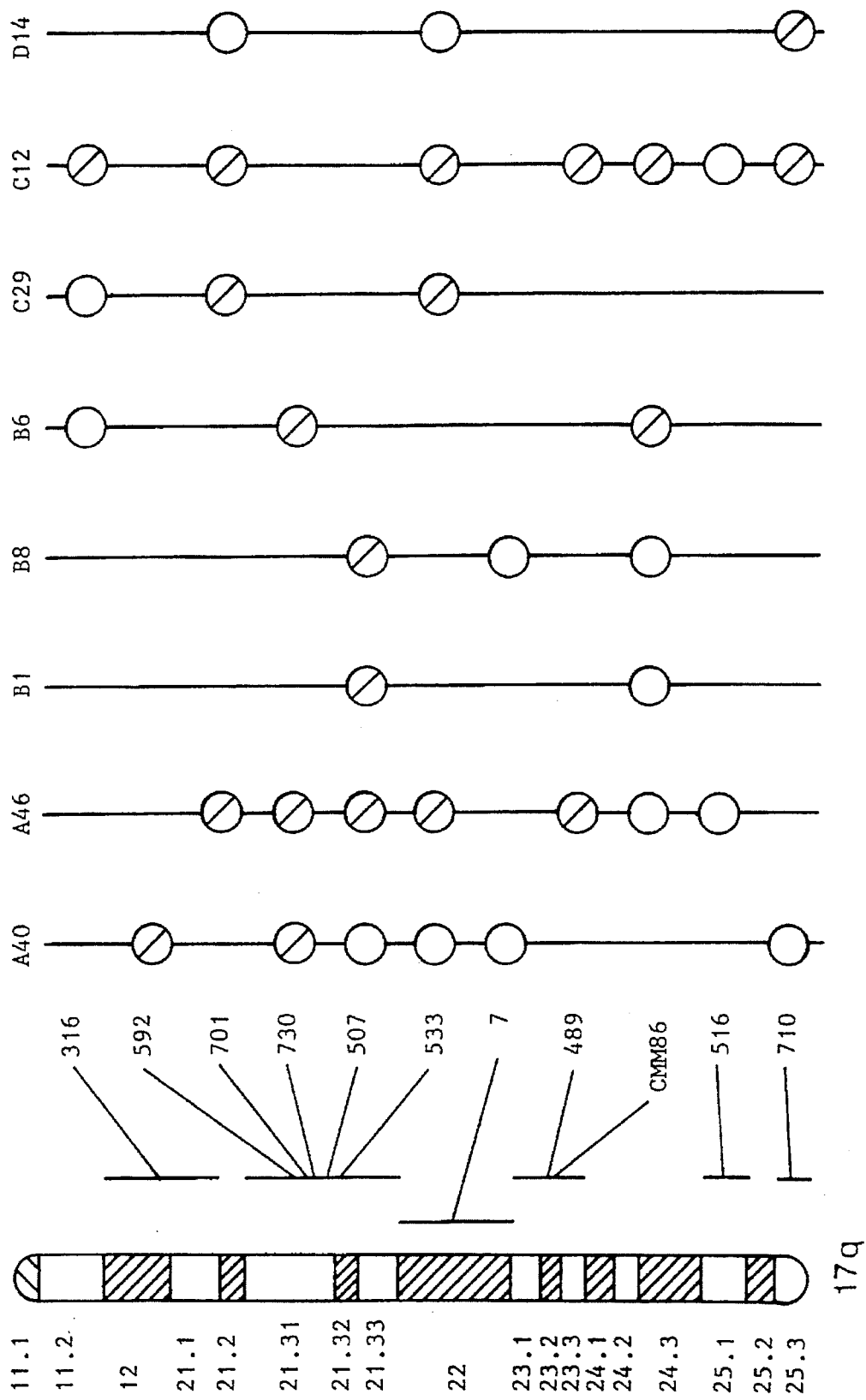
FIG. 2 is a diagram showing partial deletions on chromosome 17q in ovarian cancers. Solid circles represent the loss of heterozygosity (LOH) and open circles represent the retention of both alleles. Two commonly deleted regions are designated by sidelines.

The present inventors constructed a multitude of cosmid clones having DNA fragments of human chromosome 17 introduced thereinto. Then, each of the multitude of cosmid clones was localized throughout the chromosome by fluorescent in-situ hybridization (FISH; Inazawa et al., Genomics, 10, 1075–1078, 1991). The cosmid clones (cosmid markers), localized on the chromosome, enabled construction of a high-resolution physical map of human chromosome 17. The clone names of the cosmids as probes, i.e., the probe names, their detailed map positions and diagrammatical summary of the mapping are shown in Tables 1–3 and FIG. 1, respectively. In FIG. 1, clone names are designated by clone numbers alone.

TABLE 1

| No. | Probe name | Locus symbol | Chromosonal localization | No. | Probe name | Locus symbol | Chromosonal localization |
|---|---|---|---|---|---|---|---|
| 1 | CCI17-1 | | 17q21.1 | 67 | cCI17-501 | | 17q21.3 |
| 2 | cCI17-7 | | 17q22 | 68 | cCI17-502 | | 17p11.2 |
| 3 | cCI17-11 | | 17p11.2 | 69 | cCI17-504 | | 17q24 |
| 4 | cCI17-24 | | 17q21.1-q21.2 | 70 | cCI17-505 | D17S544 | 17p12-p11.1 |
| 5 | cCI17-25 | | 17q12 | 71 | cCI17-506 | D17S545 | 17q21 |
| 6 | cCI17-28 | | 17q21.3 | 72 | cCI17-507 | | 17q21.3 |
| 7 | cCI17-32 | | 17q11.2 | 73 | cCI17-508 | D17S546 | 17q25.1-q25.3 |
| 8 | cCI17-35 | | 17q21.3 | 74 | cCI17-509 | | 17q24 |
| 9 | cCI17-41 | | 17q23.1 | 75 | cCI17-510 | | 17q23 |
| 10 | cCI17-50 | | 17q23.1 | 76 | cCI17-511 | | 17q25.1-q25.2 |
| 11 | cCI17-57 | | 17q21 | 77 | cCI17-513 | D17S548 | 17q11.2 |
| 12 | cCI17-63 | | 17q21.3 | 78 | cCI17-514 | | 17q25.1 |
| 13 | cCI17-90 | | 17q12-q21.1 | 79 | cCI17-515 | | 17q22 |
| 14 | cCI17-95 | | 17q23.1 | 80 | cCI17-516 | D12S550 | 17q25.1 |
| 15 | cCI17-96 | | 17q21.3 | 81 | cCI17-517 | | 17q21.3 |
| 16 | cCI17-97 | | 17q21.3 | 82 | cCI17-518 | | 17q25.3 |
| 17 | cCI17-315 | D17S521 | 17q25.1-q25.2 | 83 | cCI17-519 | D17S551 | 17q25.2-q25.3 |
| 18 | cCI17-316 | | 17q12-q21.1 | 84 | cCI17-520 | | 17q11.2 |
| 19 | cCI17-317 | | 17q11.2 | 85 | cCI17-521 | | 17q25.1-q25.2 |
| 20 | cCI17-321 | | Centromere | 86 | cCI17-523 | | 17q22 |
| 21 | cCI17-403 | | 17q21.2-q21.3 | 87 | cCI17-524 | | 17q21.1-q21.2 |
| 22 | cCI17-412 | | 17q11.2 | 88 | cCI17-525 | | 17p13.1 |
| 23 | cCI17-415 | | 17q21.1-q21.2 | 89 | cCI17-526 | | 17q11.2-q1 |
| 24 | cCI17-422 | | 17q22 | 90 | cCI17-527 | | 17q21.3 |
| 25 | cCI17-425 | | 17q11.2 | 91 | cCI17-528 | | 17q27 |
| 26 | cCI17-428 | | 17q23.1 | 92 | cCI17-529 | D17S552 | 17q25.1-q25.2 |
| 27 | cCI17-451 | | 17q21.1-q21.2 | 93 | cCI17-530 | | 17q23 |
| 28 | cCI17-452 | D17S524 | 17q25 | 94 | cCI17-532 | | 17p11.2 |
| 29 | cCI17-453 | D17S525 | 17p13 | 95 | cCI17-533 | | 17q21.3 |
| 30 | cCI17-454 | D17S526 | 17q23 | 96 | cCI17-535 | | 17q12-q21.1 |
| 31 | cCI17-451 | D17S527 | 17q23.1-q23.2 | 97 | cCI17-536 | | 17p11.2 |
| 32 | cCI17-457 | | 17q11.2 | 98 | cCI17-539 | | 17q21.3 |
| 33 | cCI17-453 | D17S528 | 17q21.1-q21.2 | 99 | cCI17-540 | | 17q25 |
| 34 | cCI17-460 | D17S529 | 17q11.2 | 100 | cCI17-541 | | 17q21.3 |
| 35 | cCI17-462 | | 17q23 | 101 | cCI17-542 | | 17q21.3 |
| 36 | cCI17-463 | | 17q21 | 102 | cCI17-543 | | 17q11.2-q12 |
| 37 | cCI17-464 | | 17q24.3-q25.1 | 103 | cCI17-544 | | 17q25.1 |
| 38 | cCI17-465 | D17S531 | 17q25.1-q25.2 | 104 | cCI17-545 | | 17q25.1 |
| 39 | cCI17-466 | | 17q25.1-q25.2 | 105 | cCI17-546 | | 17q24.3-q25.1 |
| 40 | cCI17-467 | | 17q25 | 106 | cCI17-547 | | 17q21.3 |
| 41 | cCI17-468 | DI7S532 | 17q11.2 | 107 | cCI17-548 | | 17q23 |
| 42 | cCI17-469 | D17S533 | 17q25.2-q25.3 | 108 | cCI17-549 | | 17q25.3 |
| 43 | cC1I7-471 | | 17p13.3-p13.2 | 109 | cCI17-550 | | 17q23 |
| 44 | cCI17-473 | D17S534 | 17q11.2 | 110 | cCI17-551 | | 17q25.1-q25.2 |
| 45 | cCI17-475 | D17S535 | 17q11.2 | 111 | cCI17-552 | | 17q12 |
| 46 | cCI17-477 | | 17q21.3 | 112 | cCI17-553 | | 17q23 |
| 47 | cCI17-479 | | 17q21.3 | 113 | cCI17-554 | | 17q25.1 |
| 48 | cCI17-480 | | 17q25.1-q25.2 | 114 | cCI17-557 | | 17q25.1-q25.2 |
| 49 | cCI17-482 | D17S536 | 17q11.2 | 115 | cCI17-559 | | 17q24.3-q25.1 |
| 50 | cCI17-483 | | 17p13 | 116 | cCI17-560 | | 17q25.1-q25.2 |
| 51 | cCI17-484 | D17S537 | 17p13.1 | 117 | cCI17-561 | | 17q25 |
| 52 | cCI17-485 | | 17q12 | 118 | cCI17-562 | | 17q11.2 |
| 53 | cCI17-486 | | 17q25.1 | 119 | cCI17-563 | | 17q25.1 |
| 54 | cCI17-487 | D17S538 | 17q25.1 | 120 | cCI17-564 | | 17q25.1 |
| 55 | cCI17-488 | D17S539 | 17p13.2-p13.1 | 121 | cCI17-565 | | 17q23 |
| 56 | cCI17-489 | D17S540 | 17q23 | 122 | cCI17-567 | | 17q21.3 |
| 57 | cCI17-490 | | 17q11.2 | 123 | cCI17-568 | | 17q25 |
| 58 | cCI17-491 | | 17p13.1 | 124 | cCI17-569 | | 17q12 |
| 59 | cCI17-492 | D17S542 | 17q11.2 | 125 | cCI17-570 | | 17q11.1 |
| 60 | cCI17-493 | | 17q25.1-q25.2 | 126 | cCI17-571 | | 17q13 |
| 61 | cCI17-494 | | 17q22 | 127 | cCI17-572 | | 17q25.1 |
| 62 | cCI17-495 | | 17q25 | 128 | cCI17-573 | | 17q25.3 |
| 63 | cCI17-497 | | 17q11.2 | 129 | cC1I7-574 | | 17q12-q21.2 |
| 64 | cCI17-498 | | 17p11.2 | 130 | cCI17-576 | | 17q21.1-q21.2 |
| 65 | cCI17-499 | | 17q21.1-q21.2 | 131 | cCI17-577 | | 17q25.1 |
| 66 | cCI17-500 | | 17p-12 | 132 | cCI17-578 | | 17q11.2-q12 |

TABLE 2

| No. | Probe name | Locus symbol | Chromosomal Localization | No. | Probe name | Locus symbol | Chromosomal localization |
|---|---|---|---|---|---|---|---|
| 133 | cCI17-579 | | 17q25.1 | 198 | cCI17-652 | | 17q22 |
| 134 | cCI17-581 | | 17q11.2 | 199 | cCI17-653 | | 17q22 |
| 135 | cCI17-582 | | 17q21.3 | 200 | cCI17-654 | | 17p13 |
| 136 | cCI17-583 | | 17q12-q21.1 | 201 | cCI17-655 | | 17q23 |
| 137 | cCI17-584 | | 17q21.3 | 202 | cCI17-656 | | 17q25.1 |
| 138 | cCI17-586 | | 17p13 | 203 | cCI17-657 | | 17p13 |
| 139 | cCI17-587 | | 17p13 | 204 | cCI17-658 | | 17q21.3 |
| 140 | cCI17-588 | | 17p13.1 | 205 | cCI17-659 | | 17q25.1 |
| 141 | cCI17-590 | | 17q12 | 206 | cCI17-660 | | 17q25.1 |
| 142 | cCI17-591 | | 17q24 | 207 | cCI17-662 | | 17p12 |
| 143 | cCI17-592 | | 17q21.3 | 208 | cCI17-663 | | 17q25.1 |
| 144 | cCI17-593 | | 17q25.1-q25.2 | 209 | cCI17-664 | | 17q25.1-q25.2 |
| 145 | cCI17-594 | | 17q25.2-q25.3 | 210 | cCI17-665 | | 17q23 |
| 146 | cCI17-595 | | 17q25.1-q25.2 | 211 | cCI17-666 | | 11q23.1 |
| 147 | cCI17-596 | | 17q11.2 | 212 | cCI17-667 | | 17q24 |
| 148 | cCI17-597 | | 17q25.3 | 213 | cCI17-668 | | 17q22 |
| 149 | cCI17-598 | | 17q12-q21.1 | 214 | cCI17-669 | | 17p13 |
| 150 | cCI17-599 | | 17q12 | 215 | cCI17-670 | | 17q21.3 |
| 151 | cCI17-600 | | 17q23 | 216 | cCI17-671 | | 17q11.2 |
| 152 | cCI17-601 | | 17q21.1-q21.2 | 217 | cCI17-672 | | 17q25.1-q25.2 |
| 153 | cCI17-602 | | 17q11.2-q12 | 218 | cCI17-673 | | 17q12-q21.1 |
| 154 | cCI17-603 | | 17p11.2 | 219 | cCI17-674 | | 17q21.3 |
| 155 | cCI17-604 | | 17q23 | 220 | cCI17-675 | | 17q21.3 |
| 156 | cCI17-605 | | 17q21.1-q21.2 | 221 | cCI17-676 | | 17q23 |
| 157 | cCI17-606 | | 17p13 | 222 | cCI17-677 | | 17q12-q21.1 |
| 158 | cCI17-607 | | 17q25 | 223 | cCI17-678 | | 17q23 |
| 159 | cCI17-608 | | 17p11.2 | 224 | cCI17-679 | | 17q23.1 |
| 160 | cCI17-609 | | 17q21.3 | 225 | cCI17-680 | | 17p13 |
| 161 | cCI17-610 | | 17q12-q21.1 | 226 | cCI17-681 | | 17p11.1-P11.2 |
| 162 | cCI17-611 | | 17q22 | 227 | cCI17-683 | | 17q11.2 |
| 163 | cCI17-612 | | 17q21.3 | 228 | cCI17-684 | | 17q25.1-q25.2 |
| 164 | cCI17-613 | | 17q25.1 | 229 | cCI17-685 | | 17p13 |
| 165 | cCI17-614 | | 17q21.3 | 230 | cCI17-687 | | 17q12 |
| 166 | cCI17-615 | | 17q21.1 | 231 | cCI17-689 | | 17p11.2 |
| 167 | cCI17-616 | | 17q25.1 | 232 | cCI17-690 | | 17q11.2-q12 |
| 168 | cCI17-617 | | 17q21.3 | 233 | cCI17-691 | | 17q25.1 |
| 169 | cCI17-618 | | 17q23.1 | 234 | cCI17-692 | | 17q23 |
| 170 | cCI17-619 | | 17q11.3 | 235 | cCI17-693 | | 17P11.2 |
| 171 | cCI17-621 | | 17q25.1-q25.2 | 236 | cCI17-694 | | 17P11.2 |
| 172 | cCI17-622 | | 17q12 | 237 | cCI17-695 | | 17p11.2 |
| 173 | cCI17-623 | | 17q25.1-q25.2 | 238 | cCI17-696 | | 17q23.3 |
| 174 | cCI17-624 | | 17p13 | 239 | cCI17-697 | | 17q25 |
| 175 | cCI17-625 | | 17q23 | 240 | cCI17-698 | | 17q11.2 |
| 176 | cCI17-626 | | 17q23 | 241 | cCI17-699 | | 17q23 |
| 177 | cCI17-627 | | 17p13 | 242 | cCI17-700 | | 17q23 |
| 178 | cCI17-628 | | 17q23 | 243 | cCI17-701 | | 17q21.3 |
| 179 | cCI17-630 | | 17q11.2 | 244 | cCI17-702 | | 17q25.2-q25.3 |
| 180 | cCI17-631 | | 17p11.2 | 245 | cCI17-703 | | 17p13 |
| 181 | cCI17-622 | | 17q22 | 246 | cCI17-704 | | 17q23 |
| 182 | cCI17-633 | | 17q12 | 247 | cCI17-705 | D17S554 | 17p11.2 |
| 183 | cCI17-634 | | 17q21.3 | 248 | cCI17-706 | D17S555 | 17q12 |
| 184 | cCI17-636 | | 17p13 | 249 | cCI17-707 | D17S556 | 17q25.1-q25.2 |
| 185 | cCI17-637 | | 17q12 | 250 | cCI17-708 | | 17p13 |
| 186 | cCI17-638 | | 17p11.2 | 251 | cCI17-709 | | 17p12 |
| 187 | cCI17-639 | | 17q12 | 252 | cCI17-710 | D17S557 | L7q25.3 |
| 188 | cCI17-640 | | 17q11.1 | 953 | cCI17-711 | | 17q32.1 |
| 189 | cCI17-641 | | 17q25.1 | 254 | cCI17-712 | D17S558 | 17p11.2 |
| 190 | cCI17-642 | | 17q12-q21.1 | 255 | cCI17-713 | D17S559 | 17p13 |
| 191 | cCI17-643 | | 17q21.3 | 256 | cCI17-714 | D17S560 | 17q25.3 |
| 192 | cCI17-644 | | 17q23 | 257 | cCI17-715 | | 17q21.3 |
| 193 | cCI17-645 | | 17p13 | 258 | cCI17-716 | D17S561 | 17p13 |
| 194 | cCI17-646 | | 17p13 | 259 | cCI17-717 | | 17p13 |
| 195 | cCI17-647 | | 17q25.1-q25.2 | 260 | cCI17-719 | | 17q25 |
| 196 | cCI17-650 | | 17q12 | 261 | cCI17-721 | | 17q23 |
| 197 | cCI17-651 | | 17q25.1 | 262 | cCI17-729 | D17S563 | 17q25.2-q25.3 |

TABLE 3

| Probe No. | name | Locus symbol | Chromosomal localization | Probe No. | name | Locus symbol | Chromosomal localization |
|---|---|---|---|---|---|---|---|
| 263 | cCI17-723 | | 17p13 | 304 | cCI17-834 | | 17q11.2-q12 |
| 264 | cCI17-724 | D17S564 | 17p11.2 | 305 | cCI17-835 | | 17q21.3 |
| 265 | cCI17-726 | | 17q25 | 306 | cCI17-841 | | 17p12 |
| 266 | cCI17-727 | D17S566 | 17p13 | 307 | cCI17-1005 | | 17q21.3 |
| 267 | cCI17-728 | D17S567 | 17p12 | 308 | cCI17-1008 | | 17q21.3 |
| 268 | cCI17-729 | D17S568 | 17q11.2 | 309 | cCI17-1016 | | 17q23.1 |
| 269 | cCI17-730 | | 17q21.3 | 310 | cCI17-1018 | | 17q21.2-21.3 |
| 270 | cCI17-732 | D17S570 | 17p13.2 | 311 | cCI17-1019 | | 17q23.1 |
| 271 | cCI17-733 | | 17q25.1 | 312 | cCI17-1024 | | 17q12 |
| 272 | cCI17-735 | D17S572 | 17q25.3 | 313 | cCI17-1029 | | 17q11.2 |
| 273 | cCI17-736 | D17S573 | 17q21.3 | 314 | cCI17-1030 | | 17q22 |
| 274 | cCI17-737 | D17S557 | 17q25.2-q25.3 | 315 | cCI17-1031 | | 17q11.2 |
| 275 | cCI17-739 | D17S575 | 17q25.1 | 316 | cCI17-1032 | | 17q23.1-23.2 |
| 276 | cCI17-741 | | 17q25.3 | 317 | cCI17-1049 | | 17q21.3 |
| 277 | cCI17-742 | | 17q25 | 318 | cCI17-1055 | | 17q21.3 |
| 278 | cCI17-743 | | 17q23.3 | 319 | cCI17-1059 | | 17q21.1-q21.2 |
| 279 | cCI17-744 | | 17q23 | 320 | cCI17-1063 | | 17q12 |
| 280 | cCI17-745 | D17S577 | 17p13 | 321 | cCI17-1073 | | 17q11.2 |
| 281 | cCI17-801 | | 17q11.2-q12 | 322 | cCI17-1079 | | 17q12 |
| 282 | cCI17-802 | | 17p11.2 | 323 | cCI17-1082 | | 17q22 |
| 283 | cCI17-808 | | 17q25.1-q25.2 | 324 | cCI17-1094 | | 17q21.1 |
| 284 | cCI17-809 | | 17q23 | 325 | cCI17-1101 | | 17q12 |
| 285 | cCI17-810 | | 17p13.2-p13.1 | 326 | cCI17-1103 | | 17q11.2 |
| 286 | cCI17-812 | | 17q25.1 | 327 | cCI17-1106 | | 17q11.2 |
| 287 | cCI17-813 | | 17q23 | 328 | cCI17-1702 | | 17q21.1-q21.2 |
| 288 | cCI17-814 | | 17p11.2 | 329 | cCI17-1705 | | 17q21.2-q21.3 |
| 289 | cCI17-815 | | 17q24 | 330 | cCI17-1706 | | 17q21.1-q21.2 |
| 290 | cCI17-816 | | 17q23 | 331 | cCI17-1707 | | 17q21.2-q21.3 |
| 291 | cCI17-817 | | 17q23 | 332 | cCI17-1709 | | 17q12 |
| 292 | cCI17-818 | | 17p11.2 | 333 | cCI17-1710 | | 17q21.3 |
| 293 | cCI17-820 | | 17q12 | 334 | cCI17-1711 | | 17q12 |
| 294 | cCI17-821 | | 17p13 | 335 | cCI17-1715 | | 17q12 |
| 295 | cCI17-822 | | 17q11.1 | 336 | cCI17-1717 | | 17q21.3 |
| 296 | cCI17-823 | | 17q12 | 337 | cCI17-1719 | | 17q11.2 |
| 297 | cCI17-825 | | 17p11.2 | 338 | cCI17-1720 | | 17q24.3-q25.1 |
| 298 | cCI17-826 | | 17q11.2 | 339 | cCI17-1722 | | 17q23 |
| 299 | cCI17-827 | | 17p11.2 | 340 | cCI17-1723 | | 17q21.3 |
| 300 | cCI17-828 | | 17p11.2 | 341 | cCI17-1724 | | 17q11.2 |
| 301 | cCI17-831 | | 17q25.1-q25.2 | 342 | cCI17-1725 | | 17q21.1 |
| 302 | cCI17-832 | | 17p11.2 | 343 | pCMM86 | | 17q23 |
| 303 | cCI17-833 | | 17q23 | | | | |

From among these markers, ones exhibiting restriction fragment length polymorphism (RFLP) in which the lengths of restriction fragments vary with the individual, namely RFLP markers, were selected. The selected marker clones, the restriction enzymes used, and the particular lengths of several fragments detected thereby are shown in Tables 4–6.

TABLE 4

| Probe No. | name | Locus symbol | Enzyme | Allele size (frequency) | Chromosomal localization |
|---|---|---|---|---|---|
| 2 | cCI17-7 | D17S860 | PvuII | 3.0 kb(0.33)<br>1.8 + 1.2 kb(0.67) | |
| 16 | cCI17-97 | D17S861 | PstI | 8.2 kb(0.92)<br>4.7 + 3.5 kb(0.08) | 17q21.3 |
| 17 | cCI17-315 | D17S521 | TaqI | 2.0 kb(0.67)<br>1.8 kb(0.33) | 17q25.1-q25.2 |
| 18 | cCI17-316 | D17S862 | MspI | 3.1 kb(0.33)<br>2.7 kb(0.67) | 17q12-q21.1 |
| 19 | cCI17-317 | D17S522 | TaqI | 2.6 . 3.9 kb 4 alleles VNTR,60% heterozygosity also polymorphic with MspI,PstI,PvuII | 17q11.2 |
| 29 | cCI17-453 | D17S525 | BglII | 5.8–7.5 kb 4 alleles VNTR,50% heterozygosity also polymorphic with EcoRI,TaqI,PstI,PvuII,NapI | 17p13 |
| 42 | cCI17-469 | D17S533 | MspI | 2.0–2.6 kb 5 alleles VNTR,83% heterozygosity also polymolphic with EcoRI,TaqI,PvuII | 17q25.2-q25.3 |
| 54 | cCI17-487 | D17S538 | EcoRI | 5.8 kb(0.75)<br>3.3 kb(0.25) | 17q25.1 |
| 56 | cCI17-489 | D17S540 | MspI | 3.3 kb(0.25)<br>2.1 kb(0.50) | 17q23 |

TABLE 4-continued

| Probe No. | name | Locus symbol | Enzyme | Allele size (frequency) | Chromosomal locatization |
|---|---|---|---|---|---|
| | | | TaqI | 1.5 kb(0.50) 1.35 kb(0.50) | |
| | | | PvuII | 1.2 kb(0.50) 0.7 kb(0.50) | |
| 58 | cCI17-491 | D17S863 | TaqI | 3.6 kb(0.75) 3.3 kb(0.25) | 17p13.1 |
| 59 | cCI17-492 | D17S542 | BglII | 2.1 kb(0.40) 1.4 kb(0.60) | 17q11.2 |
| 61 | cCI17-494 | D17S865 | EcoRI | 10.3 kb(0.92) 7.8 kb(0.008) | |
| 70 | cCI17-505 | D17S544 | MspI | 3.1 kb(0.58) 3.0 kb(0.42) | 17p12-p11.1 |
| | | | TaqI | 4.1 kb(0.67) 2.7 + 1.4 kb(0.33) | |
| 71 | cCI17-506 | D17S545 | KspI | 3.0 kb(0.33) 2.6 kb(0.67) | 17q21 |
| 73 | cCI17-508 | D17S546 | MspI | 4.6 kb(0.50) 4.0 kb(0.50) | 17q25.1-q25.2 |
| 80 | cCI17-516 | D17S550 | TaqI | 4.1 kb(0.25) 2.4 + 1.7 kb(0.75) | 17q25.1 |
| | | | PvuII | 3.4 kb(0.83) 2.2 kb(0.17) | |
| 88 | cCI17-525 | D17S866 | MspI | 2.7 kb(0.42) 2.3 kb(0.58) | |
| 118 | cCI17-562 | D17S5867 | TaqI | 3.5 kb(0.42) 3.2 kb(0.58) | |
| | | | PvuII | 7.1 kb(0.92) 6.6 kb(0.08) | |
| 137 | cCI17-584 | D17S868 | MspI | 3.8 kb(0.25) 3.6 kb(0.75) | |
| 166 | cCI17-615 | D17S869 | PstI | 5.2 kb(0.42) 4.7 kb(0.58) | |
| 243 | cCI17-701 | D17S870 | TaqI 1.7–2.5 kb 6 alleles VNTR,67% heterozygosity also polymorphic with MspI,PstI,PvuII,RsaI | | 17q21.3 |
| 244 | cCI17-702 | D17S871 | MspI | 4.1 kb(0.83) 3.4 kb(0.17) | 17q25.2-q25.3 |
| | | | RsaI | 5.2 kb(0.83) 4.1 kb(0.17) | |
| | | | BglII | 6.6 kb(0.83) 5.6 kb(0.17) | |
| | | | PvuII | 1.9 kb(0.83) 2.2 kb(0.17) | |

TABLE 5

| Probe No. | name | Locus symbol | Enzyme | Allele size (frequency) | Chromosomal localization |
|---|---|---|---|---|---|
| 245 | cCI17-703 | D17S877 | TaqI 2.6–3.8 kb 4 alleles VNTR,50% heterozygosity also polymorphic with MspI,RsaI,PstI,PvuII | | 17p13 |
| 247 | cCI17-705 | D17S554 | PstI | 4.3 kb(0.50) 2.3 + 2.0 kb(0.50) | 17p11.2 |
| 250 | cCI17-708 | D17S878 | PvuII 2.6–9.0 kb 10 alleles VNTR,87% heterozygosity also polymorphic with MspI,TaqI,BglII,PstI,EcoRI | | 17p13 |
| 252 | cCI17-710 | D17S557 | MspI 2.0–2.6 kb 5 alleles VNTR,100% heterozygosity also polymorphic with RsaI,TaqI,PstI,PvuII,EcoRI | | 17q25.3 |
| 254 | cCI17-712 | D17S558 | MspI | 3.1 kb(0.58) 2.9 kb(0.42) | 17p11.2 |
| | | | TaqI | 6.6 kb(0.67) 4.3 + 2.3 kb(0.33) | |
| | | | PvuII | 7.1 kb(0.50) 3.9 + 3.2 kb(0.50) | |
| 255 | cCI17-713 | D17S559 | MspI 2.2–2.8 kb 3 alleles VNTR,50% heterozygosity also polymorphic with PstI | | 17p13 |
| 256 | cCI17-714 | D17S560 | RsaI | 4.5 kb(0.58) 4.3 kb(0.42) | 17q25.3 |
| | | | TaqI | 3.8 kb(0.75) 2.8 kb(0.25) | |

TABLE 5-continued

| Probe No. | name | Locus symbol | Enzyme | Allele size (frequency) | Chromosomal localization |
|---|---|---|---|---|---|
| | | | BglII | 3.8 kb(0.58) | |
| | | | | 3.5 kb(0.42) | |
| | | | PvuII | 2.6 kb(0.58) | |
| | | | | 2.4 kb(0.42) | |
| | | | | 1.5 kb(0.58) | |
| | | | | 1.4 kb(0.42) | |
| 257 | cCI17-715 | D17S872 | PstI | 3.3 kb(0.17) | 17q21.3 |
| | | | | 3.0 kb(0.83) | |
| | | | EcoRI | 3.6 kb(0.87) | |
| | | | | 3.3 kb(0.13) | |
| 258 | cCI17-716 | D17S561 | TaqI | 2.4 kb(0.87) | 17p13 |
| | | | | 1.3 + 1.1 kb(0.13) | |
| 261 | cCI17-721 | D17S864 | RsaI | 2.9 kb(0.25) | 17q22-q23 |
| | | | | 1.6 kb(0.75) | |
| | | | BglII | 4.4 kb(0.83) | |
| | | | | 3.9 kb(0.17) | |
| 262 | cCI17-722 | D17S563 | MspI | 4.1 kb(0.83) | 17q25.2-q25.3 |
| | | | | 3.4 kb(0.17) | |
| | | | RsaI | 5.2 kb(0.83) | |
| | | | | 4.1 kb(0.17) | |
| | | | BglII | 6.6 kb(0.83) | |
| | | | | 5.6 kb(0.17) | |
| | | | PvuII | 2.9 kb(0.83) | |
| | | | | 2.2 kb(0.17) | |
| | | | EcoRI | 13.0 kb(0.75) | |
| | | | | 12.5 kb(0.25) | |
| 263 | cCI17-723 | D17S873 | MspI | 3.0 kb(0.33) | 17p13 |
| | | | | 1.7 kb(0.67) | |
| | | | RsaI | 0.8 kb(0.70) | |
| | | | | 0.5 kb(0.30) | |
| | | | TaqI | 3.6 kb(0.33) | |
| | | | | 1.9 kb(0.67) | |
| | | | PstI | 5.8 kb(0.50) | |
| | | | | 5.3 kb(0.50) | |
| | | | PvuII | 4.6 kb(0.58) | |
| | | | | 4.2 kb(0.42) | |
| 266 | cCI17-727 | D17S566 | PvuII 2.6–9.0 kb 10 alleles VNTR,87% heterozygosity also polymorphic with MspI,TaqI,BglII,PstI,EcoRI | | 17p13 |
| 268 | cCI17-723 | D17S568 | MspI | 4.6 kb(0.58) | 17q11.2 |
| | | | | 2.6 kb(0.42) | |

TABLE 6

| Probe No. | name | Locus symbol | Enzyme | Allele size (frequency) | Chromosomal localization |
|---|---|---|---|---|---|
| 269 | cCI17-730 | D17S874 | MspI 2.2–3.5 kb 4 alleles VNTR,83% heterozygosity also polymorphic with TaqI,BglII,PstI,PvuII | | 17q21.3 |
| 270 | cCI17-732 | D17S570 | RsaI | 3.2 kb(0.50) | 17p13.2 |
| | | | | 2.7 kb(0.50) | |
| | | | BglII | 8.5 kb(0.50) | |
| | | | | 3.2 kb(0.50) | |
| | | | PstI | 9.5 kb(0.58) | |
| | | | | 1.7 kb(0.42) | |
| | | | PvuII | 4.2 kb(0.50) | |
| | | | | 4.1 kb(0.50) | |
| 271 | cCI17-733 | D17S875 | MspI | 3.4 kb(0.75) | 17q25.1 |
| | | | | 2.6 kb(0.25) | |
| 272 | cCI17-735 | D17S571 | MspI | 4.1 kb(0.83) | 17q25.3 |
| | | | | 3.4 kb(0.17) | |
| | | | RsaI | 5.2 kb(0.83) | |
| | | | | 4.1 kb(0.17) | |
| | | | PvuII | 2.9 kb(0.83) | |
| | | | | 2.2 kb(0.17) | |
| 273 | cCI17-736 | D17S573 | TaqI 1.7–2.5 kb 7 alleles VNTR,100% heterozygosity also polymorphic with MspI,RsaI,PstI,PvuII | | 17q21.3 |
| 275 | cCI17-739 | D17S575 | MspI | 3.3 kb(0.33) | 17q25.1 |

TABLE 6-continued

| Probe No. | name | Locus symbol | Enzyme | Allele size (frequency) | Chromosomal localization |
|---|---|---|---|---|---|
| 278 | cCI17-743 | D17S876 | TaqI | 2.4 kb(0.67) 4.3 kb(0.17) 2.8 kb(0.83) | |

RFLP markers are characterized in that they can be used to distinguish between two alleles inherited from parents by the difference in polymorphism ("informative"), however, they are indistinguishable when both of them have the same polymorphic pattern ("not informative"). If such a difference in polymorphic pattern between two alleles ("heterozygosity") exists in normal tissues and the loss of heterozygosity (LOH) is detected in tumor tissues, this implies an allelic deletion in the RFLP marker site on a specific chromosome of tumor tissues. It is generally believed that the inactivation of tumor suppressor genes on both alleles, as caused by the deletion of one allele and the mutation in the other, may lead to malignant transformation. Thus, it is assumed that a tumor suppressor gene is present in a region commonly deleted in many cancers.

Using the detailed chromosome map and RFLP markers thus obtained, the present inventors examined about 300 breast cancers and about 100 ovarian cancers for LOH in chromosome 17. As a result, it was revealed that, in informative cases, a region (of 2.4 cM) lying between cosmid markers cCI17-701 and cCI17-730 located in the neighborhood of 17q21 was deleted with high frequency.

FIG. 2 shows partial deletions on chromosome 17q in ovarian cancers. Solid circles represent the loss of heterozygosity (LOH) and open circles represent the retention of both alleles. Two commonly deleted regions are designated by sidelines.

FIG. 3 shows partial deletions on chromosome 17q in breast cancers. Solid circles represent the loss of heterozygosity (LOH) and open circles represent the retention of both alleles. Two commonly deleted regions are designated by sidelines.

One of the commonly deleted regions partially overlapped with the region in which the presence of a causative gene was suggested by linkage analyses of families affected with hereditary breast cancer. When 650 cases of sporadic breast cancer were examined for somatic rearrangements by Southern-blot analysis using cosmids located in the overlapping region as probes, it was revealed that a partial region in the DNA of cosmid clone cCI17-904, which had been selected as described above, detected amplification. On closer examination of this alterations, it was found that segments each having about 6–9 kb were connected with each other to form an abnormal repetition consisting of about 4–6 copies. Moreover, a gene encoding a novel protein was isolated by screening cDNA (DNA having a complementary base sequence reverse-transcribed from messenger RNA) libraries by using, as a probe, a restriction fragment of this cosmid clone having a sequence which was conserved among other species. When the sequence structure of this gene was determined and the presence or absence of genomic alterations of this gene in breast cancers was examined, a distinct gene mutation was identified. These results have revealed that deficiency or mutation in this protein and the allelic deletion or mutation of the DNA encoding it deeply participate in the onset of breast and ovarian cancers.

Figure 4A:
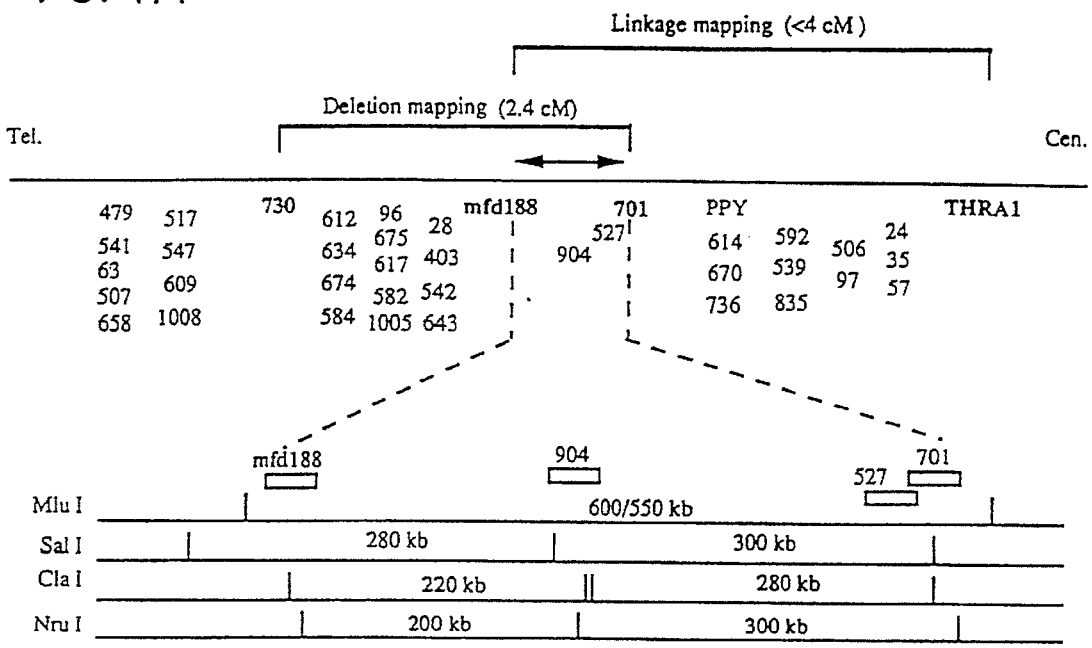
FIGS. 4A and 4B are diagrams showing the process starting with markers on chromosome 17q21.3 and leading to the isolation of the gene, as well as the regions where genomic rearrangements occurred in tumor tissues (hatched boxes). Clone names are designated by clone numbers alone.
Figure 4B:
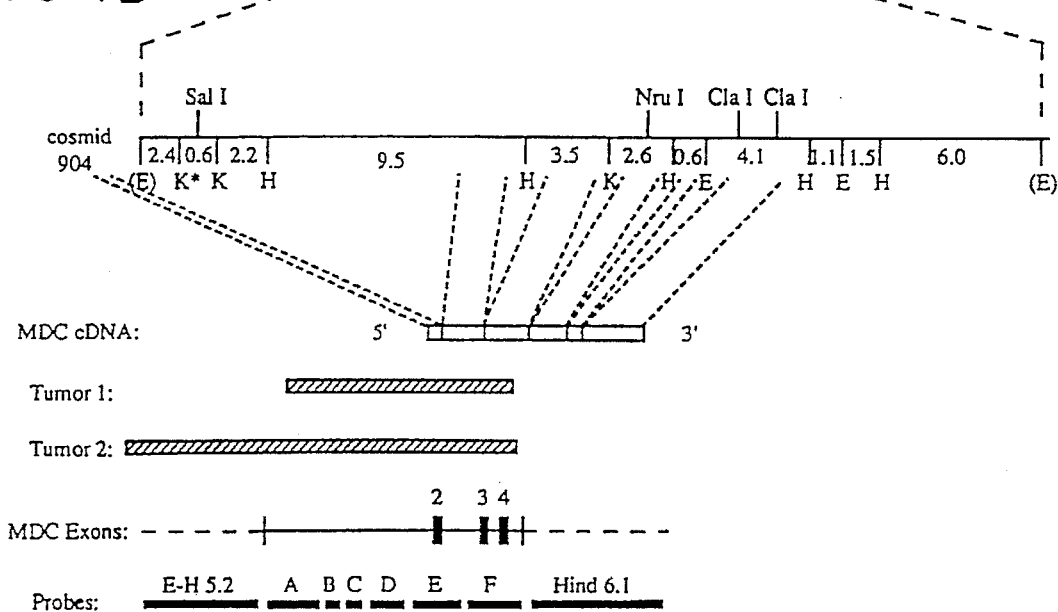

FIGS. 4A and 4B show the above-described process starting with a group of markers and leading to the isolation of the gene, as well as the regions where genomic rearrangements occurred in tumor tissues. Clone names are designated by clone numbers alone.

The present invention is very important in that it can provide methods and materials for solving difficult problems (such as risk diagnosis, early finding, course watching, determination of a treatment plan, and estimation of prognosis) concerning at lease a part of breast and ovarian cancers, for example, by examining the presence or absence of deficiency or mutation in the protein of the present invention or the presence or absence of the allelic deletion or mutation of the gene encoding it, and thereby bring about a marked advance in the technology in this field.

Specifically, the present invention provides (1) an MDC protein which comprises the whole or part of the protein represented by SEQ ID NO:1, SEQ ID NO:2, SEQ ID NO:3 or SEQ ID NO:4, or which consists of a protein substantially equivalent to one comprising the whole or part of the protein represented by SEQ ID NO:1, SEQ ID NO:2, SEQ ID NO:3 or SEQ ID NO:4, (2) a DNA which comprises the whole or part of the DNA represented by SEQ ID NO:5, SEQ ID NO:6, SEQ ID NO:7, SEQ ID NO:8 or SEQ ID NO:9, or which consists of a DNA substantially equivalent to one comprising the whole or part of the DNA represented by SEQ ID NO:5, SEQ ID NO:6, SEQ ID NO:7, SEQ ID NO:8 or SEQ ID NO:9, (3) a plasmid containing the DNA as set forth in the above (2), a transformant carrying the plasmid, i.e., a transformant transformed with the plasmid, and a process for the production of the MDC protein described above, which comprises the steps of culturing the transformant described above and collecting the resulting expression product, (4) an antibody which can bind to the MDC protein described above as an antigen, and (5) a primer, probe or marker which has a DNA sequence comprising a part of the DNA sequence of the DNA as set forth in the above (2), or a DNA sequence complementary to a part of the DNA sequence of the DNA as set forth in the above (2), and a gene analysis method which comprises the step of hybridizing the primer or probe described above to a DNA to be tested.

The term "MDC protein" in this specification means a protein and a peptide (including a oligopeptide and a polypeptide) involved in the definition of the term, "the MDC protein".

Further scope and applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. The present invention will be specifically described hereinbelow.

DETAILED DESCRIPTION OF THE INVENTION (1) Isolation of cDNA clones

Cosmid clones having a DNA derived from human chromosome 17 introduced thereinto can be produced, for example, by extracting chromosomal DNA from a human-mouse hybrid cell line containing a single human chromosome 17 in a mouse genomic background, and incorporating fragments of the chromosomal DNA into a vector such as pWKEX15, according to a method reported by Tokino et al. (Tokino et al., Am. J. Hum. Genet., 48, 258–268, 1991). From among them, clones having an insert derived from the human chromosome can be selected by colony hybridization using the whole human DNA as probe.

The map position of each of the cosmid clones can be determined by FISH. Then, they can be used as markers to construct a high resolution physical chromosome map. Moreover, RFLP markers can be selected on the basis of the fragment length pattern in southern blot analysis (Nakamura et al., Am. J. Hum. Genet., 43, 854–859, 1988). If this map and these RFLP markers are utilized. To examine DNAs obtained from the tumor tissues of cancer patients for LOH (loss of heterozygosity), the commonly deleted region on the chromosome in the tumor tissues can be localized to a very small region near q21 of chromosome 17.

Southern-blot analysis of the DNAs from tumor tissues by using a cosmid clone, whose hybridizable portion is present in this localized region, as a probe makes it possible to select clones having a DNA sequence associated with genomic alterations in the tumor tissues. Moreover, Southern-blot analysis of the chromosomal DNAs of various mammals by using restriction fragments of the cosmid clone as probes makes it possible to select a fragment containing a DNA sequence conserved among other species and involved in fundamental cellular functions. DNA sequences encoding important proteins are often conserved among other species. In fact, many of the hitherto isolated genes for hereditary diseases are conserved among other species (Call, K. M. et al., Cell, 60,509–520, 1990).

If the DNA fragment thus obtained is used as a probe, the cDNA of the gone present in a localized region near q21 of human chromosome 17 can be cloned. The base sequence of this cDNA can be determined by a conventional manner (Maniatis, J. et al., Molecular Cloning 2nd. ed., Cold Spring Harbor Laboratory Press, N.Y. 1989).

In order to confirm that the DNA clones thus obtained are clones of the desired causative gone, their sequences may be used to examine the presence or absence of genomic alterations in cancer patients and the incidence of genomic alterations according to the SSCP method (Orita, M. et al., Genomics, 5, 874–879, 1984; Orita, M. et al., Cell, 60, 509–520, 1990), the RNase protection method (Winter, E., Perucho, M. et al., Proc. Natl. Acad. Sci. USA, 82, 7575–7579, 1985; Myers, R. M. et al., Science, 230, 1242–1246, 1985) and other methods.

(2) Confirmation of the whole structure of the gene

It has been confirmed that the DNA sequences of two cDNAs obtained by the above-described procedure are novel and are those of the DNAs represented by SEQ ID NO:6 and SEQ ID NO:7. The corresponding amino acid sequences have also been identified as those of the proteins represented by SEQ ID NO:2 and SEQ ID NO:3. Moreover, 5'-RACE and RT-PCR have revealed the DNA sequence of the DNA represented by SEQ ID NO:8, and the amino acid sequence of the protein represented by SEQ ID NO:4 has been deduced as one corresponding to the DNA sequence. Furthermore, with regard to genomic DNA, the structure of the DNA represented by SEQ ID NO:9 including introns and exons has been revealed by analyzing the base sequence of the original cosmid clone cCI17-904 and comparing it with the base sequence of the isolated cDNA clone to determine the intron-exon junctions.

By the present inventors, proteins comprising the whole or part of the amino acid sequence of the protein represented by SEQ ID NO:1, which is an amino acid sequence common to all of the above-described proteins, are named MDC proteins and will hereinafter be referred to as MDC proteins.

The term "a part of the protein" means, for example, a polypeptide having or comprising an amino acid sequence consisting of a continuous, at least three, amino acids described in SEQ ID NO:1. The amino acid sequence consists of preferably at least three to five amino acids, still more preferably at least eight or at least eight to ten amino acids, and most preferably at least eleven to twenty amino acids. It is to be understood that polypeptides, each having or comprising an amino acid sequence consisting of, continuously, more than 20 amino acids described in SEQ ID NO:1 can also be used.

As used herein, the term "substantially equivalent" means that, in proteins comprising the whole or part of the amino acid sequence of the protein represented by, for example, SEQ ID NO:1, their amino acid sequences are attended with the replacement, deletion and/or insertion of one or more amino acids, but they can produce an equal effect in research and diagnosis using the proteins comprising the whole or part of the amino acid sequence of the protein represented by, for example, SEQ ID NO:1. Such equivalents also fall within the scope of the present invention and also called as MDC proteins.

The DNA sequence common to all DNAs encoding MDC proteins is represented by SEQ ID NO:5.

A DNA in accordance with the present invention can be utilized in gene analysis and diagnosis. That is, a primer or probe comprising a part of the DNA sequence of the DNA according to the present invention, or comprising a DNA sequence complementary to a part of the DNA sequence of the DNA according to the present invention is used in gene analysis and diagnosis.

Part of the DNA sequence consists of at least six bases, preferably at least 8 bases, still more preferably 10–12 bases and particularly preferably about 15–25 bases. That is, the oligonucleotide used as a primer or probe comprises at least six bases derived from the DNA sequence of the DNA according to the present invention or derived from the DNA sequence complementary to the DNA sequence of the DNA according to the present invention, and, if necessary, other base(s).

In connection with the DNAs of the present invention, the term "substantially equivalent" has the same meaning as described above for the proteins, except that their base sequences have the replacement, deletion and/or insertion of one or more bases.

The introduction of replacement, deletion and insertion mutations into a particular base sequence can be accomplished according to any of conventional methods including those described in F. M. Ausubel et al., "Current Protocols in Molecular Biology", 1987, Chapter 8.

The MDC protein encoded by the DNA according to the present invention, i.e., the MDC protein according to the present invention, can be utilized by using it as an epitope to prepare an antibody. This antibody can be used in experimental and diagnostic reagents. The term "epitope" means an antigenic determinant of a polypeptide and is generally composed of at least 5 amino acids. It is well known that a polypeptide composed of 6 amino acids binds with an antibody, as disclosed in, for example, Published Japanese Translation of International Patent Application No. 60-500684.

(3) Recombinant expression vectors and transformants generated therewith

A transformant can be obtained by incorporating a DNA encoding human MDC protein, which has been obtained by the above-described procedure, or a fragment thereof, into a suitable vector and introducing this vector into suitable host cells. By culturing this transformant with a conventional manner, large amounts of human MDC protein can be obtained from the culture. More specifically, a recombinant expression vector can be produced by linking a DNA encoding a human MDC protein or a fragment thereof on the downstream side of the promoter of a vector suited for its expression according to a well-known method using restriction enzymes and DNA ligase. Usable vectors include, for example, plasmids pRB322 and pUC18 derived from Escherichia coli, plasmid pUB110 derived from Bacillus subtilis, plasmid pRB15 derived from yeast, phage vectors λgt10 and λgt11, and vector SV40 derived from an animal virus. However, no particular limitation is placed on the type of vector used, so long as it can be replicated and amplified in the host. Similarly, no particular limitation is placed on the promoter and terminator, so long as they are compatible with the host used for the expression of the DNA base sequence encoding the human MDC protein. They may be used in any suitable combination depending on the host. The DNA used can be any of DNAs encoding human MDC protein. It is not limited to the base sequences represented by SEQ ID NO:5, SEQ ID NO:6, SEQ ID NO:7, SEQ ID NO:8 and SEQ ID NO:9, but can be any of these DNAs in which a part of the base sequence has undergone replacement, deletion, insertion or a combination thereof, whether intentionally or not. In addition, chemically synthesized DNAs can also be used.

A transformant is generated by introducing the recombinant expression vector thus obtained into a host according to the competent cell method (J. Mol. Biol., 53, 154, 1970), the protoplast method (Proc. Natl. Acad. Sci. USA, 75, 1929, 1978), the calcium phosphate method (Science, 221, 551, 1983), the in vitro packaging method (Proc. Natl. Acad. Sci. USA, 72, 581, 1975) or the virus vector method (Cell, 37, 1053, 1984). The host used can be Escherichia coli, Bacillus subtilis, yeast or animal cells, and the resulting transformant is grown in a suitable medium depending on the host. Usually, the transformant is grown at a temperature of 20° to 45° C. and a pH of 5 to 8, optionally with aeration and stirring. Separation and purification of the MDC protein from the culture may be carried out using a suitable combination of well-known separation and purification techniques. These well-known techniques include salting-out, solvent precipitation, dialysis, gel filtration, electrophoresis, ion exchange chromatography, affinity chromatography, reverse-phase high-performance liquid chromatography and the like.

(4) Preparation of antibodies

Antibodies can be prepared in the usual manner by using an antigen having an epitope part comprising an MDC protein. For example, a polyclonal antibody can be prepared by fully immunizing an animal such as a mouse, guinea pig and rabbit through a plurality of subcutaneous, intramuscular, intraperitoneal or intravenous injections of the antigen described above, collecting blood from this animal, and separating serum therefrom. Commercially available adjuvants may also be used.

A monoclonal antibody can be prepared, for example, by immunizing a mouse with the antigen described above, fusing its spleen cells with commercially available mouse myeloma cells to produce a hybridoma, and collecting an antibody from the culture supernatant of the hybridoma or the ascites of a mouse inoculated with the hybridoma.

The MDC protein which is used as antigen or is used to prepare an antigen need not necessarily have the whole amino acid structure described in SEQ ID NO:1, SEQ ID NO:2, SEQ ID NO:3 or SEQ ID NO:4, but may have a partial structure of the amino acid sequence described in SEQ ID NO:1, SEQ ID NO:2, SEQ ID NO:3 or SEQ ID NO:4. Alternatively, the MDC protein may be a variant or derivative of the MDC protein represented by SEQ ID NO:1, SEQ ID NO:2, SEQ ID NO:3 or SEQ ID NO:4. The antigen may be an MDC protein as such, or a fusion peptide consisting of an MDC protein (incluing peptide) and another peptide. Preparation of the fusion peptide may be carried out according to either biological techniques or chemical synthesis techniques.

These antibodies enable identification and determination of the MDC protein present in human biological specimens and can hence be used as reagents for the diagnosis of cancer, and the like.

The immunological determination of the MDC protein can be made according to any conventional technique. For example, any of the fluorescent antibody technique, the passive agglutination technique and the enzyme antibody technique may be employed.

(5) Gene analysis of human tumor tissues

The biological specimens which can be used for gene analysis include human normal tissues and various types of human tumor %issues, as well as human blood, human body fluids, human secretions and the like. The extraction and preparation of DNA can be carried out, for example, according to the method of Sato et al. (Sato, T. et al., Cancer Res., 50, 7184, 1990).

The presence or absence of mutations of the gene can be analyzed by using, as probes, a restriction fragment of the DNA encoding human MDC protein as provided by the present invention, or by selecting a properly located base sequence from the DNA, synthesizing an oligonucleotide having the selected base sequence and using the oligonucleotide as primer.

These analyses can also detect other alterations, such as insertions and deletions, of the gene in samples.

The base sequences selected for this purpose can be exon portions, intron portions, or junction portions therebetween. It is a matter of course that artificially modified base sequences may be used. When an artificially modified base sequence is used to prepare a primer, the corresponding gene mutation can be detected by the gene analysis.

Analyses can be carried out, for example, by amplifying a partial sequence by PCR using two selected sequences as primers and analyzing the base sequence of the amplification product directly, or by incorporating the amplification product into a plasmid in the same manner as that described above, transforming host cells with this plasmid, culturing the transformed cells, and analyzing the base sequence of the clone thus obtained. Alternatively, the presence or absence of particular mutations of the gene in samples can be directly detected by the use of the ligase chain reaction method (Wu et al., Genomics, 4, 560–569, 1989) and, moreover, the mutant sequence specific PCR method (Ruano and Kidd, Nucleic Acid Research, 17, 8392, 1989; C. R. Newton et al., Nucleic Acid Research, 17, 2503–2517, 1989).

Similarly, using probes containing DNA sequences selected or RNA sequences derived therefrom, point mutations can be detected by the SSCP method or the RNase protection method. Moreover, use of these probes also makes it possible to detect mutations of the gene in samples by Southern hybridization and abnormalities in the expression level of the gene in samples by northern hybridization.

*Escherichia coli* DH5/pBR1 and *Escherichia coli* XL1-Blue MRF'Kan/pCR-5P2, each carrying a plasmid containing the DNA encoding this MDC protein, and *Escherichia coli* 490A/cCI 17-904, carrying a cosmid containing the genomic DNA, were deposited with the National Institute of Bioscience and Human-Technology, Agency of industrial Science and Technology, Ministry of International Trade and Industry on Apr. 28, 1993, Feb. 8, 1994 and Apr. 28, 1993 under accession numbers FERM BP-4286, FERM BP-4555 and FERM BP-4287, respectively.

The MDC proteins and DNAs encoding the MDC proteins according to the present invention are expected to be useful as reagents for cancer research, testing and diagnostic reagents, and therapeutic agents.

EXAMPLES

The present invention will now be described in more detail with reference to the following Examples which should not be considered to limit the scope of the present invention.

Example 1

Isolation of cosmid clones specific for human chromosome 1T and construction of a chromosome map A human-mouse hybrid cell line (GM10331) containing a single human chromosome 17 in a mouse genomic background was selected from among hybrid cells produced by fusing human normal cells with cells of an established mouse cell line and cosmid clones specific for human chromosome 17 were isolated according to the method of Tokino et al. (Tokino et al., Am. J. Hum. Genet., 48, 258–268, 1991). The chromosomal DNA of this hybrid cell line was properly digested with restriction enzyme Sau 3AI and the ends of the fragments thus obtained were treated by partial filling-in with dATP and dGTP. Fragments having a size of 35–42 kb were separated therefrom and inserted in cosmid vector pWEX15 which had previously been digested with restriction enzyme Xho I and similarly treated at its ends by a partial filling-in with dCTP and dTTP. From among the resulting cosmid clones, clones containing human DNA fragments were selected by colony hybridization using $^{32}$P-labeled human chromosomal DNA as probe. Thus, 342 cosmid clones specific for human chromosome 17 were isolated.

With regard to each of these cosmid clones specific for human chromosome 17, the location to which its cosmid DNA hybridize on the chromosome was determined by FISH (Inazawa et al., Genomics, 10, 1075–1078, 1991). Thus, a physical chromosome map for chromosome 17 was constructed (see Tables 1–3 and FIG. 1).

Using DNAs obtained from 6 unrelated individuals, the cosmid clones (cosmid markers), the locations on the chromosome to which their cosmid DNA hybridize had been determined, were examined by a known method (Nakamura et al., Am. J. Hum. Genet., 43, 854–859, 1988) in order to see whether RFLP could be detected or not. The restriction enzyme used was Msp I, Taq I, Bgl II, Pst I, Pvu II, Rsa I or Eco RI. As a result, RFLP was detected in 43 clones (see Tables 4–6). That is, these 43 clones were usable as RFLP markers.

Example 2

Detection of commonly deleted regions the human chromosome 17q in ovarian and breast cancers Tumor tissues were obtained from 94 patients with ovarian cancer and 246 patients with breast cancer who underwent surgery. Corresponding normal tissues or peripheral blood samples were also obtained from the respective patients. DNAs were extracted from these tissues or samples according to a known method (Sato et al., Cancer Res., 50, 7184–7189, 1990). Each DNA was digested with suitable restriction enzymes, and the fragments thus obtained were subjected to 1.0% agarose gel electrophoresis and then Southern transferred to a nylon membrane with 0.1N NaOH/ 0.1M NaCl (Sato et al., Cancer Res., 50, 7184–7189, 1990).

The membranes thus obtained were examined for LOH (loss of heterozygosity) by Southern hybridization (Sato et al., Cancer Res., 50, 7184–7189, 1990) using, as probes, the RFLP markers obtained by the procedure of Example 1 (see Table 7).

TABLE 7

| | | | Ovarian Cancer | | | | | | | | Breast Cancer | |
|---|---|---|---|---|---|---|---|---|---|---|---|---|
| | Chromo- | | No. of patients tested | | | | | | | | No. of | allelic losses/ info- |
| | somal | | ser- | muci- | clear | | allelic losses/infomative cases (%) | | | | patients | mative- |
| Probe | Location | Enzyme | ous | nous | cell | others | serous | mucinous | clear cell | others | tested | cases (%) |
| CI17-316 | q12-21.1 | MspI | 32 | 15 | 12 | 22 | 6/13(46.2) | 0/1(0.0) | 0/3(0.0) | 1/9(11.1) | 85 | 11/37 (29.7) |
| CI17-592 | q21.3 | EcoRI | 14 | 13 | 9 | 15 | 2/3(66.7) | 0/1(0.0) | 0/1(0.0) | 2/4(50.0) | 62 | 8/18 (44.4) |
| CI17-701 | q21.3 | TaqI | 24 | 14 | 13 | 19 | 9/15(60.0) | 2/12(16.7) | 0/7(0.0) | 5/12(41.7) | 232 | 48/138 (34.8) |
| CI17-730 | q21.3 | TaqI | 29 | 15 | 13 | 19 | 6/12(50.0) | 0/4(0.0) | 0/4(0.0) | 2/4(50.0) | 237 | 36/96 (37.5) |
| CI17-507 | q21.3 | MspI | 22 | 14 | 11 | 20 | 6/7(85.7) | 1/3(33.3) | 1/3(33.3) | 2/5(40.0) | 74 | 7/25 (28.0) |
| CI17-533 | q21.3 | TaqI | 22 | 13 | 11 | 16 | 6/11(54.5) | 3/9(33.3) | 1/7(14.3) | 4/9(44.4) | 230 | 25/93 (26.9) |
| CI17-7 | q22 | PvuII | 21 | 8 | 9 | 15 | 4/5(80.0) | 0/1(0.0) | 0/3(0.0) | 1/3(33.3) | 86 | 14/41 (34.1) |
| CI17-489 | q23 | MspI | 26 | 13 | 11 | 21 | 5/5(100.0) | 0/2(0.0) | 0/3(0.0) | 3/8(37.5) | 75 | 10/31 |

TABLE 7-continued

| | | | Ovarian Cancer | | | | | | | | Breast Cancer | |
| --- | --- | --- | --- | --- | --- | --- | --- | --- | --- | --- | --- | --- |
| | Chromo- | | No. of patients tested | | | | allelic losses/infomative cases (%) | | | | No. of | allelic losses/ info- mative- |
| Probe | somal Location | Enzyme | ser- ous | muci- nous | clear cell | others | serous | mucinous | clear cell | others | patients tested | cases (%) |
| CMM8G | q23 | TaqI | 28 | 13 | 10 | 17 | 6/17(35.3) | 1/8(12.5) | 0/6(0.0) | 2/10(20.0) | 79 | (32.3) 12/49 |
| CI17-516 | q25.1 | TaqI | 29 | 14 | 14 | 21 | 6/17(35.3) | 1/10(10.0) | 0/7(0.0) | 6/11(54.5) | 84 | (24.5) 9/31 |
| CI17-710 | q25.3 | TaqI | 18 | 13 | 10 | 12 | 4/8(50.0) | 3/8(37.5) | 0/6(0.0) | 3/7(42.9) | 80 | (29.0) 13/45 (28.9) |

A total of 84 among 94 ovarian tumors were informative for at least one locus, and 33 (39.3%) of them showed LOH for at least one locus on chromosome 17q. Among 246 breast tumors examined, 214 were informative for at least one locus, and 88 (41.4%) showed LOH for at least one locus on chromosome 17q.

From the above results, the instances which were informative for two or more loci and exhibited both loss of heterozygosity at a locus and retaining of heterozygosity at other locus on chromosome 17q were summarized.

As a result, two commonly deleted regions were found in 8 ovarian cancers (see FIG. 2). One of them was a region lying between markers CI17-316 (17q12-21.1) and CI17-507 (17q21.3), and the other was a region distal to the marker CI17-516 (17q25.1).

Similarly, two commonly deleted regions were found in 35 breast cancers (see FIG. 3). One of them was a region lying between markers CI17-701 (17q21.3) and CI17-730 (17q21.3), which was also found in the ovarian cancers but was more narrowly localized. The other was a region lying on the terminal side of marker CI17-516 (17q25.1), which was also the region where a deletion was observed in the ovarian cancers.

Of the two commonly deleted regions defined by the above-described deletion mapping, the region flanked by markers CI17-701 and CI17-730 was found to lie close to the 17q21 region which showed an intimate correlation with the onset of cancer on the basis of the results of linkage mapping studies on hereditary breast cancer and ovarian cancer (Hall et al., Am. J. Hum. Genet., 50, 1235–1242, 1992). The length of this region (i.e., the genetic distance between the two markers) was estimated to be 2.4 cM by linkage analysis (Lathtop et al., Am. J. Hum. Genet., 37, 482–498, 1985; Donis-Keller et al., Cell, 51, 319–337, 1987).

Example 3

Isolation of cosmid clones contained in the minimal localized region

Since it has been shown that the region localized on the basis of the results of linkage mapping is a region lying between markers THRA1 and Mfd188 on 17q21 (Hall et al., Am. J. Hum. Genet., 52, 1235–1242, 1992; Bowcock, A. M. et al., Am. J. Hum. Genet., 52, 718–22, 1993), an attempt was made to determine the relative order of these markers and markers CI17-701 and CI17-730 and thereby combine the mapping information obtained by two different strategies. The relative order of the markers was determined by a two-color FISH method newly developed by the present inventors. This method is a modification of FISH in which a highly extended chromosome preparation obtained by synchronization of the cells is used to enhance the degree of fineness and, moreover, probes labeled with fluorescent materials having different colors are used. This method makes it possible to determine the relative order of markers very close to each other.

As a result, it was found that marker Mfd188 lies between markers CI17-701 and CI17-730 and marker THRA1 lies on the centromeric side of CI17-701 (see FIG. 4A). That is, the region associated with hereditary breast cancer as localized by linkage mapping and the commonly deleted region in sporadic breast cancers as localized by deletion mapping overlapped each other and the overlapping minimal region was flanked by markers CI17-701 and Mfd188 (see FIG. 4A). When a physical map of this region was constructed by pulsed-field gel electrophoresis, the length of the overlapping region was greatly narrowed down to about 500 kb.

Furthermore, of the cosmid clones obtained by the procedure of Example 1, 37 clones localized to 17q21.3 and three known markers, THRA1, Mfd188 and PPY, were selected and used for fine mapping of this chromosomal region by two-color FISH. As a result, 15 cosmid clones were located in a region flanked by markers CI17-701 and CI17-730. Of these, two cosmid clones, CI17-527 and CI17-904, were found to lie in the above-described overlapping region (see FIG. 4A).

Example 4

Detection of genomic alterations in breast cancers

Figure 5A:
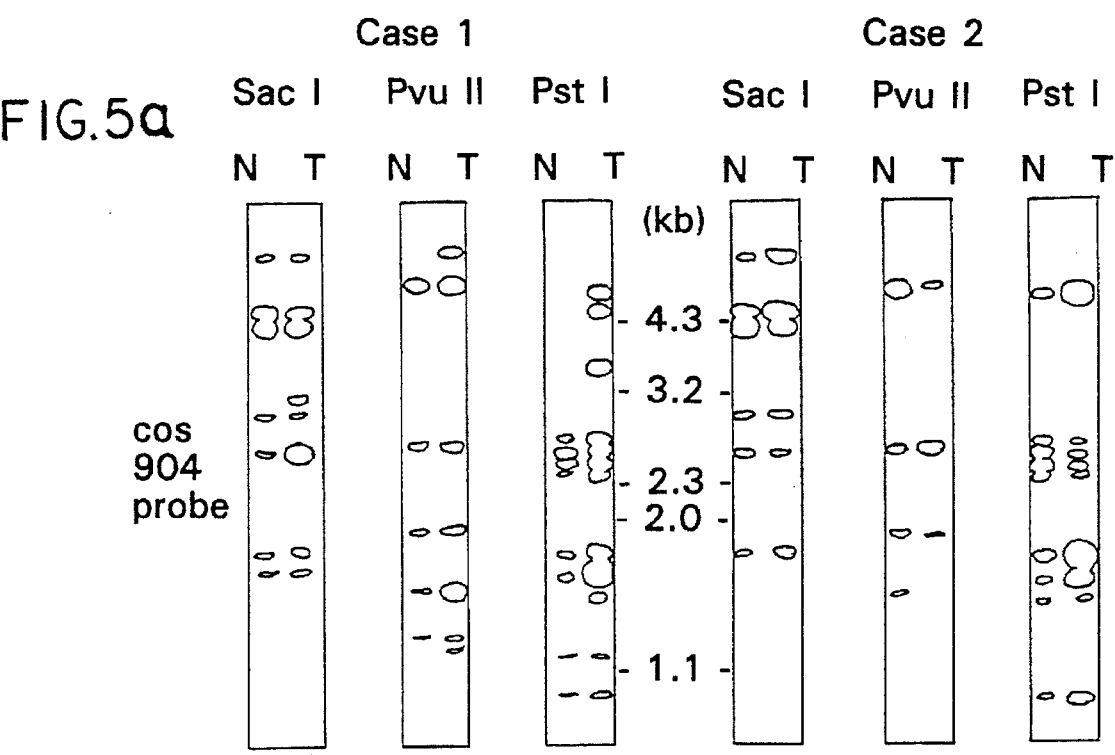
FIGS. 5(a), 5(b), 6 and 7 are diagrams showing the detection of genomic rearrangements in breast cancers by Southern-blot analysis. Symbols N and T represent DNAs from normal tissue and tumor tissue, respectively.
Figure 5B:
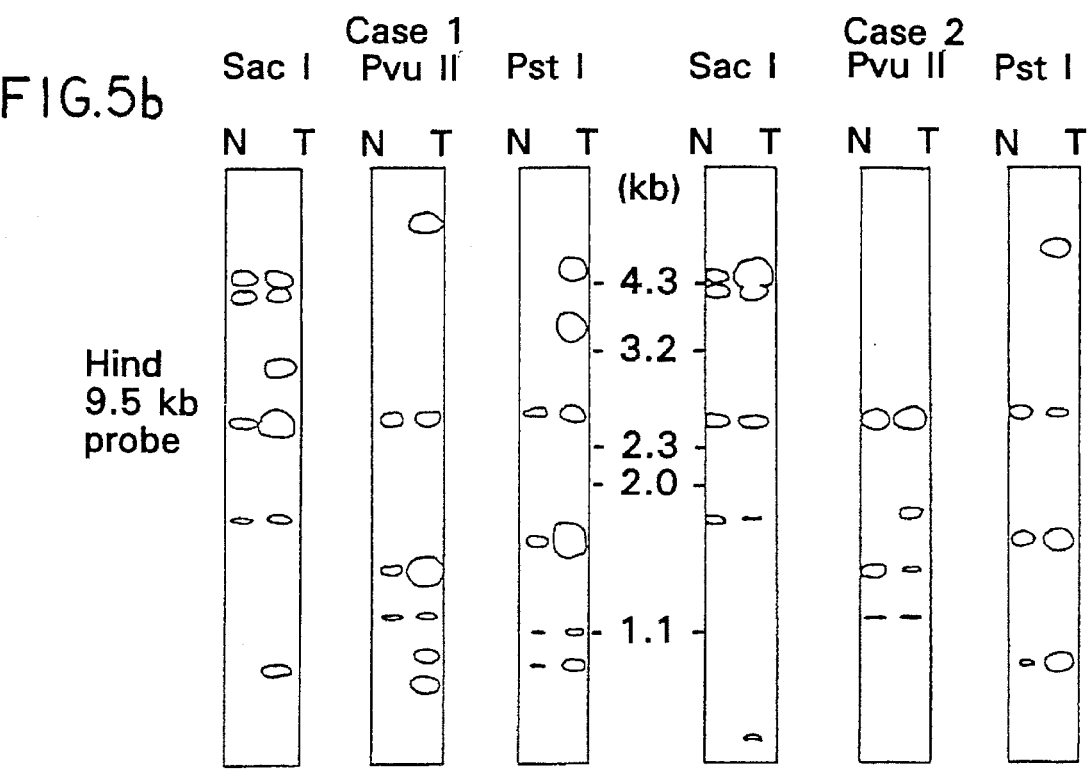

Of the overlapping region of about 500 kb, about 150 kb has already been covered by four cosmid clones CI17-701, CI17-527, CI17-904 and Mfd188. Accordingly, an attempt was first made to screen restriction (Sac I, Pvu II or Pst I) fragments of the DNAs from the tumor tissues of 650 sporadic breast cancers by Southern-blot analysis using the DNAs of these cosmid clones or fragments thereof as probes and thereby detect gross structural genomic alterations (so-called genomic rearrangements), such as deletion, duplication, amplification and translocation, having occurred in the tumor cells. As a result, when the DNA of CI17-904 or its 9.5 kb Hind III fragment (see FIG. 4B) was used as probe, genomic rearrangements were detected in the tumor tissues of two breast cancers (see FIG. 5, a and b). These genomic rearrangements occurred only in the tumor tissues, exhibiting extra bands of different size which were not observed in normal tissues. In addition, the intensities of some bands were increased. That is, a gene amplification occurred in a definite DNA region corresponding to (i.e., hybridizable) this probe. In one case among the above-mentioned two breast cancers, no gene amplification was detected when Southern-blot analysis of the Sac I fragments of DNA from the breast cancer tissue was carried out by using the E-H5.2 or Hind6.1 fragment adjacent to the 9.5 kb Hind III fragment (see FIG. 4B) as a probe (see FIG. 6, Case 1). This indicates that the gene amplification in this case occurred within the region corresponding to the 9.5 kb Hind III fragment and was a 4- to 5-fold amplification.

Figure 7:
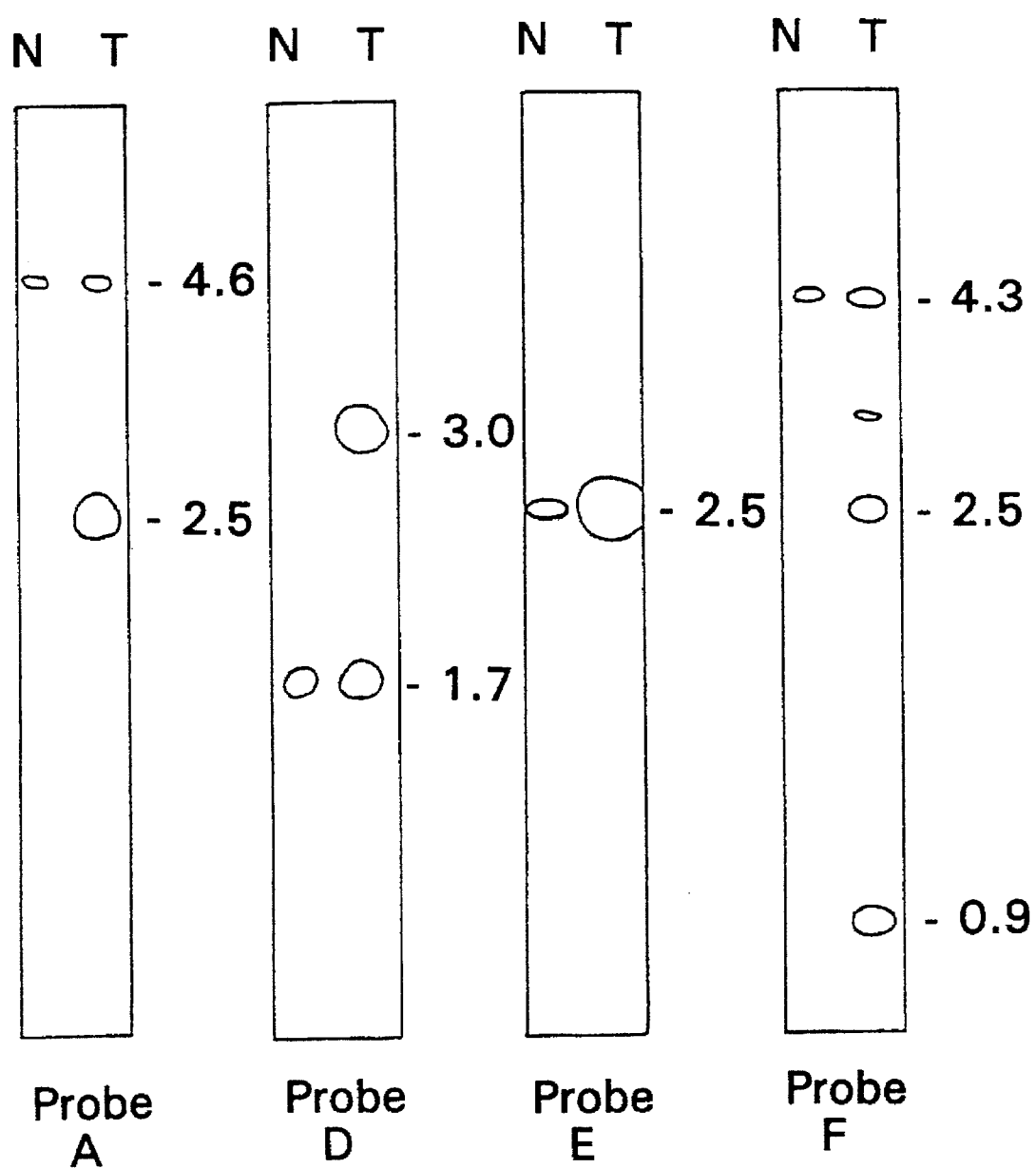

For the purpose of closer examination, Southern-blot analyses of the Sac I fragments of DNA from the breast cancer tissue were carried out using each of six Sac I fragments derived from the 9.5 kb Hind III fragment, A, B, C, D, E and F (see FIG. 4B), as probe. As a result, amplified bands of abnormal size were observed at 2.5 kb with probes A and B, at 3.0 kb with probes B, C and D, at 2.5 kb with probes E and F, and at 0.9 kb with probe F (see FIG. 7).

Figure 6:
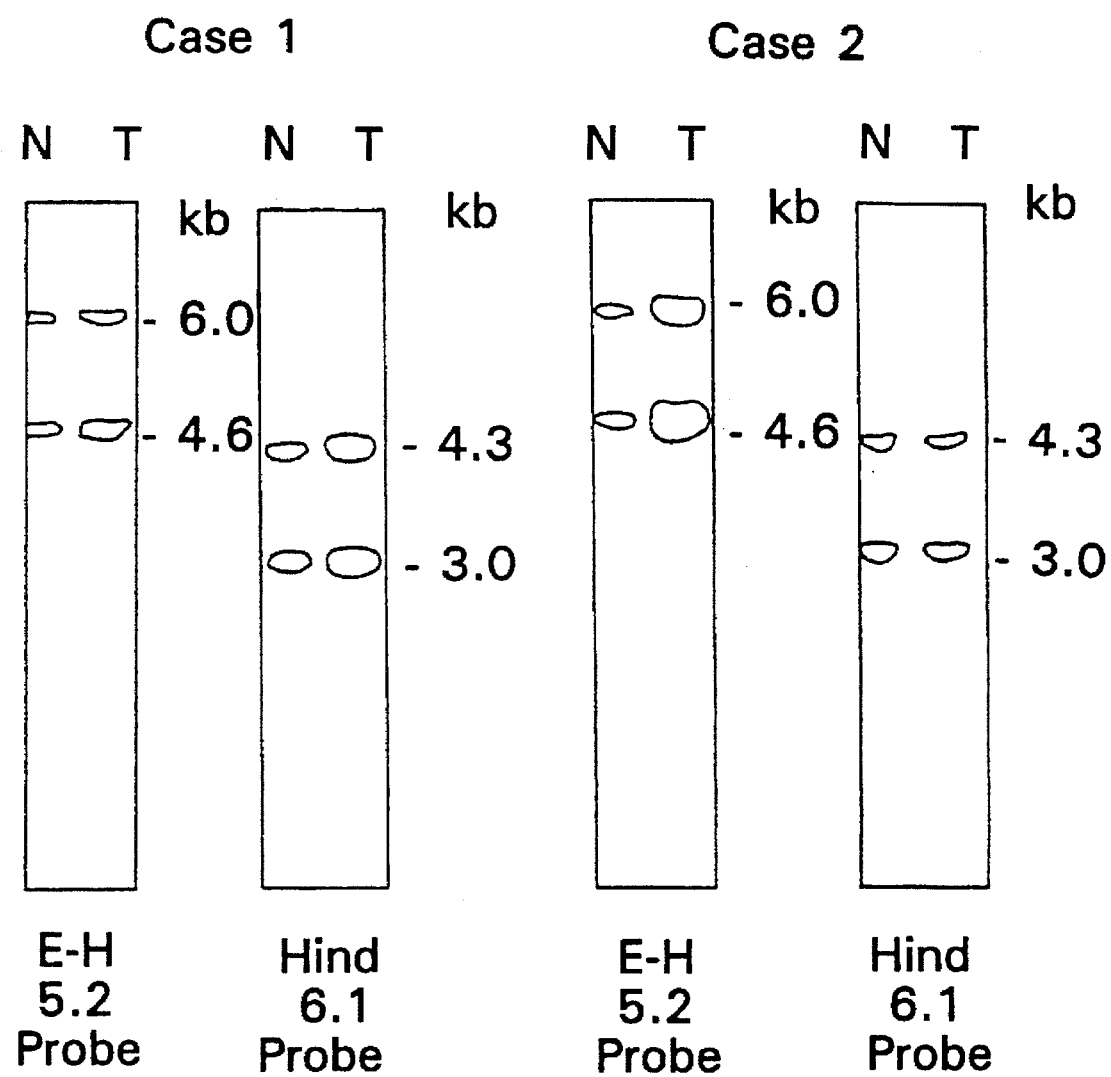

In the other case, gene amplification was detected when Southern-blot analysis of the Sac I fragments of DNA from the breast cancer tissue was carried out by using the E-H5.2 fragment as a probe (see FIG. 6, Case 2). However, no gene amplification was detected when the Hind6.1 fragment was used as a probe (see FIG. 6, Case 2). In this case, when the E-H5.2 fragment was used as a probe, only an amplification was observed without being attended with any band of abnormal size. This indicates that the gene amplification in this case occurred in a segment extending from within the region corresponding to the 9.5 kb HindIII fragment to the outer (telomeric) side of the region corresponding to the E-H5.2 fragment.

Example 5

Isolation of cDNA and determination of its structure

In order to isolate an expressed gene in or near the region where genomic rearrangements were detected in the two breast cancers, DNA fragments containing DNA sequences involved in fundamental cellular functions and conserved among other species were selected from DNA fragments of cosmid clone CI17-904. Specifically, each of the DNA fragments of cosmid clone CI17-904 was used as probe in Southern blot hybridization analyses of DNA fragments from cow, pig, mouse, rat and chicken. As a result, the 3.5 kb Hind III-Ksp I fragment (see FIG. 4B) of cosmid clone CI17-904 hybridized to DNAs from cow, pig, mouse and rat and showed strong conservation.

Using this 3.5 kb Hind III-Ksp I fragment as a probe, human cDNA libraries derived from five different organs (i.e., mammary gland, breast cancer cell line, fetal brain, cerebrum and cerebellum) were screened. Thus, the longest cDNA was cloned from the cerebellar cDNA library. This cDNA hybridized to the 3.5 kb Hind III-Ksp I fragment of cosmid clone CI17-904 and a plurality of adjoining restriction fragments, and extended over a region of more than 20 kb on the chromosome.

Analysis of the base sequence of this cDNA revealed that it consisted of 2923 base pairs (bp) and was a novel DNA base sequence containing a 5'-untranslated region of 27 bp, a coding region of 1575 bp, a 3'-untranslated region of 1306 bp, and a poly(A) tail of 15 bp (see SEQ ID NO:6). The open reading frame contained in this cDNA sequence encoded a novel protein (MDC protein: see SEQ ID NO:2). An in-frame termination codon was present immediately upstream of the first ATG of the open reading frame. A polyadenylation signal, AATAAA, was observed about 20 bp upstream from the polyadenylation site.

Example 6

Determination of the structure of genomic DNA

In order to clarify the structure of the genomic DNA corresponding to the cDNA obtained in Example 5, cosmid clone CI17-904 was examined to determine the base sequences of portions containing the base sequence of this cDNA and portions surrounding them. Then, the sequences of both were compared to determine the exon-intron junctions. As a result, the sequence structure of a novel DNA containing 25 exons corresponding to the cDNA obtained in Example 5 was clarified (see SEQ ID NO:9). Thus, it was shown that these 25 exons are of relatively small size and present over about a 20 kb region of the chromosome.

Example 7

Detection of alterations in the exon structure of the gene in breast cancers

From the structure of the DNA containing exons/introns as clarified in Example 6, it has become apparent that exons 2, 3 and 4 are present in the sequence region of the probe (the 9.5 kb Hind III fragment of cosmid clone CI17-904) with which alterations were detected in the tumor tissues of two breast cancers as described in Example 4. More specifically, exon 2 is present in the sequence region of probe E, and exons 3 and 4 are present in the sequence region of probe F (see FIG. 4B). Accordingly, it is believed that the gene rearrangements involving the 9.5 kb Hind III fragment region as described in Example 4 disrupt the normal exon structure in the region containing the three exons of the gene. In order to confirm this, the chromosomal DNAs from the tumor tissues of the above-described two breast cancers were examined by Southern-blot analysis using probes having DNA sequences corresponding to exons 2, 3 and 4. Thus, amplified bands of abnormal size were observed similarly to the previously described results obtained with probe E or F (see FIG. 7).

Example 8

Tissue specificity of gene expression mRNAs derived from various human tissues (brain, heart, kidney, liver, lung, pancreas, placenta, skeletal muscle, colon, peripheral blood lymphocyte, ovary, small intestine, spleen, testis and thymus) were examined by northern-blot analysis using the cDNA obtained in Example 5 as a probe. As a result, the strongest expression was observed in the brain, and a weak expression in the heart, ovary and testis.

Moreover, amplification by RT-PCR (reverse-transcriptase PCR) was performed to detect a weaker expression. Specifically, using random hexamers as primers, single-stranded cDNAs were synthesized from mRNAs derived from various human tissues under the action of reverse transcriptase. Then, PCR amplification from these templates was performed using primers BC09 and BC012 having sequences derived from the sequences of exons 21 and 23, respectively, which had been revealed in Example 6. As a result, a PCR product having the expected size was observed mainly in tissues of the central nervous system (cerebrum, cerebellum and fetal brain) and in endocrine or reproductive organs (testis, ovary, mammary gland, adrenal gland, thymus and pancreas).

The sequences of the primers used are as follows:

| | |
|---|---|
| BC09 | 5'-GCACCTGCCCCGGCAGT-3'<br>(SEQ ID NO: 10)<br>(coding strand, corresponding to base numbers 1764–1780 of SEQ ID NO: 6) |
| BC012 | 5'-CCAGGACAGCCCCAGCGATG-3'<br>(SEQ ID NO: 11)<br>(antisense strand, corresponding to base numbers 1976–1957 of SEQ ID NO: 6) |

Example 9

Direct sequencing of mRNA by RT-PCR mRNAs derived from human fetal brain and human testis were amplified by RT-PCR using primer GMA701 having a sequence derived from the sequence on exon 19 and primer GMB704 having a sequence derived from the sequence on exon 21. Then, the base sequences of the amplified DNAs were directly determined using primer GMA702 or GMB703. As a result, a sequence, wherein 10 bases (base numbers 1512–1521) were deleted from the cerebellar cDNA sequence of SEQ ID NO:6 obtained in Example 5, was found, which revealed the expression of mRNA corresponding to the DNA sequence of SEQ ID NO:7. Both the fetal brain and testis mRNAs gave the identical result. The open reading frame contained in the cDNA sequence of SEQ ID NO:7 encodes an MDC protein (see SEQ ID NO:3) composed of 670 amino acids.

This seems to be caused by the alternative RNA splicing at the initiation of exon 20 which starts with base number 6083 instead of base number 6078 on the genomic DNA of SEQ ID NO:9. Such a variation of splicing is also known from, for example, a report by Oda et al. [Biochem. Biophys. Res. Commun., 193, 897–904 (1993)]. As a result, the amino acid sequences encoded by the cDNA of SEQ ID NO:6 and the cDNA of SEQ ID NO:7 differ from each other at and after that site (see SEQ ID NO:2 and SEQ ID NO:3). Specifically, the cDNA of SEQ ID NO:6 produces a termination codon within exon 20, whereas the reading frame is shifted in the cDNA of SEQ ID NO:7 so as to cause the open reading frame to continue to a more downstream position.

The sequences of the primers used in PCR and DNA sequencing are as follows:

| | |
|---|---|
| GMA701 | 5'-GGCTGCTGATCGCTTCTGCTAC-3'<br>(SEQ ID NO: 12)<br>(coding strand, corresponding to base numbers 1413–1434 in SEQ ID NO: 6) |
| GMA702 | 5'-GAGAAGCTGAATGTGGAGGG-3'<br>(SEQ ID NO: 13)<br>(coding strand, corresponding to base numbers 1435–1456 in SEQ ID NO: 6) |
| GMB703 | 5'-GTCAGAGCCGTCCGCCAGC-3'<br>(SEQ ID NO: 14)<br>(antisense strand, corresponding to base numbers 1675–1657 in SEQ ID NO: 6) |
| GMB704 | 5'-GCCATCCTCCACATAGCTCAGG-3'<br>(SEQ ID NO: 15)<br>(antisense strand, corresponding to base numbers 1696–1655 in SEQ ID NO: 6) |

Example 10

Amplification of the 5'-terminal sequence by RACE

In order to obtain the full-length cDNA represented by SEQ ID NO:7, PCR amplification of the 5'-cDNA terminus (5'-RACE; Frohman, et al., Proc. Natl. Acad. Sci. USA, 85, 8998–9002, 1988; Belyavski, et al., Nucleic Acid Res., 17, 2919–2932, 1988) was performed. Using specific oligomer SGN012 as a primer, together with a commercially available synthesis kit, a single-stranded cDNA was synthesized from 2 μg of poly A(+) RNA derived from human brain (manufactured by Clontech). Then, 5'-RACE was performed using a commercially available kit based on the method of Edwards et al. for linking an anchor oligomer to an end of a single-stranded cDNA (Nucleic Acid Res., 19, 5227–5232, 1991). As a result of PCR using the anchor oligomer of the kit and another specific oligomer SGN011 as primers, an amplification product of about 580 bp was detected by electrophoresis.

This amplification product was extracted from the electrophoretic gel, purified, inserted in the Srf I cleavage site of plasmid vector pCR-Script (manufactured by Stratagene), and cloned. Plasmid DNA was purified from each clone and its base sequence was determined. One of the clones, pCR-5P2, had a cDNA insert of 501 bp beginning with ATG, next to the sequence of the anchor oligomer. The base sequence of the insert extending from base number 315 onward coincided exactly with the base sequence of SEQ ID NO:7 extending from base number 45 (the initiation site of exon 2) onward, excepting one base which will be mentioned below. Furthermore, as far as the reading frame is concerned, that of pCR-5P2 beginning with the first ATG corresponded with the polypeptide encoded by the cDNA of SEQ ID NO:7. The N-terminal region of the polypeptide sequence thus obtained encoded a signal peptide comprising a series of hydrophobic amino acids.

RT-PCR was performed in order to confirm that the above 5'-terminal sequence obtained by 5'-RACE was truly linked, on mRNA, to the sequence of SEQ ID NO:7 extending from base number 45 onward. Using random hexamers as primers, single-stranded cDNAs were synthesized from poly A(+) RNAs derived from human brain, fetal brain, ovary and testis (manufactured by Clontech). Then, the cDNA template were amplified by PCR using an oligomer (SGN013) having the first 20-base sequence of pCR-5P2 as a sense primer and SGN011 or SGN012 as an antisense primer. As a result, the expected amplification product (about 500 bp for SGN013/SGN011 and about 750 bp for SGN013/SGN012) was detected by electrophoresis with every tissue RNA used.

Thus, it was confirmed that the 5'-terminal sequence of pCR-5P2 obtained by 5'-RACE was linked, on mRNA, to the sequence of SEQ ID NO:7 extending from base number 45 onward, resulting in the construction of a cDNA represented by SEQ ID NO:8. The open reading frame of the cDNA of SEQ ID NO:8 encodes an MDC protein composed of 769 amino acids (see SEQ ID NO:4).

The sequences of the specific oligomers used are as follows:

| | |
|---|---|
| SGN011 | 5'-GATGTAAGTCAAGTTCCCATCAGAGA-3'<br>(SEQ ID NO: 16)<br>(antisense strand, corresponding to base numbers 231–206 in SEQ ID NO: 7) |
| SGN012 | 5'-AACAGCTGGTGGTCGTTGATCACAA-3'<br>(SEQ ID NO: 17)<br>(antisense strand, corresponding to base numbers 485–461 in SEQ ID NO: 7) |
| SGN013 | 5'-ATGAGGCTGCTGCGGCGCTG-3'<br>(SEQ ID NO: 18)<br>(coding strand, corresponding to base numbers 1–20 in SEQ ID NO: 8) |

The above-mentioned one base in the SEQ ID NO:8 after the initiation site of exon 2, differing from one in the SEQ ID NO:6 or SEQ ID NO:7, is the fourth base from the initiation site of exon 2, i.e., the C at the base number 318 in the SEQ ID NO:8. The corresponding base in the SEQ ID NO:6 or the SEQ ID NO:7 is the base A at the base number 48. The base C at the base number 318 in the SEQ ID NO:8 codes His at the amino acid number 106 in the SEQ ID NO:4. The base A at the base number 48 in the SEQ ID NO:6 or the SEQ ID NO:7 codes Gln at the amino acid number 7 in the SEQ ID NO:2 or the SEQ ID NO:3. This fact reflects polymorphism.

An amino acid sequence common to these three variant MDC proteins (SEQ ID NO:2, SEQ ID NO:3 and SEQ ID NO:4) is a sequence composed of 488 amino acids (see SEQ ID NO:1), and a DNA sequence encoding this portion is also a common sequence (see SEQ ID NO:5).

Example 11

Homology with known proteins

The amino acid sequences of MDC proteins showed homology with a family of snake venom hemorrhagic proteins including HR1B (Takeya et al., J. Biol. Chem., 265, 16068–16073, 1990), prorhodostomin (Au et al., Biochem. Biophys. Res. Commun., 181, 585–593, 1991) and protrigramin (Neeper et al., Nucleic Acid Res., 18, 4255, 1990).

They also showed homology with the guinea pig sperm surface protein PH30 (Blobel et al., Nature, 356, 248–252, 1992) and the rat or monkey epididymis protein EAPI (Perry et al., Biochem. J., 286, 671–675, 1992).

The homology of these proteins with the MDC proteins represented by SEQ ID NO:2 (524 amino acids) and SEQ ID NO:4 (769 amino acids) is indicated by the following "percent identity/number of amino acids in the tested region". The values for SEQ ID NO:2 are given on the left side and those for SEQ ID NO:4 on the right side.

| | | |
|---|---|---|
| HR1B | 32.5/335 | 32.2/379 |
| prorhodostomin | 29.0/420 | 29.0/420 |
| protrigramin | 27.7/430 | 28.1/438 |
| PH30b | 38.1/147 | 30.8/302 |
| EAP1 (rat) | 36.0/364 | 33.1/475 |
| EAP1 (monkey) | 30.4/503 | 29.9/599 |

Example 12

Generation of transformants

A DNA fragment encoding a part of the MDC protein represented by SEQ ID NO:2 was amplified from the DNA (SEQ ID NO:6) encoding the MDC protein (SEQ ID NO:2) by PCR using primers SGN006 and SGN008. The sequences of the primers used are as follows.

| | |
|---|---|
| SGN006 | 5'-CACAGATCTGGGGGCATATGCTCCCTG-3' (SEQ ID NO: 19) (coding strand, corresponding to base numbers 766–783 in SEQ ID NO: 6) |
| SGN008 | 5'-AACAAGCTTCTACTGATGTCTCCCACC-3' (SEQ IDNO: 20) (antisense strand, corresponding to base numbers 1602–1585 in SEQ ID NO: 6; the underline designating a termination codon.) |

For purposes of vector construction, the 5'-terminal of these primers are provided with Bgl II and Hind III cleavage site sequences, respectively.

The PCR amplification product was separated by agarose gel electrophoresis and cleaved with Bgl II and Hind III. The resulting DNA fragments encoding a part of the MDC protein was combined with vector pMAL-c2 (manufactured by New England Biolabs) which had previously been cleaved with Bam HI and Hind III to construct plasmid pMAL-MDC(C1).

Similarly, the same DNA fragment was combined with vector pQE-13 (manufactured by Diagen) which had previously been cleaved with Bam HI and Hind III to construct plasmid pH6-MDC(C1).

Furthermore, a DNA sequence downstream from the Bam HI cleavage site (base number 1483 in SEQ ID NO:6) was removed from the MDC protein encoding region of pMAL-MDC(C1) by cleaving pMAL-MDC(C1) with Bam HI and Hind III, and recombining it after the formation of blunt ends. This resulted in the construction of plasmid pMAL-MDC(dC1), which mediates expression of a polypeptide with an amino acid sequence common to two variant MDC proteins (SEQ ID NO:2 and SEQ ID NO:3).

Since the fragment incorporated into vector pMAL-c2 is expressed as a fusion protein having a maltose-binding protein (MBP) on the N-terminal side, this fusion protein was purified by affinity chromatography using an amylose column. On the other hand, since the fragment incorporated into vector pQE-13 is expressed as a fusion protein having a peptide (His 6) composed of six histidine residues on the N-terminal side, this fusion protein was purified by affinity chromatography using a metal chelate column.

Several transformants were obtained by transforming E. coli JM109 with each of plasmids pMAL-MDC(C1), pMAL-MDC(dC1) and pH6-MDC(C1) and selecting for ampicillin resistance.

Example 13

Expression and purification of recombinant MDC proteins

Each of the transformants obtained in Example 12 was grown and the resulting recombinant MDC fusion protein was extracted and purified from the culture.

Specifically, 100 ml of LB medium (1% polypeptone, 0.5% yeast extract, 1% NaCl) was inoculated with each transformant and incubated overnight at 37° C. with shaking. The culture was diluted 10-fold with LB medium previously warmed to 37° C. and incubated for additional 30–90 minutes to obtain a culture in the logarithmic growth phase. To 1 liter of the culture was added IPTG (isopropyl-β-D-thiogalactopyranoside) so as to give a final concentration of 1 mM. This culture was incubated for 3–4 hours and then centrifuged to collect the cells therefrom.

In the case of a transformant of plasmid pMAL-MDC(C1) or pMAL-MDC(dC1), the cells were suspended in 10 ml of a column buffer (20 mM Tris-HCl, pH 7.4, 200 mM NaCl) and disintegrated by sonication. Since the recombinant MDC fusion protein was present in the insoluble fraction of the disintegrated cell suspension, this was separated by centrifugation and dissolved in a denaturing buffer (8M urea, 20 mM Tris-HCl, pH 8.5, 10 mM dithiothreitol). Then, this solution was dialyzed against the column buffer and centrifuged to collect a supernatant soluble fraction. The dialyzed insoluble fraction was further denatured, dialyzed and centrifuged repeatedly to collect additional supernatant soluble fractions. The combined soluble fraction was applied to an amylose column (manufactured by New England Biolabs), which was washed with the column buffer and eluted with the column buffer containing 10 mM maltose. The eluted fractions were analyzed by absorptiometry at 280 nm and SDS-polyacrylamide electrophoresis (with Coomassie Blue staining), and combined into fractions. As a result, a fraction in which the desired MBP (maltose binding protein) fusion protein (about 68 Kd) was detected as a principal band was obtained for each of the transformants generated with plasmids pMAL-MDC(C1) and pMAL-MDC(dC1). The yield was 46.4 mg and 10.0 mg (when an $OD_{280}$ of 1 was taken as 1 mg/ml), respectively. These fusion proteins will hereinafter be referred to as MBP-MDC(C1) and MBP-MDC (dC1), respectively.

Similarly, in the case of a transformant of plasmid pH6-MDC(C1), the cells were suspended in 10 ml of a sonication buffer (10 mM sodium phosphate, pH 8.0, 200 mM NaCl) and disintegrated by sonication. Since the recombinant MDC fusion protein was present in the insoluble fraction of the disintegrated cell suspension, this was separated by centrifugation and dissolved in buffer A (6M guanidine hydrochloride, 100 mM $NaH_2PO_4$, 10 mM Tris-HCl, PH 8.0). Then, this solution was centrifuged to collect a supernatant soluble fraction, which was applied to a Ni-NTA column (manufactured by Diagen). This column was washed with buffer A and then buffer B (8M urea, 100 mM $NaH_2PO_4$, 10 mM Trim-HCl, pH 8.0), and eluted stepwise with buffer C (8M urea, 100 mM $NaH_2PO_4$, 10 mM Tris-HCl, pH 6.3), buffer D (8M urea, 100 mM $NaH_2PO_4$, 10 mM Tris-HCl, pH 5.9), buffer E (8M urea, 100 mM $NaH_2PO_4$, 10 mM Tris-HCl, pH 4.5) and buffer F (6M guanidine hydrochloride, 200 mM acetic acid). The eluted fractions were analyzed by absorptiometry at 280 nm and SDS-polyacrylamide electrophoresis (with Coomassie Blue staining), and combined into fractions. As a result, a fraction in which the desired His6 fusion protein (about 34 Kd) was detected as a single band was obtained from the effluent resulting from elution with buffer F. The yield was 51.9 mg (when an $OD_{280}$ of 1 was taken as 1 mg/ml). This fusion protein will hereinafter be referred to as His6-MDC(C1).

Example 14

Preparation of a monoclonal antibody and a rabbit polyclonal antibody

The three recombinant fusion proteins, His6-MDC(C1), MBP-MDC(dC1) and MBP-MDC(C1), obtained in Example 13 were used as an immunizing antigen, an antigen for antibody purification and screening, and a standard antigen for measurement, respectively.

An anti-MDC protein specific monoclonal antibody was prepared by immunizing a mouse with His6-MDC(C1). Specifically, a solution of His6-MDC(C1) (500–1000 µg/ml) in 3M urea/PBS was mixed with a complete adjuvant at a ratio of 1:1, and this mixture was injected into the peritoneal cavity of a mouse at a dose of 100 µg per animal. This injection was repeated 4–6 times at intervals of 2 weeks. After completion of the immunization, hybridomas were produced by fusing P3U1 cells with B cells in the presence of PEG1500. Then, hybridomas productive of an anti-MDC protein specific antibody were selected by monitoring the antibody titer in the culture supernatant.

In order to measure the antibody titer, a first reaction was effected by adding 100 µl of the culture supernatant to a polystyrene cup having a solid phase formed from the MBP-MDC(dC1) fusion protein obtained in Example 13 (5 µg/ml). After washing, a second reaction was effected by the addition of anti-mouse IgG HRP (horse-raddish peroxidase). After washing, a color reaction (third reaction) was effected by the addition of an enzyme substrate solution [i.e., a mixed solution of hydrogen peroxide and ABTS [2,2'-azino-bis(3-ethylbenzothiazoline-6-sulfonic acid)]], and the produced color was monitored.

The hybridomas were grown on a 96-well multi-plate and screened by means of HAT medium. After about 2 weeks, clones reacting specifically with the antigen were selected by measuring the antibody titer in the culture supernatant. As a result of further cloning, 3 clones (G1-5A2-2C8, G2-2F2-3D11 and G2-2D10-3F5) were established as antibody-producing hybridomas. The class and subclass of the antibody produced by each of the established clones was $IgG_1$ for G1-5A2-2C8, $IgG_{20}$ for G2-2F2-3D11, and IgM for G2-2D10-3F5. 3,000,000 cells of each hybridoma were introduced into the peritoneal cavity of a BALB/c mouse to which 0.5 ml of pristane had been administered intraperitoneally about one week before. After 8–10 days, the ascites was collected. From the ascites collected from each animal, an antibody was purified by affinity chromatography using a protein G column.

Similarly, an anti-MDC protein polyclonal antibody was prepared by immunizing a rabbit with an immunizing antigen comprising His6-MDD(C1) obtained in Example 13.

Specifically, like the mouse, a rabbit was immunized with a mixture prepared by mixing a solution of His6-MDC(C1) (500–1000 µg/ml) in 3M urea/PBS with a complete adjuvant at a ratio of 1:1. After completion of the immunization, an antiserum was obtained and its antibody titer was measured using a polystyrene cup having a solid phase formed from the MBP-MDC(dC1) fusion protein obtained in Example 13. The antiserum was diluted 500- to 64,000-fold, 100 µl each of the dilutions were added to wells, and their antibody titers were tested with goat anti-rabbit IgG-HRP. Thus, the antibody titer was detectable up to the 64,000-fold dilution. Since no antibody reacting with MBP-MDC(dC1) was present in the serum before immunization, it could be confirmed that an antibody reacting specifically with the protein was produced. Furthermore, this antiserum was purified by affinity chromatography using a protein G column and a Sepharose column having the MBP-MDC(dC1) fusion protein immobilized therein.

A method for the determination of the MDC protein by ELISA using the purified monoclonal antibody and purified rabbit polyclonal antibody obtained in the above-described manner was established.

Figure 8:
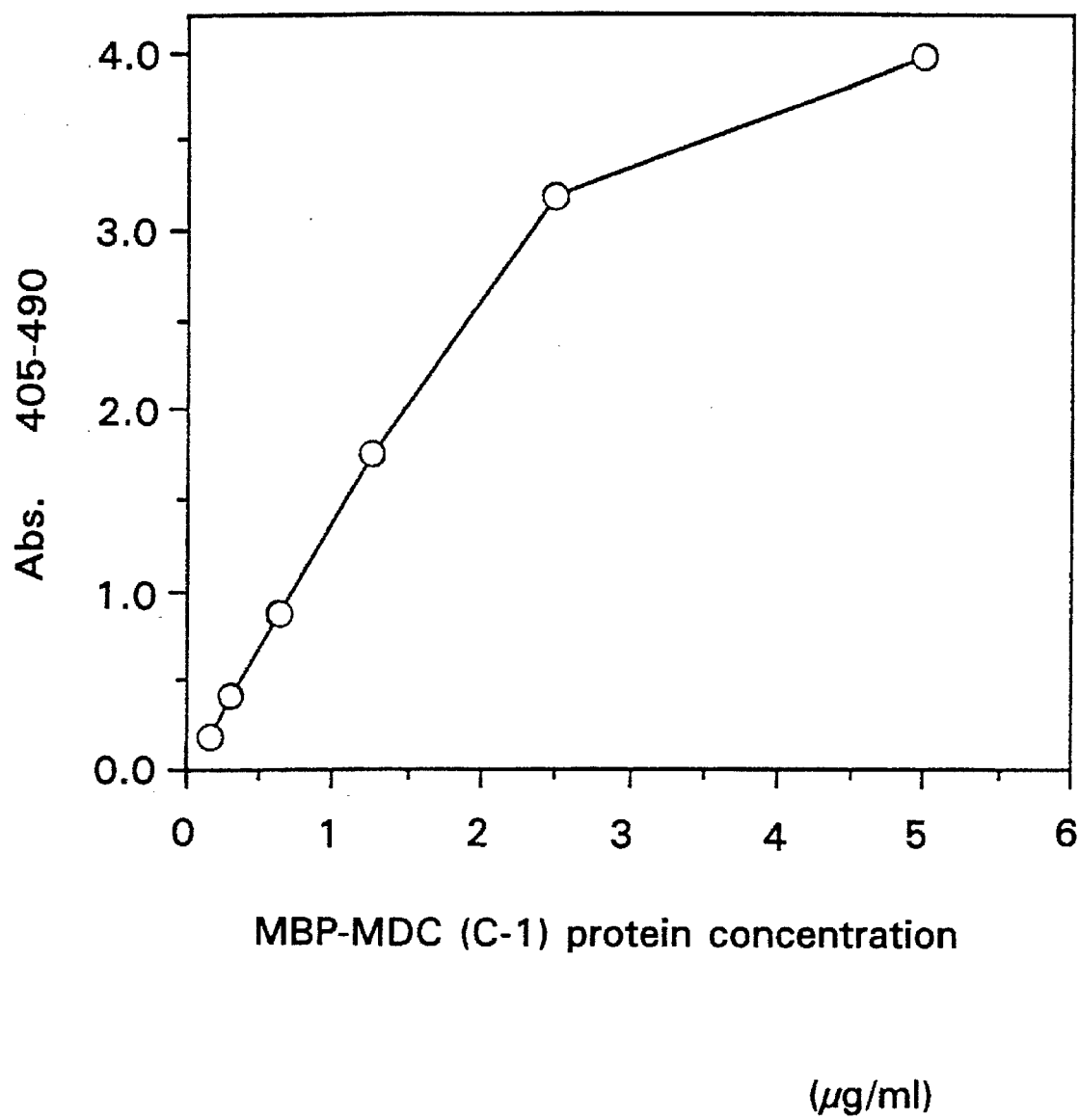
FIG. 8 is a graph showing a working curve for determining the concentration of the MDC protein by ELISA using a monoclonal antibody and a rabbit polyclonal antibody.

Specifically, the purified monoclonal antibody derived from a hybridoma (G2-2F2-3D11) was immobilized on a 96-well plate and blocked with BSA (bovine serum albumin). Test solutions containing purified MBP-MDC(C1) at concentrations of 0.156 to 5.00 µg/ml were prepared, added to wells in an amount of 100 µl per well, and reacted at room temperature for an hour. After the wells were washed, a solution (5 µg/ml) of the purified rabbit polyclonal antibody was added in an amount of 100 µl per well and reacted at room temperature for an hour. After the wells were washed, anti-rabbit IgG-HRP (5 µg/ml) was added in an amount of 100 µl per well and reacted at room temperature for an hour. After completion of the reaction, 2 mM sodium azide was added in an amount of 100 µl per well and the absorbances at 405 nm and 490 nm were measured. It was confirmed that the differential absorbances thus obtained were closely correlated with the concentrations of the test solutions, exhibiting an approximately linear relationship in the range of 0 to 2.5 µg/ml (see FIG. 8). This indicates that ELISA using these monoclonal antibody and rabbit polyclonal antibody can be used as a method for the determination of the MDC protein.

We claim:

1. An antibody that specifically binds to an MDC protein having a sequence selected from the group consisting of SEQ ID NO:1, SEQ ID NO:2, SEQ ID NO:3 and SEQ ID NO:4.

2. An antibody according to claim 1 wherein the MDC protein has SEQ ID NO:1.

3. An antibody according to claim 1, wherein the MDC protein has SEQ ID NO:2.

4. An antibody according to claim 1, wherein the MDC protein has SEQ ID NO:3.

5. An antibody according to claim 1, wherein the MDC protein has SEQ ID NO:4.

* * * * *